US006518018B1

(12) United States Patent
Szostak et al.

(10) Patent No.: US 6,518,018 B1
(45) Date of Patent: Feb. 11, 2003

(54) RNA-ANTIBODY FUSIONS AND THEIR SELECTION

(75) Inventors: Jack W. Szostak, Boston, MA (US); Richard W. Roberts, South Pasadena, CA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/238,710

(22) Filed: Jan. 28, 1999

Related U.S. Application Data

(63) Continuation of application No. 09/007,005, filed on Jan. 14, 1998, now Pat. No. 6,258,558.
(60) Provisional application No. 60/064,491, filed on Nov. 6, 1997, and provisional application No. 60/035,963, filed on Jan. 21, 1997.

(51) Int. Cl.[7] ............................ C12Q 1/68; C12P 21/06; C12P 19/34; C07H 21/04; C07K 16/00
(52) U.S. Cl. ..................... 435/6; 435/69.1; 435/91.21; 536/23.1; 536/23.4; 536/23.53; 530/387.1
(58) Field of Search ................. 435/91.21, 6, 69.1; 536/23.4, 23.53, 23.1; 530/387.1

(56) References Cited

U.S. PATENT DOCUMENTS

| | | | |
|---|---|---|---|
| 4,587,044 A | 5/1986 | Miller et al. | |
| 5,223,409 A | 6/1993 | Ladner et al. | |
| 5,264,563 A | 11/1993 | Huse | |
| 5,270,163 A | 12/1993 | Gold et al. | |
| 5,270,170 A | 12/1993 | Schatz et al. | |
| 5,391,723 A * | 2/1995 | Priest et al. ................. 536/23.1 |
| 5,432,018 A | 7/1995 | Dower et al. | |
| 5,498,530 A | 3/1996 | Schatz et al. | |
| 5,541,061 A | 7/1996 | Fodor et al. | |
| 5,605,793 A | 2/1997 | Stemmer | |
| 5,627,024 A | 5/1997 | Maruyama et al. ............ 435/5 |
| 5,639,603 A | 6/1997 | Dower et al. | |
| 5,643,768 A * | 7/1997 | Kawasaki ................. 435/91.21 |
| 5,658,754 A | 8/1997 | Kawasaki | |
| 5,723,323 A | 3/1998 | Kauffman et al. | |
| 5,733,731 A | 3/1998 | Schatz et al. | |
| 5,789,208 A | 8/1998 | Sharon ...................... 435/91.41 |
| 5,795,747 A | 8/1998 | Henco et al. | |
| 5,843,701 A * | 12/1998 | Gold et al. ................. 435/68.1 |
| 5,849,878 A | 12/1998 | Cantor et al. ............ 530/391.9 |
| 5,965,133 A | 10/1999 | Cantor et al. ............ 424/179.1 |
| 5,985,575 A | 11/1999 | Wickens et al. ................. 435/6 |
| 6,361,943 B1 * | 3/2002 | Yanagawa et al. .............. 435/6 |

FOREIGN PATENT DOCUMENTS

| | | |
|---|---|---|
| DE | 19646372 | 11/1996 |
| WO | WO 91/05058 | 4/1991 |
| WO | WO 92/02536 | 2/1992 |
| WO | WO 92/18645 | 10/1992 |
| WO | WO 93/03172 | 2/1993 |
| WO | WO 95/11922 | 5/1995 |
| WO | WO 96/22391 | 7/1996 |
| WO | WO 98/16636 | 4/1998 |
| WO | WO98/37186 * | 8/1998 |
| WO | WO 98/37186 | 8/1998 |
| WO | WO 98/58080 | 12/1998 |

OTHER PUBLICATIONS

Husimi et al., "Role of the Virus–Type Strategy in Encoded Molecular Evolution," Progress in Biophysics and Molecular Biology, vol. 65 (Suppl. 1), Abstract P–A5–04 (1996).
Niemeyer et al., "Oligonucleotide–Directed Self–Assembly of Proteins: Semisynthetic DNA—Streptavidin Hybrid Molecules as Connectors for the Generation of Macroscopic Arrays and the Construction of Supramolecular Bioconjugates," Nucl. Acid Res. 22:5530–5539 (1994).

(List continued on next page.)

Primary Examiner—W. Gary Jones
Assistant Examiner—B J Forman
(74) Attorney, Agent, or Firm—Clark & Elbing LLP

(57) ABSTRACT

Described herein are methods and reagents for the selection of protein molecules that make use of RNA-protein fusions.

12 Claims, 16 Drawing Sheets

OTHER PUBLICATIONS

Abelson, "Directed Evolution of Nucleic Acids by Independent Replication and Selection," Science 249:488–489 (1990).

Barrett et al., "A Monoclonal Antibody Specific for a Dynorphin Precursor," Neuropeptides 6:113–120 (1985).

Bartel et al., "HIV–1 Rev Regulation Involves Recognition of Non–Watson–Crick Base Pairs in Viral DNA," Cell 67:529–536 (1991).

Bartel and Szostak, "Isolation of New Ribozymes from a Large Pool of Random Sequences," Science 261:1411–1418 (1993).

Beaudry and Joyce, "Directed Evolution of an RNA Enzyme," Science 257:635–641 (1992).

Blackwell et al., "Differences and Similarities in DNA–Binding Preferences of MyoD and E2A Protein Complexes Revealed by Binding Site Selection," Science 250:1104–1110 (1990).

Bock et al., "Selection of Single–Stranded DNA Molecules that Bind and Inhibit Human Thrombin," Nature 355:564–566 (1992).

Botstein et al., "Strategies and Applications of in Vitro Mutagenesis," Science 229:1193–1201 (1985).

Brenner and Lerner, "Encoded Combinatorial Chemistry," Proc. Natl. Acad. Sci. USA 89:5381–5383 (1992).

Bujard et al., "[26] A T5 Promoter–Based Transcription–Translation System for the Analysis of Proteins in Vitro an in Vivo," Methods in Enzymology 155:416–433 (1987).

Chapman and Szostak, "Isolation of a Ribozyme with 5'–5' Ligase Activity," Chemistry and Biology 2:325–333 (1995).

Clackson et al., "In Vitro Selection from Protein and Peptide Libraries," Tibtech 12:173–184 (1994).

Cuenoud and Szostak, "A DNA Metalloenzyme with DNA Ligase Activity," Nature 375:611–614 (1995).

Cull et al., "Screening for Receptor Ligands Using Large Libraries of Peptides Linked to the C Terminal of the lac Repressor," Proc. Natl. Acad. Sci. USA 89:1865–1869 (1992).

Cwirla et al., "Peptides on Phage: A Vast Library of Peptides for Identifying Ligands," Proc. Natl. Acad. Sci. 87:6378–6382 (1990).

Devlin et al., "Random Peptide Libraries: A Source of Specific Protein Binding Molecules," Science 249:404–406 (1990).

Eigen et al., "Molecular Quasi–Species," Journal of Physical Chemistry 92:6881–6891 (1988).

Eigen et al., "The Hypercycle. Coupling of RNA and Protein Biosynthesis in the Infection Cycle of an RNA Bacteriophage," Biochemistry 30:11005–11018 (1991).

Eigen, "Viral Quasispecies," Scientific American 269:32–39 (1993).

Eigen, "New Concepts for Dealing with the Evolution of Nucleic Acids," Cold Spring Harb. Symp. Quant. Biol. 52:307–320 (1987).

Eigen et al., "Evolutionary Molecular Engineering Based on RNA Replication," Pure & Appl. Chem. 56(8):967–978 (1984).

Ekland and Bartel, "The Secondary Structure and Sequence Optimization of an RNA Ligase Ribozyme," Nucleic Acids Research 23:3231–3238 (1995).

Ellington and Szostak, "Selection in vitro of Single–Stranded DNA Molecules that Fold into Specific Ligand–Binding Structures," Nature 355:850–852 (1992).

Ellington and Szostak, "In vitro Selection of RNA Molecules that Bind Specific Ligands," Nature 346:818–822 (1990).

Ellman et al., "Biosynthetic Method for Introducing Unnatural Amino Acids Site–Specifically into Proteins," Methods in Enzymology 202:301–336 (1991).

Fraser and Rich, "Synthesis and Aminoacylation of 3'–Amino–3'deoxy Transfer RNA and Its Activity in Ribosomal Protein Synthesis," Proc. Natl. Acad. Sci. USA 70:2671–2675 (1973).

Gerusk et al., "High–Affinity Peptide Ligands to Prostate–Specific Antigen Identified by Polysome Selection," Biochem. Biophys. Res. Commun. 232(2):578–582 (1997).

Geysen et al., "Use of Peptide Synthesis to Probe Viral Antigens for Epitopes to a Resolution of a Single Amino Acid," Proc. Natl. Acad. Sci. 81:3998–4002 (1984).

Green et al. "In vitro Genetic Analysis of the Tetrahymena Self–Splicing Intron," Nature 347:406–408 (1990).

Guatelli et al., "Isothermal, in vitro Amplification of Nucleic Acids by a Multienzyme Reaction Modeled Retroviral Replication," Proc. Natl. Acad. Sci. 87:1874–1878 (1990).

Hanes et al., "In vitro and Evolution of Functional Proteins by Using Ribosome Display," Proc. Natl. Acad. Sci. USA 94:4937–4942 (1997).

Higuchi, "Using PCR to Engineer DNA,"In: PCR Technology Principles and Applications for DNA Amplification, Henry A. Erlich, ed., Stockton Press, pp. 61–70 (1989).

Horwitz et al., "Selection of New Biological Activities from Random Nucleotide Sequences: Evolutionary and Practical Considerations," Genome 31:112–117 (1989).

Hui et al., "Mutagenesis of the Three Bases Preceding the Start Codon of the B–galacosidase mRNA and its Effect on Translation in Escherichia coli," The EMBO Journal 3:623–629 (1984).

Hunkapiller et al., "A Microchemical Facility for the Analysis and Synthesis of Genes and Proteins," Nature 310:105–111 (1984).

Irvine et al., "Systematic Evolution of Ligands by Exponential Enrichment with Integrated Optimization by Non–Linear Analysis," J. Mol. Biol. 222:739–761 (1991).

Jamieson et al., "In Vitro Selection of Zinc Fingers with Altered DNA–Binding Specificity," Biochemistry 33:5689–5695 (1994).

Korman et al., "cDNA Clones for the Heavy Chain of HLA–DR Antigens Obtained after Immunopurification of Polysomes by Monoclonal Antibody," Proc. Natl. Acad. Sci. USA 79:1844–1848 (1982).

Kraus et al., "Purification of Low–Abundance Messenger RNAs from Rat Liver by Polysome Immunodasorption," Proc. Natl. Acad. Sci. 79:4015–4019 (1982).

Krayevsky and Kukhanova, "The Peptidyltransferase Center of Ribosomes," Progress in Nucleic Acid Research and Molecular Biology 23:1–51 (1979).

Leung et al., "A Method for Random Mutagensis of a defined DNA Segment using a Modified Polymerase Chain Reaction," Technique 1:11–15 (1989).

Lizardi et al., "Exponential Amplication of Recombinant–RNA Hybridization Probes," Biotechnology 6:1197–1202, (1988).

Lohse and Szostak, "Ribozyme–Catalysed Amino–Acid Transfer Reactions," Nature 381:442–444 (1996).

Lorsch and Szostak, "In vitro Evolution of New Ribozymes with Polynucleotide Kinase Activity," Nature 371:31–36 (1994).

Matteucci et al., "Targeted Random Mutagenesis: The use of Ambiguously Synthesized Oligonucleotides to Mutagenize Sequences Immediately 5' of an ATG Initiation Codon," *Nuclueic Acids Research* 11:3113–3121, (1983).

Mattheakis et al., "An in vitro Polysome Display System for Identifying Ligands From Very Large Peptide Libraries," *Proc. Natl. Acad. Sci. USA* 91:9022–9026 (1994).

Mattheakis et al., "Cell–Free Synthesis of Peptide Libraries Displayed on Polysomes," *Methods in Enzymology* 267:195–205 (1996).

Matthews et al., "Substrate Phage: Selection of Protease Substrates by Monovalent Phage Display," *Science* 260:1113–1117 (1993).

McCafferty et al., "Phage Antibodies: Filamentous Phage Displaying antibody Variable Domians," *Nature* 348:552–554 (1990).

Milstein, "Monoclonal Antibodies," *Sci Amer.* 243:66–74 (1980).

Nemoto et al., "In vitro virus: Bonding of mRNA Bearing Puromycin at the 3'–Terminal End to the C–Terminal End of its Encoded Protein on the Ribosome In vitro," *FEBS* 414:405–408 (1997).

Nielsen et al., "Synthetic Methods for the Implementation of Encoded Combinatorial Chemistry," *J. Am. Chem. Soc.* 115:9812–9813 (1993).

Oehlenschlager et al., "30 Years Later—A New Approach to SOL Spiegelman's and Leslie Orgels in vitro Evolutionary Studies. Dedicated to Leslie Orgel on the Occasion of his $70^{th}$ birthday," *Orig. Life. Evol. Biosph.* 27:437–457 (1997).

Ohno, "Birth of a Unique Enzyme from an Alternative Reading Frame of the Preexisted, Internally Repetitious Coding Sequence," *Proc. Natl. Acad. Sci. USA* 81:2421–2425 (1984).

Oldenburg et al., "Peptide Ligands for a Sugar–Binding Protein Isolated from a Random Peptide Library," *Proc. Natl. Acad. Sci. USA* 89:5393–5397 (1992).

Oliphant et al., "Defining the Sequence Specificity of DNA–Binding Proteins by Selecting Binding Sites from Random–Sequence Oligonucleotides: Analysis of Yeast GCN4 Protein," *Molecular and Cellular Biology* 9:2944–2949 (1989).

Parmley and Smith, "Antibody–Selectable Filamentous fd Phage Vectors: Affinity Purifications of Target Genes," *Gene* 73:305–318 (1988).

Payvar et al., "Improvements in Immunoprecipitation of Specific Messenger RNA Isolation of Highly Purified Conalbumin mRNA in High Yield," *Eur. J. Biochem.* 101:271–282 (1979).

Peters et al., "N–terminal Amino Acid Sequences and C–terminal Residues of Rat Alpha–fetoprotein Electrophoretic Variants, 'Fast' and 'Slow'," *Scand. J. Immunol.* 8:299–304 (1978).

Pollock and Treisman, "A Sensitive Method for the Determination of Protein–DNA Binding Specificities," *Nucleic Acids Research* 18:6197–6204 (1990).

Rebar et al., "Zinc Finger Phage: Affinity Selection of Fingers with New DNA–Binding Specificities," *Science* 263:671–673 (1994).

Roberts, "In vitro Selection of Proteins VIA RNA–Proteins Fusions," FY 95, Abstract.

Roberts, "In vitro Selection of Proteins VIA RNA–Proteins Fusions," FY 96, Abstract.

Roberts and Szostak, "RNA–Peptide Fusions for the in vitro Selection of Peptides and Proteins," *Proc. Natl. Acad. Sci. USA* 94:12297–12302 (1997).

Robertson and Joyce, "Selection in vitro of an RNA Enzyme that Specifically Cleaves Single–Stranded DNA,"*Nature* 344:467–468 (1990).

Sarkar et al., "Characterization of Polymerase Chain Reaction Amplification of Specific Alleles," *Analytical Biochemistry* 186:64–68 (1990).

Schatz, "Use of Peptide Libraries to Map the Substrate Specificity of a Peptide–Modifying Enzyme: A 13 Residue Consensus Peptide Specifies Biotinylation in *Escherichia coli,"Bio/Technology* 11:1138–1143 (1993).

Scott et al., "Searching for Peptide Ligands with an Epitope Library," *Science* 249:386–390 (1990).

Scott et al., "A Family of Concanavalin A–Binding Peptides from a Hexapeptide Epitope Library," *Proc. Natl. Acad. Sci. USA* 89:5398–5402 (1992).

Smith, "Filamentous Fusion Phage: Novel Expression Vectors that Display Cloned Antigens on the Virion Surface," *Science* 228:1315–1317 (1985).

Smith et al., "Action of Puromycin in Polyadenylic Acid–Directed Polylysine Synthesis," *J. Mol. Biol.* 13:617–628 (1965).

Stemmer et al., "Rapid Evolution of a Protein in vitro by DNA Shuffling," *Nature* 370:389–391 (1994).

Stormo and Yoshioka, "Specificity of the Mnt Protein Determined by Binding to Randomized Operators," *Proc. Natl. Acad. Sci. USA* 88:5699–5703 (1991).

Thiesen and Bach, "Target Detection Assay (TDA): A Versatile Procedure to Determine DNA Binding Sites as Demonstrated on SP1 Protein," *Nucleic Acids Research* 18:3203–3209 (1990).

Traut and Monro, "The Puromycin Reaction and its Relation to Protein Synthesis," *J. Mol. Biol.* 10:63–72 (1964).

Tuerk and Gold, "Systematic Evolution of Ligands by Exponential Enrichment: RNA Ligands to Bacteriophage T4 DNA Polymerase," *Science* 249:505–510 (1990).

Wells et al., "Cassette Mutagenesis: An Efficient Method for Generation of Multiple Mutations at Defined Sites," *Gene* 34:315–323 (1985).

* cited by examiner

Fig. 1A T7 PROMOTER  TE  AUG  RANDOMIZED REGION  3' CONSTANT REGION

ORF

Fig. 1B

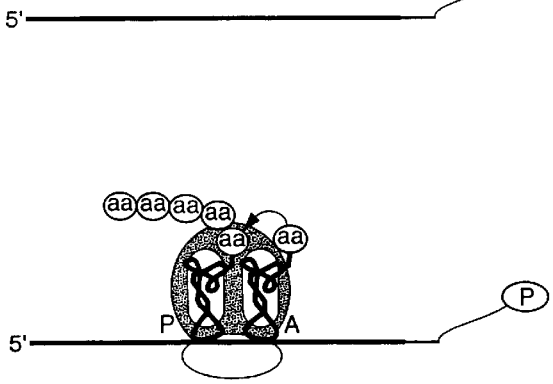

PUROMYCIN-TETHERED OLIGO IS LIGATED TO mRNA (GENERATED FROM ABOVE CONSTRUCT) IN THE PRESENCE OF A SPLINT AND DNA LIGASE

NOTE: FOR SHORT ORFS, THIS WHOLE TEMPLATE CAN BE MADE SYNTHETICALLY

Fig. 1C

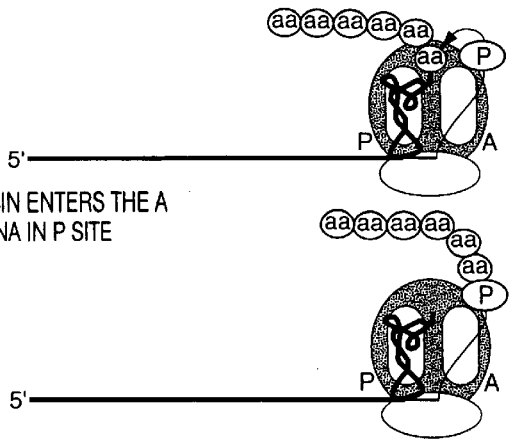

IN VITRO TRANSLATION PROCEEDS NORMALLY FROM THE 5' TO THE 3' END OF THE mRNA

COVALENTLY LINKED PUROMYCIN ENTERS THE A SITE AND ATTACKS PEPTIDYL tRNA IN P SITE

RELEASE OF RNA-PROTEIN FUSION WITH HIGH SALT WASH OF RIBOSOME

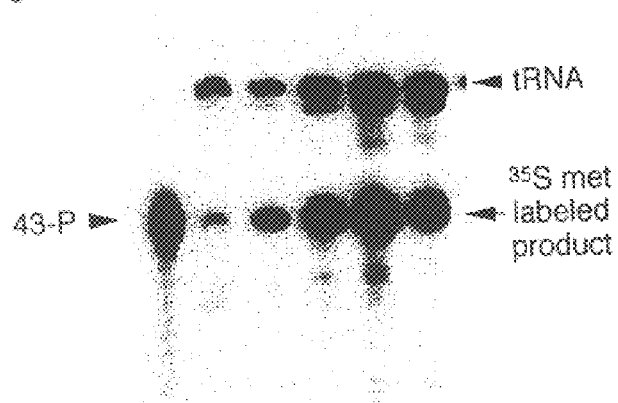
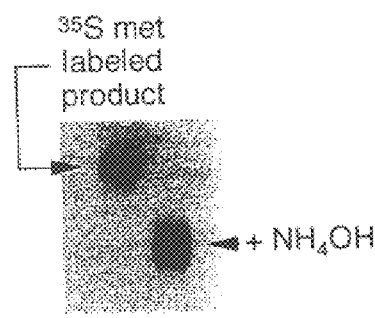
Fig. 6A  Fig. 6B
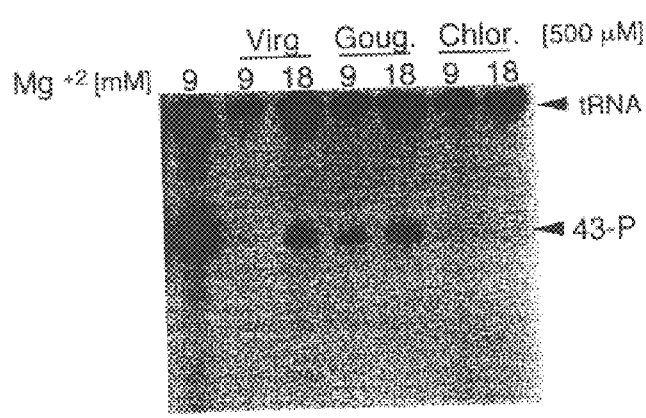
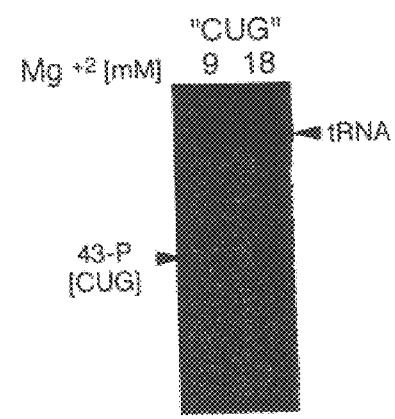
Fig. 6C  Fig. 6D

Effects of RNase A and Proteinase K on fusion

RNA-ANTIBODY FUSIONS AND THEIR SELECTION

BACKGROUND OF THE INVENTION

This application is a continuation of application, Szostak et al., U.S. Ser. No. 09/007,005, filed Jan. 14, 1998, now U.S. Pat. No. 6,258,358 which claims benefit from provisional applications, Szostak et al., U.S. Ser. No. 60/064,491, filed Nov. 6, 1997, now abandoned, and U.S. Ser. No. 60/035,963, filed Jan. 21, 1997, now abandoned.

This invention relates to protein selection methods.

The invention was made with government support under grant F32 GM17776-01 and F32 GM17776-02. The government has certain rights in the invention.

Methods currently exist for the isolation of RNA and DNA molecules based on their functions. For example, experiments of Ellington and Szostak (Nature 346:818 (1990); and Nature 355:850 (1992)) and Tuerk and Gold (Science 249:505 (1990); and J. Mol. Biol 222:739 (1991)) have demonstrated that very rare (i.e., less than 1 in $10^{13}$) nucleic acid molecules with desired properties may be isolated out of complex pools of molecules by repeated rounds of selection and amplification. These methods offer advantages over traditional genetic selections in that (i) very large candidate pools may be screened ($>10^{15}$), (ii) host viability and in vivo conditions are not concerns, and (iii) selections may be carried out even if an in vivo genetic screen does not exist. The power of in vitro selection has been demonstrated in defining novel RNA and DNA sequences with very specific protein binding functions (see, for example, Tuerk and Gold, Science 249:505 (1990); Irvine et al., J. Mol. Biol 222:739 (1991); Oliphant et al., Mol. Cell Biol. 9:2944 (1989); Blackwell et al., Science 250:1104 (1990); Pollock and Treisman, Nuc. Acids Res. 18:6197 (1990); Thiesen and Bach, Nuc. Acids Res. 18:3203 (1990); Bartel et al., Cell 57:529 (1991); Stormo and Yoshioka, Proc. Natl. Acad. Sci. USA 88:5699 (1991); and Bock et al., Nature 355:564 (1992)), small molecule binding functions (Ellington and Szostak, Nature 346:818 (1990); Ellington and Szostak, Nature 355:850 (1992)), and catalytic functions (Green et al., Nature 347:406 (1990); Robertson and Joyce, Nature 344:467 (1990); Beaudry and Joyce, Science 257:635 (1992); Bartel and Szostak, Science 261:1411 (1993); Lorsch and Szostak, Nature 371:31–36 (1994); Cuenoud and Szostak, Nature 375:611–614 (1995); Chapman and Szostak, Chemistry and Biology 2:325–333 (1995); and Lohse and Szostak, Nature 381:442–444 (1996)). A similar scheme for the selection and amplification of proteins has not been demonstrated.

SUMMARY OF THE INVENTION

The purpose of the present invention is to allow the principles of in vitro selection and in vitro evolution to be applied to proteins. The invention facilitates the isolation of proteins with desired properties from large pools of partially or completely random amino acid sequences. In addition, the invention solves the problem of recovering and amplifying the protein sequence information by covalently attaching the mRNA coding sequence to the protein molecule.

In general, the inventive method consists of an in vitro or in situ transcription/translation protocol that generates protein covalently linked to the 3' end of its own mRNA, i.e., an RNA-protein fusion. This is accomplished by synthesis and in vitro or in situ translation of an mRNA molecule with a peptide acceptor attached to its 3' end. One preferred peptide acceptor is puromycin, a nucleoside analog that adds to the C-terminus of a growing peptide chain and terminates translation. In one preferred design, a DNA sequence is included between the end of the message and the peptide acceptor which is designed to cause the ribosome to pause at the end of the open reading frame, providing additional time for the peptide acceptor (for example, puromycin) to accept the nascent peptide chain before hydrolysis of the peptidyl-tRNA linkage.

If desired, the resulting RNA-protein fusion allows repeated rounds of selection and amplification because the protein sequence information may be recovered by reverse transcription and amplification (for example, by PCR amplification as well as any other amplification technique, including RNA-based amplification techniques such as 3SR or TSA). The amplified nucleic acid may then be transcribed, modified, and in vitro or in situ translated to generate mRNA-protein fusions for the next round of selection. The ability to carry out multiple rounds of selection and amplification enables the enrichment and isolation of very rare molecules, e.g., one desired molecule out of a pool of $10^{15}$ members. This in turn allows the isolation of new or improved proteins which specifically recognize virtually any target or which catalyze desired chemical reactions.

Accordingly, in a first aspect, the invention features a method for selection of a desired protein, involving the steps of: (a) providing a population of candidate RNA molecules, each of which includes a translation initiation sequence and a start codon operably linked to a candidate protein coding sequence and each of which is operably linked to a peptide acceptor at the 3' end of the candidate protein coding sequence; (b) in vitro or in situ translating the candidate protein coding sequences to produce a population of candidate RNA-protein fusions; and (c) selecting a desired RNA-protein fusion, thereby selecting the desired protein.

In a related aspect, the invention features a method for selection of a DNA molecule which encodes a desired protein, involving the steps of: (a) providing a population of candidate RNA molecules, each of which includes a translation initiation sequence and a start codon operably linked to a candidate protein coding sequence and each of which is operably linked to a peptide acceptor at the 3' end of the candidate protein coding sequence; (b) in vitro or in situ translating the candidate protein coding sequences to produce a population of candidate RNA-protein fusions; (c) selecting a desired RNA-protein fusion; and (d) generating from the RNA portion of the fusion a DNA molecule which encodes the desired protein.

In another related aspect, the invention features a method for selection of a protein having an altered function relative to a reference protein, involving the steps of: (a) producing a population of candidate RNA molecules from a population of DNA templates, the candidate DNA templates each having a candidate protein coding sequence which differs from the reference protein coding sequence, the RNA molecules each comprising a translation initiation sequence and a start codon operably linked to the candidate protein coding sequence and each being operably linked to a peptide acceptor at the 3' end; (b) in vitro or in situ translating the candidate protein coding sequences to produce a population of candidate RNA-protein fusions; and (c) selecting an RNA-protein fusion having an altered function, thereby selecting the protein having the altered function.

In yet another related aspect, the invention features a method for selection of a DNA molecule which encodes a protein having an altered function relative to a reference protein, involving the steps of: (a) producing a population of candidate RNA molecules from a population of candidate DNA templates, the candidate DNA templates each having a candidate protein coding sequence which differs from the reference protein coding sequence, the RNA molecules each comprising a translation initiation sequence and a start codon operably linked to the candidate protein coding sequence and each being operably linked to a peptide acceptor at the 3' end; (b) in vitro or in situ translating the candidate protein coding sequences to produce a population of RNA-protein fusions; (c) selecting an RNA-protein fusion having an altered function; and (d) generating from the RNA portion of the fusion a DNA molecule which encodes the protein having the altered function.

In yet another related aspect, the invention features a method for selection of a desired RNA, involving the steps of: (a) providing a population of candidate RNA molecules, each of which includes a translation initiation sequence and a start codon operably linked to a candidate protein coding sequence and each of which is operably linked to a peptide acceptor at the 3' end of the candidate protein coding sequence; (b) in vitro or in situ translating the candidate protein coding sequences to produce a population of candidate RNA-protein fusions; and (c) selecting a desired RNA-protein fusion, thereby selecting the desired RNA.

In preferred embodiments of the above methods, the peptide acceptor is puromycin; each of the candidate RNA molecules further includes a pause sequence or further includes a DNA or DNA analog sequence covalently bonded to the 3' end of the RNA; the population of candidate RNA molecules includes at least $10^9$, preferably, at least $10^{10}$, more preferably, at least $10^{11}$, $10^{12}$, or $10^{13}$, and, most preferably, at least $10^{14}$ different RNA molecules; the in vitro translation reaction is carried out in a lysate prepared from a eukaryotic cell or portion thereof (and is, for example, carried out in a reticulocyte lysate or wheat germ lysate); the in vitro translation reaction is carried out in an extract prepared from a prokaryotic cell (for example, $E.$ $coli$) or portion thereof; the selection step involves binding of the desired protein to an immobilized binding partner;

the selection step involves assaying for a functional activity of the desired protein; the DNA molecule is amplified; the method further involves repeating the steps of the above selection methods; the method further involves transcribing an RNA molecule from the DNA molecule and repeating steps (a) through (d); following the in vitro translating step, the method further involves an incubation step carried out in the presence of 50–100 mM $Mg^{2+}$; and the RNA-protein fusion further includes a nucleic acid or nucleic acid analog sequence positioned proximal to the peptide acceptor which increases flexibility.

In other related aspects, the invention features an RNA-protein fusion selected by any of the methods of the invention; a ribonucleic acid covalently bonded though an amide bond to an amino acid sequence, the amino acid sequence being encoded by the ribonucleic acid; and a ribonucleic acid which includes a translation initiation sequence and a start codon operably linked to a candidate protein coding sequence, the ribonucleic acid being operably linked to a peptide acceptor (for example, puromycin) at the 3' end of the candidate protein coding sequence.

In a second aspect, the invention features a method for selection of a desired protein or desired RNA through enrichment of a sequence pool. This method involves the steps of: (a) providing a population of candidate RNA molecules, each of which includes a translation initiation sequence and a start codon operably linked to a candidate protein coding sequence and each of which is operably linked to a peptide acceptor at the 3' end of the candidate protein coding sequence; (b) in vitro or in situ translating the candidate protein coding sequences to produce a population of candidate RNA-protein fusions; (c) contacting the population of RNA-protein fusions with a binding partner specific for either the RNA portion or the protein portion of the RNA-protein fusion under conditions which substantially separate the binding partner-RNA-protein fusion complexes from unbound members of the population; (d) releasing the bound RNA-protein fusions from the complexes; and (e) contacting the population of RNA-protein fusions from step (d) with a binding partner specific for the protein portion of the desired RNA-protein fusion under conditions which substantially separate the binding partner-RNA-protein fusion complex from unbound members of said population, thereby selecting the desired protein and the desired RNA.

In preferred embodiments, the method further involves repeating steps (a) through (e). In addition, for these repeated steps, the same or different binding partners may be used, in any order, for selective enrichment of the desired RNA-protein fusion. In another preferred embodiment, step (d) involves the use of a binding partner (for example, a monoclonal antibody) specific for the protein portion of the desired fusion. This step is preferably carried out following reverse transcription of the RNA portion of the fusion to generate a DNA which encodes the desired protein. If desired, this DNA may be isolated and/or PCR amplified. This enrichment technique may be used to select a desired protein or may be used to select a protein having an altered function relative to a reference protein.

In other preferred embodiments of the enrichment methods, the peptide acceptor is puromycin; each of the candidate RNA molecules further includes a pause sequence or further includes a DNA or DNA analog sequence covalently bonded to the 3' end of the RNA; the population of candidate RNA molecules includes at least $10^9$, preferably, at least $10^{10}$, more preferably, at least $10^{11}$, $10^{12}$, or $10^{13}$, and, most preferably, at least $10^{14}$ different RNA molecules; the in vitro translation reaction is carried out in a lysate prepared from a eukaryotic cell or portion thereof (and is, for example, carried out in a reticulocyte lysate or wheat germ lysate); the in vitro translation reaction is carried out in an extract prepared from a prokaryotic cell or portion thereof (for example, $E.$ $coli$); the DNA molecule is amplified; at least one of the binding partners is immobilized on a solid support; following the in vitro translating step, the method further involves an incubation step carried out in the presence of 50–100 mM $Mg^{2+}$; and the RNA-protein fusion further includes a nucleic acid or nucleic acid analog sequence positioned proximal to the peptide acceptor which increases flexibility.

In a related aspect, the invention features kits for carrying out any of the selection methods described herein.

In a third and final aspect, the invention features a microchip that includes an array of immobilized single-stranded nucleic acids, the nucleic acids being hybridized to RNA-protein fusions. Preferably, the protein component of the RNA-protein fusion is encoded by the RNA.

As used herein, by a "population" is meant more than one molecule (for example, more than one RNA, DNA, or RNA-protein fusion molecule). Because the methods of the invention facilitate selections which begin, if desired, with large numbers of candidate molecules, a "population" according to the invention preferably means more than $10^9$ molecules, more preferably, more than $10^{11}$, $10^{12}$, or $10^{13}$ molecules, and, most preferably, more than $10^{13}$ molecules.

By "selecting" is meant substantially partitioning a molecule from other molecules in a population. As used herein, a "selecting" step provides at least a 2-fold, preferably, a 30-fold, more preferably, a 100-fold, and, most preferably, a 1000-fold enrichment of a desired molecule relative to undesired molecules in a population following the selection step. As indicated herein, a selection step may be repeated any number of times, and different types of selection steps may be combined in a given approach.

By a "protein" is meant any two or more naturally occurring or modified amino acids joined by one or more peptide bonds. "Protein" and "peptide" are used interchangeably herein.

By "RNA" is meant a sequence of two or more covalently bonded, naturally occurring or modified ribonucleotides. One example of a modified RNA included within this term is phosphorothioate RNA.

By a "translation initiation sequence" is meant any sequence which is capable of providing a functional ribosome entry site. In bacterial systems, this region is sometimes referred to as a Shine-Dalgarno sequence.

By a "start codon" is meant three bases which signal the beginning of a protein coding sequence. Generally, these bases are AUG (or ATG); however, any other base triplet capable of being utilized in this manner may be substituted.

By "covalently bonded" to a peptide acceptor is meant that the peptide acceptor is joined to a "protein coding sequence" either directly through a covalent bond or indirectly through another covalently bonded sequence (for example, DNA corresponding to a pause site).

By a "peptide acceptor" is meant any molecule capable of being added to the C-terminus of a growing protein chain by the catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Elhman et al., Meth. Enzymol. 202:301, 1991), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimetics of the combined nucleotide-amino acid structure.

By a peptide acceptor being positioned "at the 3' end" of a protein coding sequence is meant that the peptide acceptor molecule is positioned after the final codon of that protein coding sequence. This term includes, without limitation, a peptide acceptor molecule that is positioned precisely at the 3' end of the protein coding sequence as well as one which is separated from the final codon by intervening coding or non-coding sequence (for example, a sequence corresponding to a pause site). This term also includes constructs in which coding or non-coding sequences follow (that is, are 3' to) the peptide acceptor molecule. In addition, this term encompasses, without limitation, a peptide acceptor molecule that is covalently bonded (either directly or indirectly through intervening nucleic acid sequence) to the protein coding sequence, as well as one that is joined to the protein coding sequence by some non-covalent means, for example, through hybridization using a second nucleic acid sequence that binds at or near the 3' end of the protein coding sequence and that itself is bound to a peptide acceptor molecule.

By an "altered function" is meant any qualitative or quantitative change in the function of a molecule.

By a "pause sequence" is meant a nucleic acid sequence which causes a ribosome to slow or stop its rate of translation.

By "binding partner," as used herein, is meant any molecule which has a specific, covalent or non-covalent affinity for a portion of a desired RNA-protein fusion. Examples of binding partners include, without limitation, members of antigen/antibody pairs, protein/inhibitor pairs, receptor/ligand pairs (for example cell surface receptor/ligand pairs, such as hormone receptor/peptide hormone pairs), enzyme/substrate pairs (for example, kinase/substrate pairs), lectin/carbohydrate pairs, oligomeric or heterooligomeric protein aggregates, DNA binding protein/DNA binding site pairs, RNA/protein pairs, and nucleic acid duplexes, heteroduplexes, or ligated strands, as well as any molecule which is capable of forming one or more covalent or non-covalent bonds (for example, disulfide bonds) with any portion of an RNA-protein fusion. Binding partners include, without limitation, any of the "selection motifs" presented in FIG. 2.

By a "solid support" is meant, without limitation, any column (or column material), bead, test tube, microtiter dish, solid particle (for example, agarose or sepharose), microchip (for example, silicon, silicon-glass, or gold chip), or membrane (for example, the membrane of a liposome or vesicle) to which an affinity complex may be bound, either directly or indirectly (for example, through other binding partner intermediates such as other antibodies or Protein A), or in which an affinity complex may be embedded (for example, through a receptor or channel).

The presently claimed invention provides a number of significant advantages. To begin with, it is the first example of this type of scheme for the selection and amplification of proteins. This technique overcomes the impasse created by the need to recover nucleotide sequences corresponding to desired, isolated proteins (since only nucleic acids can be replicated). In particular, many prior methods that allowed the isolation of proteins from partially or fully randomized pools did so through an in vivo step. Methods of this sort include monoclonal antibody technology (Milstein, Sci. Amer. 243:66 (1980); and Schultz et al., J. Chem. Engng. News 68:26 (1990)), phage display (Smith, Science 228:1315 (1985); Parmley and Smith, Gene 73:305 (1988); and McCafferty et al., Nature 348:552 (1990)), peptide-lac repressor fusions (Cull et al., Proc. Natl. Acad. Sci. USA 89:1865 (1992)), and classical genetic selections. Unlike the present technique, each of these methods relies on a topological link between the protein and the nucleic acid so that the information of the protein is retained and can be recovered in readable, nucleic acid form.

In addition, the present invention provides advantages over the stalled translation method (Tuerk and Gold, Science 249:505 (1990); Irvine et al., J. Mol. Biol 222:739 (1991); Korman et al., Proc. Natl. Acad. Sci. USA 79:1844–1848 (1982); Mattheakis et al., Proc. Natl. Acad. Sci. USA 91:9022–9026 (1994); Mattheakis et al., Meth. Enzymol. 267:195 (1996); and Hanes and Pluckthun, Proc. Natl. Acad. Sci. USA 94:4937 (1997)), a technique in which selection is for some property of a nascent protein chain that is still complexed with the ribosome and its mRNA. Unlike the stalled translation technique, the present method does not rely on maintaining the integrity of an mRNA: ribosome: nascent chain ternary complex, a complex that is very fragile and is therefore limiting with respect to the types of selections which are technically feasible.

The present method also provides advantages over the branched synthesis approach proposed by Brenner and Lerner (Proc. Natl. Acad. Sci. USA 89:5381–5383 (1992)), in which DNA-peptide fusions are generated, and genetic information is theoretically recovered following one round of selection. Unlike the branched synthesis approach, the present method does not require the regeneration of a peptide from the DNA portion of a fusion (which, in the branched synthesis approach, is generally accomplished by individual rounds of chemical synthesis). Accordingly, the present method allows for repeated rounds of selection using populations of candidate molecules. In addition, unlike the branched synthesis technique, which is generally limited to the selection of fairly short sequences, the present method is applicable to the selection of protein molecules of considerable length.

In yet another advantage, the present selection and directed evolution technique can make use of very large and complex libraries of candidate sequences. In contrast, existing protein selection methods which rely on an in vivo step are typically limited to relatively small libraries of somewhat limited complexity. This advantage is particularly important when selecting functional protein sequences considering, for example, that $10^{13}$ possible sequences exist for a peptide of only 10 amino acids in length. In classical genetic techniques, lac repressor fusion approaches, and phage display methods, maximum complexities generally fall orders of magnitude below $10^{13}$ members. Large library size also provides an advantage for directed evolution applications, in that sequence space can be explored to a greater depth around any given starting sequence.

The present technique also differs from prior approaches in that the selection step is context-independent. In many other selection schemes, the context in which, for example, an expressed protein is present can profoundly influence the nature of the library generated. For example, an expressed protein may not be properly expressed in a particular system or may not be properly displayed (for example, on the surface of a phage particle). Alternatively, the expression of a protein may actually interfere with one or more critical steps in a selection cycle, e.g., phage viability or infectivity, or lac repressor binding. These problems can result in the loss of functional molecules or in limitations on the nature of the selection procedures that may be applied.

Finally, the present method is advantageous because it provides control over the repertoire of proteins that may be tested. In certain techniques (for example, antibody selection), there exists little or no control over the nature of the starting pool. In yet other techniques (for example, lac fusions and phage display), the candidate pool must be expressed in the context of a fusion protein. In contrast, RNA-protein fusion constructs provide control over the nature of the candidate pools available for screening. In addition, the candidate pool size has the potential to be as high as RNA or DNA pools (~$10^{15}$ members), limited only by the size of the in vitro translation reaction performed. And the makeup of the candidate pool depends completely on experimental design; random regions may be screened in isolation or within the context of a desired fusion protein, and most if not all possible sequences may be expressed in candidate pools of RNA-protein fusions.

Other features and advantages of the invention will be apparent from the following detailed description, and from the claims.

DETAILED DESCRIPTION

The drawings will first briefly be described.

BRIEF DESCRIPTION OF THE DRAWINGS

FIGS. 1A–1C are schematic representations of steps involved in the production of RNA-protein fusions. FIG. 1A illustrates a sample DNA construct for generation of an RNA portion of a fusion. FIG. 1B illustrates the generation of an RNA/puromycin conjugate. And FIG. 1C illustrates the generation of an RNA-protein fusion.

FIGS. 6A–6H are photographs showing the incorporation of $^{35}S$ methionine ($^{35}S$ met) into translation templates. FIG. 6A demonstrates magnesium ($Mg^{2+}$) dependence of the reaction. FIG. 6B demonstrates base stability of the product; the change in mobility shown in this figure corresponds to a loss of the 5' RNA sequence of 43-P (also termed "Met template") to produce the DNA-puromycin portion, termed 30-P. The retention of the label following base treatment was consistent with the formation of a peptide bond between $^{35}S$ methionine and the 3' puromycin of the template. FIG. 6C demonstrates the inhibition of product formation in the presence of peptidyl transferase inhibitors. FIG. 6D demonstrates the dependence of $^{35}$S methionine incorporation on a template coding sequence. FIG. 6E demonstrates DNA template length dependence of $^{35}$S methionine incorporation. FIG. 6F illustrates cis versus trans product formation using templates 43-P and 25-P. FIG. 6G illustrates cis versus trans product formation using templates 43-P and 13-P. FIG. 6H illustrates cis versus trans product formation using templates 43-P and 30-P in a reticulocyte lysate system.

FIG. 7A shows LP77 ("ligated-product," "77" nucleotides long) (also termed, "short myc template") (SEQ ID NO:1). This sequence contains the c-myc monoclonal antibody epitope tag EQKLISEEDL (SEQ ID NO:2) (Evan et al., Mol. Cell Biol. 5:3610–3616 (1985)) flanked by a 5' start codon and a 3' linker. The 5' region contains a bacterial Shine-Dalgarno sequence identical to that of 43-P. The coding sequence was optimized for translation in bacterial systems. In particular, the 5' UTRs of 43-P and LP77 contained a Shine-Dalgarno sequence complementary to five bases of 16S rRNA (Steitz and Jakes, Proc. Natl. Acad. Sci. USA 72:4734–4738 (1975)) and spaced similarly to ribosomal protein sequences (Stormo et al, Nucleic Acids Res. 10:2971–2996 (1982)). FIG. 7B shows LP154 (ligated product, 154 nucleotides long) (also termed "long myc template") (SEQ ID NO:3). This sequence contains the code for generation of the peptide used to isolate the c-myc antibody. The 5' end contains a truncated version of the TMV upstream sequence (designated "TE). This 5' UTR contained a 22 nucleotide sequence derived from the TMV 5' UTR encompassing two ACAAAUUAC direct repeats (Gallie et al., Nucl. Acids Res. 16:883 (1988)). FIG. 7C shows Pool #1 (SEQ ID NO:4), an exemplary sequence to be used for peptide selection. The final seven amino acids from the original myc peptide were included in the template to serve as the 3' constant region required for PCR amplification of the template. This sequence is known not to be part of the antibody binding epitope.

FIG. 15A shows incorporation of $^{35}$S using either no template (lane 1), a syn-β-globin template (lanes 2–4), or an LP-β-globin template (lanes 5–7). FIG. 15B (lanes labeled as in FIG. 15A) shows $^{35}$S-labeled material isolated by oligonucleotide affinity chromatography. No material was isolated in the absence of a 30-P tail (lanes 2–4).

FIG. 16A is a schematic of the selection protocol. Four mixtures of the myc and pool templates were translated in vitro and isolated on dT$_{25}$ agarose followed by TP sepharose to purify the template fusions from unmodified templates. The mRNA-peptide fusions were then reverse transcribed to suppress any secondary or tertiary structure present in the templates. Aliquots of each mixture were removed both before (FIG. 16B) and after (FIG. 16C) affinity selection, amplified by PCR in the presence of a labeled primer, and digested with a restriction enzyme that cleaved only the myc DNA. The input mixtures of templates were pure myc (lane 1), or a 1:20, 1:200, or 1:2000 myc:pool (lanes 2–4). The unselected material deviated from the input ratios due to preferential translation and reverse transcription of the myc template. The enrichment of the myc template during the selective step was calculated from the change in the pool:myc ratio before and after selection.

Figure 2:
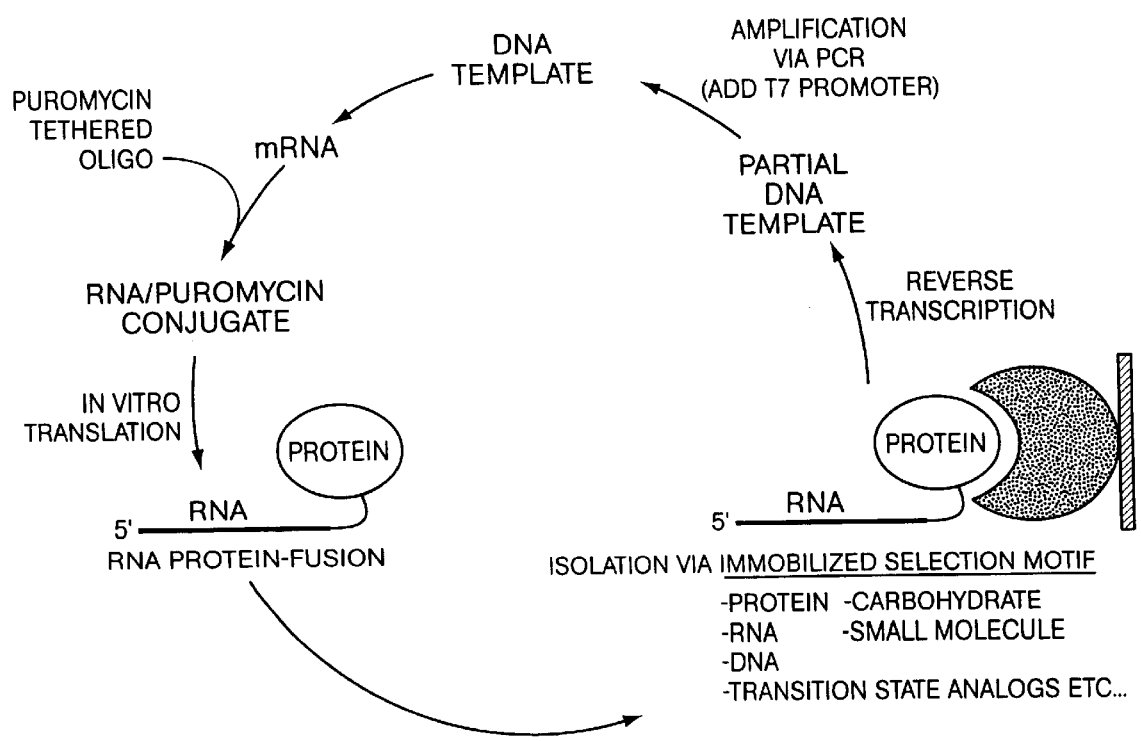
FIG. 2 is a schematic representation of a generalized selection protocol according to the invention.

Described herein is a general method for the selection of proteins with desired functions using fusions in which these proteins are covalently linked to their own messenger RNAs. These RNA-protein fusions are synthesized by in vitro or in situ translation of mRNA pools containing a peptide acceptor attached to their 3' ends (FIG. 1B). In one preferred embodiment, after readthrough of the open reading frame of the message, the ribosome pauses when it reaches the designed pause site, and the acceptor moiety occupies the ribosomal A site and accepts the nascent peptide chain from the peptidyl-tRNA in the P site to generate the RNA-protein fusion (FIG. 1C). The covalent link between the protein and the RNA (in the form of an amide bond between the 3' end of the mRNA and the C-terminus of the protein which it encodes) allows the genetic information in the protein to be recovered and amplified (e.g., by PCR) following selection by reverse transcription of the RNA. Once the fusion is generated, selection or enrichment is carried out based on the properties of the mRNA-protein fusion, or, alternatively, reverse transcription may be carried out using the mRNA template while it is attached to the protein to avoid any effect of the single-stranded RNA on the selection. When the mRNA-protein construct is used, selected fusions may be tested to determine which moiety (the protein, the RNA, or both) provides the desired function.

In one preferred embodiment, puromycin (which resembles tyrosyl adenosine) acts as the acceptor to attach the growing peptide to its mRNA. Puromycin is an antibiotic that acts by terminating peptide elongation. As a mimetic of aminoacyl-tRNA, it acts as a universal inhibitor of protein synthesis by binding the A site, accepting the growing peptide chain, and falling off the ribosome (at a $Kd=10^{-4}M$) (Traut and Monro, J. Mol. Biol. 10:63 (1964); Smith et al., J. Mol. Biol. 13:617 (1965)). One of the most attractive features of puromycin is the fact that it forms a stable amide bond to the growing peptide chain, thus allowing for more stable fusions than potential acceptors that form unstable ester linkages. In particular, the peptidyl-puromycin molecule contains a stable amide linkage between the peptide and the O-methyl tyrosine portion of the puromycin. The 0-methyl tyrosine is in turn linked by a stable amide bond to the 3'-amino group of the modified adenosine portion of puromycin.

Other possible choices for acceptors include tRNA-like structures at the 3' end of the mRNA, as well as other compounds that act in a manner similar to puromycin. Such compounds include, without limitation, any compound which possesses an amino acid linked to an adenine or an adenine-like compound, such as the amino acid nucleotides, phenylalanyl-adenosine (A-Phe), tyrosyl adenosine (A-Tyr), and alanyl adenosine (A-Ala), as well as amide-linked structures, such as phenylalanyl 3' deoxy 3' amino adenosine, alanyl 3' deoxy 3' amino adenosine, and tyrosyl 3' deoxy 3' amino adenosine; in any of these compounds, any of the naturally-occurring L-amino acids or their analogs may be utilized. In addition, a combined tRNA-like 3' structure-puromycin conjugate may also be used in the invention.

Shown in FIG. 2 is a preferred selection scheme according to the invention. The steps involved in this selection are generally carried out as follows.

Step 1. Preparation of the DNA template. As a step toward generating the RNA-protein fusions of the invention, the RNA portion of the fusion is synthesized. This may be accomplished by direct chemical RNA synthesis or, more commonly, is accomplished by transcribing an appropriate double-stranded DNA template.

Such DNA templates may be created by any standard technique (including any technique of recombinant DNA technology, chemical synthesis, or both). In principle, any method that allows production of one or more templates containing a known, random, randomized, or mutagenized sequence may be used for this purpose. In one particular approach, an oligonucleotide (for example, containing random bases) is synthesized and is amplified (for example, by PCR) prior to transcription. Chemical synthesis may also be used to produce a random cassette which is then inserted into the middle of a known protein coding sequence (see, for example, chapter 8.2, Ausubel et al., Current Protocols in Molecular Biology, John Wiley & Sons and Greene Publishing Company, 1994). This latter approach produces a high density of mutations around a specific site of interest in the protein.

An alternative to total randomization of a DNA template sequence is partial randomization, and a pool synthesized in this way is generally referred to as a "doped" pool. An example of this technique, performed on an RNA sequence, is described, for example, by Ekland et al. (Nucl. Acids Research 23:3231 (1995)). Partial randomization may be performed chemically by biasing the synthesis reactions such that each base addition reaction mixture contains an excess of one base and small amounts of each of the others; by careful control of the base concentrations, a desired mutation frequency may be achieved by this approach. Partially randomized pools may also be generated using error prone PCR techniques, for example, as described in Beaudry and Joyce (Science 257:635 (1992)) and Bartel and Szostak (Science 261:1411 (1993)).

Numerous methods are also available for generating a DNA construct beginning with a known sequence and then creating a mutagenized DNA pool. Examples of such techniques are described in Ausubel et al. (supra. chapter 8) and Sambrook et al. (Molecular Cloning: A Laboratory Manual, chapter 15, Cold Spring Harbor Press, New York, $2^{nd}$ ed. (1989)). Random sequences may also be generated by the "shuffling" technique outlined in Stemmer (Nature 370: 389 (1994)).

To optimize a selection scheme of the invention, the sequences and structures at the 5' and 3' ends of a template may also be altered. Preferably, this is carried out in two separate selections, each involving the insertion of random domains into the template proximal to the appropriate end, followed by selection. These selections may serve (i) to maximize the amount of fusion made (and thus to maximize the complexity of a library) or (ii) to provide optimized translation sequences. Further, the method may be generally applicable, combined with mutagenic PCR, to the optimization of translation templates both in the coding and non-coding regions.

Step 2. Generation of RNA. As noted above, the RNA portion of an RNA-protein fusion may be chemically synthesized using standard techniques of oligonucleotide synthesis. Alternatively, and particularly if longer RNA sequences are utilized, the RNA portion is generated by in vitro transcription of a DNA template. In one preferred approach, T7 polymerase is used to enzymatically generate the RNA strand. Other appropriate RNA polymerases for this use include, without limitation, the SP6, T3 and E. coli RNA polymerases (described, for example, in Ausubel et al. (supra, chapter 3). In addition, the synthesized RNA may be, in whole or in part, modified RNA. In one particular example, phosphorothioate RNA may be produced (for example, by T7 transcription) using modified ribonucleotides and standard techniques. Such modified RNA provides the advantage of being nuclease stable.

Step 3. Ligation of Puromycin to the Template. Next, puromycin (or any other appropriate peptide acceptor) is covalently bonded to the template sequence. This step may be accomplished using T4 RNA ligase to attach the puromycin directly to the RNA sequence, or preferably the puromycin may be attached by way of a DNA "splint" using T4 DNA ligase or any other enzyme which is capable of joining together two nucleotide sequences (see FIG. 1B) (see also, for example, Ausubel et al., supra, chapter 3, sections 14 and 15). tRNA synthetases may also be used to attach puromycin-like compounds to RNA. For example, phenylalanyl tRNA synthetase links phenylalanine to phenylalanyl-tRNA molecules containing a 3' amino group, generating RNA molecules with puromycin-like 3' ends (Fraser and Rich, Proc. Natl. Acad. Sci. USA 70:2671 (1973)). Other peptide acceptors which may be used include, without limitation, any compound which possesses an amino acid linked to an adenine or an adenine-like compound, such as the amino acid nucleotides, phenylalanyl-adenosine (A-Phe), tyrosyl adenosine (A-Tyr), and alanyl adenosine (A-Ala), as well as amide-linked structures, such as phenylalanyl 3' deoxy 3' amino adenosine, alanyl 3' deoxy 3' amino adenosine, and tyrosyl 3' deoxy 3' amino adenosine; in any of these compounds, any of the naturally-occurring L-amino acids or their analogs may be utilized. A number of peptide acceptors are described, for example, in Krayevsky and Kukhanova, Progress in Nucleic Acids Research and Molecular Biology 23:1 (1979).

Step 4. Generation and Recovery of RNA-Protein Fusions. To generate RNA-protein fusions, any in vitro or in situ translation system may be utilized. As shown below, eukaryotic systems are preferred, and two particularly preferred systems include the wheat germ and reticulocyte lysate systems. In principle, however, any translation system which allows formation of an RNA-protein fusion and which does not significantly degrade the RNA portion of the fusion is useful in the invention. In addition, to reduce RNA degradation in any of these systems, degradation-blocking antisense oligonucleotides may be included in the translation reaction mixture; such oligonucleotides specifically hybridize to and cover sequences within the RNA portion of the molecule that trigger degradation (see, for example, Hanes and Pluckthun, Proc. Natl. Acad. Sci USA 94:4937 (1997)).

As noted above, any number of eukaryotic translation systems are available for use in the invention. These include, without limitation, lysates from yeast, ascites, tumor cells (Leibowitz et al., Meth. Enzymol. 194:536 (1991)), and xenopus oocyte eggs. Useful in vitro translation systems from bacterial systems include, without limitation, those described in Zubay (Ann. Rev. Genet. 7:267 (1973)); Chen and Zubay (Meth. Enzymol. 101:44 (1983)); and Ellman (Meth. Enzymol. 202:301 (1991)).

In addition, translation reactions may be carried out in situ. In one particular example, translation may be carried out by injecting mRNA into Xenopus eggs using standard techniques.

Once generated, RNA-protein fusions may be recovered from the translation reaction mixture by any standard technique of protein or RNA purification. Typically, protein purification techniques are utilized. As shown below, for example, purification of a fusion may be facilitated by the use of suitable chromatographic reagents such as $dT_{25}$ agarose or thiopropyl sepharose. Purification, however, may also or alternatively involve purification based upon the RNA portion of the fusion; techniques for such purification are described, for example in Ausubel et al. (supra, chapter 4).

Step 5. Selection of the Desired RNA-Protein Fusion. Selection of a desired RNA-protein fusion may be accomplished by any means available to selectively partition or isolate a desired fusion from a population of candidate fusions. Examples of isolation techniques include, without limitation, selective binding, for example, to a binding partner which is directly or indirectly immobilized on a column, bead, membrane, or other solid support, and immunoprecipitation using an antibody specific for the protein moiety of the fusion. The first of these techniques makes use of an immobilized selection motif which can consist of any type of molecule to which binding is possible. A list of possible selection motif molecules is presented in FIG. 2. Selection may also be based upon the use of substrate molecules attached to an affinity label (for example, substrate-biotin) which react with a candidate molecule, or upon any other type of interaction with a fusion molecule. In addition, proteins may be selected based upon their catalytic activity in a manner analogous to that described by Bartel and Szostak for the isolation of RNA enzymes (supra); according to that particular technique, desired molecules are selected based upon their ability to link a target molecule to themselves, and the functional molecules are then isolated based upon the presence of that target. Selection schemes for isolating novel or improved catalytic proteins using this same approach or any other functional selection are enabled by the present invention.

In addition, as described herein, selection of a desired RNA-protein fusion (or its DNA copy) may be facilitated by enrichment for that fusion in a pool of candidate molecules. To carry out such an optional enrichment, a population of candidate RNA-protein fusions is contacted with a binding partner (for example, one of the binding partners described above) which is specific for either the RNA portion or the protein portion of the fusion, under conditions which substantially separate the binding partner-fusion complex from unbound members in the sample. This step may be repeated, and the technique preferably includes at least two sequential enrichment steps, one in which the fusions are selected using a binding partner specific for the RNA portion and another in which the fusions are selected using a binding partner specific for the protein portion. In addition, if enrichment steps targeting the same portion of the fusion (for example, the protein portion) are repeated, different binding partners are preferably utilized. In one particular example described herein, a population of molecules is enriched for desired fusions by first using a binding partner specific for the RNA portion of the fusion and then, in two sequential steps, using two different binding partners, both of which are specific for the protein portion of the fusion. Again, these complexes may be separated from sample components by any standard separation technique including, without limitation, column affinity chromatography, centrifugation, or immunoprecipitation.

Moreover, elution of an RNA-protein fusion from an enrichment (or selection) complex may be accomplished by a number of approaches. For example, as described herein, one may utilize a denaturing or non-specific chemical elution step to isolate a desired RNA-protein fusion. Such a step facilitates the release of complex components from each other or from an associated solid support in a relatively non-specific manner by breaking non-covalent bonds between the components and/or between the components and the solid support. As described herein, one exemplary denaturing or non-specific chemical elution reagent is 4% HOAc/$H_2O$. Other exemplary denaturing or non-specific chemical elution reagents include guanidine, urea, high salt, detergent, or any other means by which non-covalent adducts may generally be removed. Alternatively, one may utilize a specific chemical elution approach, in which a chemical is exploited that causes the specific release of a fusion molecule. In one particular example, if the linker arm of a desired fusion protein contains one or more disulfide bonds, bound fusion aptamers may be eluted by the addition, for example, of DTT, resulting in the reduction of the disulfide bond and release of the bound target.

Alternatively, elution may be accomplished by specifically disrupting affinity complexes; such techniques selectively release complex components by the addition of an excess of one member of the complex. For example, in an ATP-binding selection, elution is performed by the addition of excess ATP to the incubation mixture. Finally, one may carry out a step of enzymatic elution. By this approach, a bound molecule itself or an exogenously added protease (or other appropriate hydrolytic enzyme) cleaves and releases either the target or the enzyme. In one particular example, a protease target site may be included in either of the complex components, and the bound molecules eluted by addition of the protease. Alternately, in a catalytic selection, elution may be used as a selection step for isolating molecules capable of releasing (for example, cleaving) themselves from a solid support.

Step 6. Generation of a DNA Copy of the RNA Sequence using Reverse Transcriptase. If desired, a DNA copy of a selected RNA fusion sequence is readily available by reverse transcribing that RNA sequence using any standard technique (for example, using Superscript reverse transcriptase). This step may be carried out prior to the selection or enrichment step (for example, as described in FIG. 16), or following that step. Alternatively, the reverse transcription process may be carried out prior to the isolation of the fusion from the in vitro or in situ translation mixture.

Next, the DNA template is amplified, either as a partial or full-length double-stranded sequence. Preferably, in this step, full-length DNA templates are generated, using appropriate oligonucleotides and PCR amplification.

These steps, and the reagents and techniques for carrying out these steps, are now described in detail using particular examples. These examples are provided for the purpose of illustrating the invention, and should not be construed as limiting.

GENERATION OF TEMPLATES FOR RNA-PROTEIN FUSIONS

As shown in FIGS. 1A and 2, the selection scheme of the present invention preferably makes use of double-stranded DNA templates which include a number of design elements. The first of these elements is a promoter to be used in conjunction with a desired RNA polymerase for mRNA synthesis. As shown in FIG. 1A and described herein, the T7 promoter is preferred, although any promoter capable of directing synthesis from a linear double-stranded DNA may be used.

The second element of the template shown in FIG. 1A is termed the 5' untranslated region (or 5'UTR) and corresponds to the RNA upstream of the translation start site. Shown in FIG. 1A is a preferred 5'UTR (termed "TE") which is a deletion mutant of the Tobacco Mosaic Virus 5' untranslated region and, in particular, corresponds to the bases directly 5' of the TMV translation start; the sequence of this UTR is as follows: rGrGrG rArCrA rArUrU rArCrU rArUrU rUrAtC rArArU rUrArC rA (with the first 3 G nucleotides being inserted to augment transcription) (SEQ ID NO: 5). Any other appropriate 5' UTR may be utilized (see, for example, Kozak, Microbiol. Rev. 47:1 (1983)).

The third element shown in FIG. 1A is the translation start site. In general, this is an AUG codon. However, there are examples where codons other than AUG are utilized in naturally-occurring coding sequences, and these codons may also be used in the selection scheme of the invention.

The fourth element in FIG. 1A is the open reading frame of the protein (termed ORF), which encodes the protein sequence. This open reading frame may encode any naturally-occurring, random, randomized, mutagenized, or totally synthetic protein sequence.

The fifth element shown in FIG. 1A is the 3' constant region. This sequence facilitates PCR amplification of the pool sequences and ligation of the puromycin-containing oligonucleotide to the mRNA. If desired, this region may also include a pause site, a sequence which causes the ribosome to pause and thereby allows additional time for an acceptor moiety (for example, puromycin) to accept a nascent peptide chain from the peptidyl-tRNA; this pause site is discussed in more detail below.

To develop the present methodology, RNA-protein fusions were initially generated using highly simplified mRNA templates containing 1–2 codons. This approach was taken for two reasons. First, templates of this size could readily be made by chemical synthesis. And, second, a small open reading frame allowed critical features of the reaction, including efficiency of linkage, end heterogeneity, template dependence, and accuracy of translation, to be readily assayed.

Design of Construct. A basic construct was used for generating test RNA-protein fusions. The molecule consisted of a mRNA containing a Shine-Dalgamo (SD) sequence for translation initiation which contained a 3 base deletion of the SD sequence from ribosomal protein L1 and which was complementary to 5 bases of 16S rRNA (i.e., rGrGrA rGrGrA rCrGrA rA) (SEQ ID NO: 6) (Stormo et al., Nucleic Acids Research 10:2971–2996 (1982); Shine and Dalgamo, Proc. Natl. Acad. Sci. USA 71:1342–1346 (1974); and Steitz and Jakes, Proc. Natl. Acad. Sci. USA 72:4734–4738 (1975)), (ii) an AUG start codon, (iii) a DNA linker to act as a pause site (i.e., 5'-(dA)$_{27}$), (iv) dCdC-3', and (v) a 3' puromycin (P). The poly dA sequence was chosen because it was known to template tRNA poorly in the A site (Morgan et al., J. Mol. Biol. 26:477–497 (1967); Ricker and Kaji, Nucleic Acid Research 19:6573-6578 (1991)) and was designed to act as a good pause site. The length of the oligo dA linker was chosen to span the ~60–70 Å distance between the decoding site and the peptidyl transfer center of the ribosome. The dCdCP mimicked the CCA end of a tRNA and was designed to facilitate binding of the puromycin to the A site of the ribosome.

Figure 3:
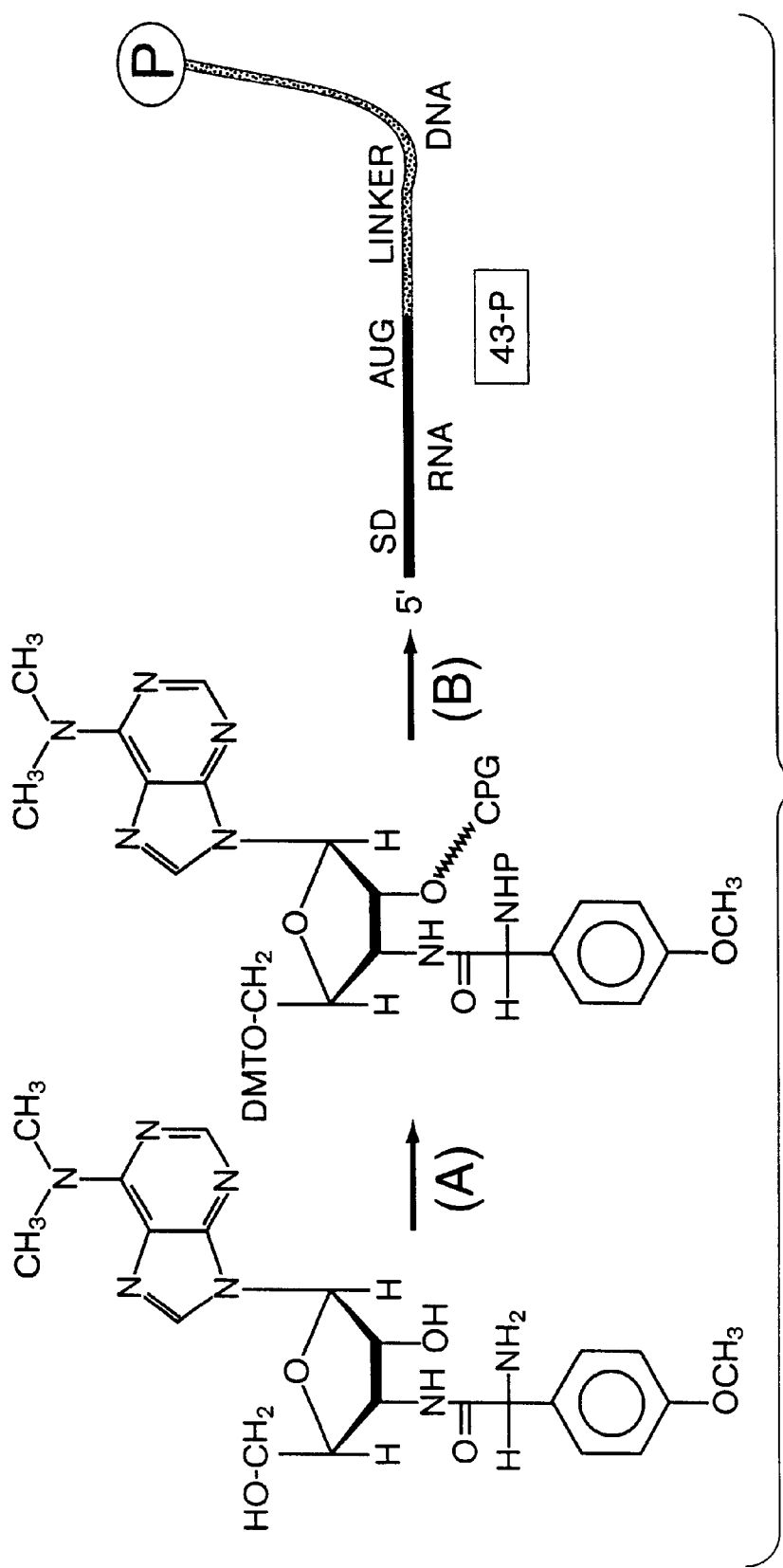
FIG. 3 is a schematic representation of a synthesis protocol for minimal translation templates containing 3' puromycin. Step (A) shows the addition of protective groups to the reactive functional groups on puromycin (5'-OH and $NH_2$); as modified, these groups are suitably protected for use in phosphoramidite based oligonucleotide synthesis. The protected puromycin was attached to aminohexyl controlled pore glass (CPG) through the 2'OH group using the standard protocol for attachment of DNA through its 3'OH (Gait, Oligonucleotide Synthesis, A Practical Approach, The Practical Approach Series (IRL Press, Oxford, 1984)). In step (B), a minimal translation template (termed "43-P"), which contained 43 nucleotides, was synthesized using standard RNA and DNA chemistry (Millipore, Bedford, Mass.), deprotected using $NH_4OH$ and TBAF, and gel purified. The template contained 13 bases of RNA at the 5' end followed by 29 bases of DNA attached to the 3' puromycin at its 5' OH. The RNA sequence contained (i) a Shine-Dalgarno consensus sequence complementary to five bases of 16S rRNA (Stormo et al., Nucleic Acids Research 10:2971–2996 (1982); Shine and Dalgarno, Proc. Natl. Acad. Sci. USA 71:1342–1346 (1974); and Steitz and Jakes, Proc. Natl. Acad. Sci. USA 72:4734–4738 (1975)), (ii) a five base spacer, and (iii) a single AUG start codon. The DNA sequence was $dA_{27}dCdCP$, where "P" is puromycin.

Chemical Synthesis of Minimal Template 43-P. To synthesize construct 43-P (shown in FIG. 3), puromycin was first attached to a solid support in such a way that it would be compatible with standard phosphoramidite oligonucleotide synthesis chemistry. The synthesis protocol for this oligo is outlined schematically in FIG. 3 and is described in more detail below. To attach puromycin to a controlled pore glass (CPG) solid support, the amino group was protected with a trifluoroacetyl group as described in Applied Biosystems User Bulletin #49 for DNA synthesizer model 380 (1988). Next, protection of the 5' OH was carried out using a standard DMT-Cl approach (Gait, Oligonucleotide Synthesis a practical approach The Practical Approach Series (IRL Press, Oxford, 1984)), and attachment to aminohexyl CPG through the 2' OH was effected in exactly the same fashion as the 3' OH would be used for attachment of a deoxynucleoside (see FIG. 3 and Gait, supra, p. 47). The 5' DMT-CPG-linked protected puromycin was then suitable for chain extension with phosphoramidite monomers. The synthesis of the oligo proceeded in the 3'→5' direction in the order: (i) 3' puromycin, (ii) pdCpdC, (iii) ~27 units of dA as a linker, (iv) AUG, and (v) the Shine-Dalgarno sequence. The sequence of the 43-P construct is shown below.

Synthesis of CPG Puromycin. The synthesis of protected CPG puromycin followed the general path used for deoxynucleosides as previously outlined (Gait, Oligonucleotide Synthesis, A Practical Approach, The Practical Approach Series (IRL Press, Oxford, 1984)). Major departures included the selection of an appropriate N blocking group, attachment at the 2' OH to the solid support, and the linkage reaction to the solid support. In the case of the latter, the reaction was carried out at very low concentrations of activated nucleotide as this material was significantly more precious than the solid support. The resulting yield (~20 $\mu$mol/g support) was quite satisfactory considering the dilute reaction conditions.

Figure 4:
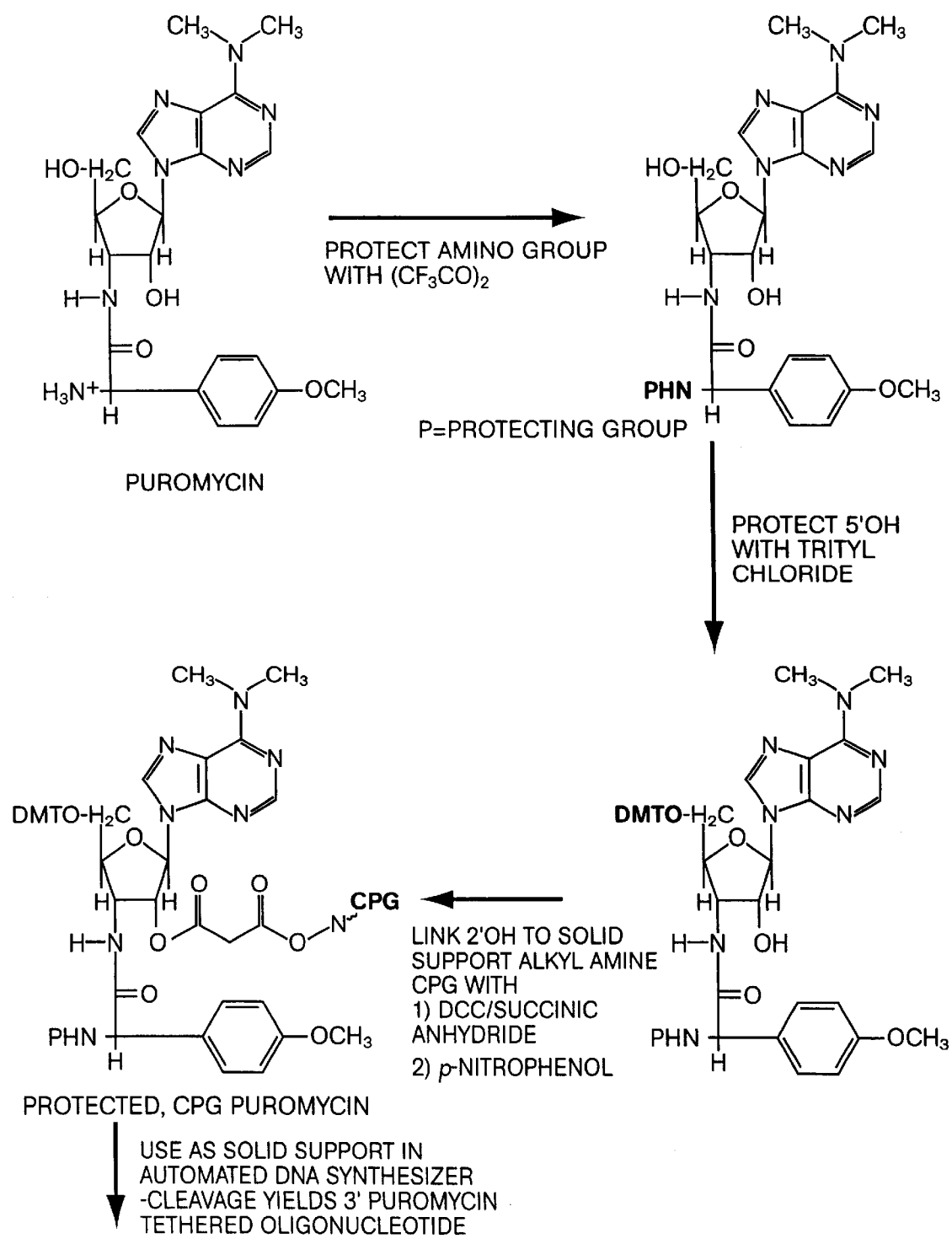
FIG. 4 is a schematic representation of a preferred method for the preparation of protected CPG-linked puromycin.

Synthesis of N-Trifluoroacetyl Puromycin. 267 mg (0.490 mmol) Puromycin*HCl was first converted to the free base form by dissolving in water, adding pH 11 carbonate buffer, and extracting (3X) into chloroform. The organic phase was evaporated to dryness and weighed (242 mg, 0.513 mmol). The free base was then dissolved in 11 ml dry pyridine and 11 ml dry acetonitrile, and 139 $\mu$L (2.0 mmol) triethylamine (TEA) and 139 $\mu$l (1.0 mmol) of trifluoroacetic anhydride (TFAA) were added with stirring. TFAA was then added to the turbid solution in 20 $\mu$l aliquots until none of the starting material remained, as assayed by thin layer chromatography (tlc) (93:7, Chloroform/MeOH) (a total of 280 $\mu$l). The reaction was allowed to proceed for one hour. At this point, two bands were revealed by thin layer chromatography, both of higher mobility than the starting material. Workup of the reaction with NH$_4$OH and water reduced the product to a single band. Silica chromatography (93:7 Chloroform/MeOH) yielded 293 mg (0.515 mmol) of the product, N-TFA-Pur. The product of this reaction is shown schematically in FIG. 4.

Synthesis of N-Trifluoroacetyl 5'-DMT Puromycin. The product from the above reaction was aliquoted and coevaporated 2X with dry pyridine to remove water. Multiple tubes were prepared to test multiple reaction conditions. In a small scale reaction, 27.4 mg (48.2 $\mu$moles) N-TFA-Pur were dissolved in 480 $\mu$l of pyridine containing 0.05 eq of DMAP and 1.4 eq TEA. To this mixture, 20.6 mg of trityl chloride (60 $\mu$mol) was added, and the reaction was allowed to proceed to completion with stirring. The reaction was stopped by addition of an equal volume of water (approximately 500 $\mu$l) to the solution. Because this reaction appeared successfull, a large scale version was performed. In particular, 262 mg (0.467 mmol) N-TFA-Pur was dissolved in 2.4 ml pyridine followed by addition of 1.4 eq of TEA, 0.05 eq of DMAP, and 1.2 eq of trityl chloride. After approximately two hours, an additional 50 mg (0.3 eq) dimethoxytrityl*Cl (DMT*Cl) was added, and the reaction was allowed to proceed for 20 additional minutes. The reaction was stopped by the addition of 3 ml of water and coevaporated 3X with CH$_3$CN. The reaction was purified by 95:5 Chloroform/MeOH on a 100 ml silica (dry) 2 mm diameter column. Due to incomplete purification, a second identical column was run with 97.5:2.5 Chloroform/MeOH. The total yield was 325 mg or 0.373 mmol (or a yield of 72%). The product of this reaction is shown schematically in FIG. 4.

Synthesis of N-Trifluoroacetyl. 5'-DMT. 2' Succinyl Puromycin. In a small scale reaction, 32 mg (37 $\mu$mol) of the product synthesized above was combined with 1.2 eq of DMAP dissolved in 350 $\mu$l of pyridine. To this solution, 1.2 equivalents of succinic anhydride was added in 44 $\mu$l of dry CH$_3$CN and allowed to stir overnight. Thin layer chromatography revealed little of the starting material remaining. In a large scale reaction, 292 mg (336 $\mu$mol) of the previous product was combined with 1.2 eq DMAP in 3 ml of pyridine. To this, 403 $\mu$l of 1M succinic anhydride in dry CH$_3$CN was added, and the mixture was allowed to stir overnight. Thin layer chromatography again revealed little of the starting material remaining. The two reactions were combined, and an additional 0.2 eq of DMAP and succinate were added. The product was coevaporated with toluene 1X and dried to a yellow foam in high vacuum. CH$_2$Cl$_2$ was added (20 ml), and this solution was extracted twice with 15 ml of 10% ice cold citric acid and then twice with pure water. The product was dried, redissolved in 2 ml of CH$_2$Cl$_2$, and precipitated by addition of 50 ml of hexane with stirring. The product was then vortexed and centrifuged at 600 rpm for 10 minutes in the clinical centrifuge. The majority of the eluent was drawn off, and the rest of the product was dried, first at low vacuum, then at high vacuum in a dessicator. The yield of this reaction was approximately 260 $\mu$mol for a stepwise yield of 70%.

Synthesis of N-Trifluoroacetyl 5'-DMT. 2' Succinyl. CPG Puromycin. The product from the previous step was next dissolved with 1 ml of dioxane followed by 0.2 ml dioxane/0.2 ml pyridine. To this solution, 40 mg of p-nitrophenol and 140 mg of dicyclohexylcarbodiimide (DCC) was added, and the reaction was allowed to proceed for 2 hours. The insoluble cyclohexyl urea produced by the reaction was removed by centrifugation, and the product solution was added to 5 g of aminohexyl controlled pore glass (CPG) suspended in 22 ml of dry DMF and stirred overnight. The resin was then washed with DMF, methanol, and ether, and dried. The resulting resin was assayed as containing 22.6 μmol of trityl per g, well within the acceptable range for this type of support. The support was then capped by incubation with 15 ml of pyridine, 1 ml of acetic anhydride, and 60 mg of DMAP for 30 minutes. The resulting column material produced a negative (no color) ninhydrin test, in contrast to the results obtained before blocking in which the material produced a dark blue color reaction. The product of this reaction is shown schematically in FIG. 4.

Synthesis of mRNA-Puromycin Conjugate. As discussed above, a puromycin tethered oligo may be used in either of two ways to generate a mRNA-puromycin conjugate which acts as a translation template. For extremely short open reading frames, the puromycin oligo is typically extended chemically with RNA or DNA monomers to create a totally synthetic template. When longer open reading frames are desired, the RNA or DNA oligo is generally ligated to the 3' end of an mRNA using a DNA splint and T4 DNA ligase as described by Moore and Sharp (Science 256:992 (1992)).

IN VITRO TRANSLATION AND TESTING OF RNA-PROTEIN FUSIONS

The templates generated above were translated in vitro using both bacterial and eukaryotic in vitro translation systems as follows.

In Vitro Translation of Minimal Templates. 43-P and related RNA-puromycin conjugates were added to several different in vitro translation systems including: (i) the S30 system derived from *E. coli* MRE600 (Zubay, Ann. Rev. Genet. 7:267 (1973); Collins, Gene 6:29 (1979); Chen and Zubay, Methods Enzymol, 101:44 (1983); Pratt, in Transcription and Translation: A Practical Approach, B. D. Hammes, S. J. Higgins, Eds. (IRL Press, Oxford, 1984) pp. 179–209; and Ellman et al., Methods Enzymol. 202:301 (1991)) prepared as described by Ellman et. al. (Methods Enzymol. 202:301 (1991)); (ii) the ribosomal fraction derived from the same strain, prepared as described by Kudlicki et al. (Anal. Chem. 206:389 (1992)); and (iii) the S30 system derived from *E. coli* BL21, prepared as described by Lesley et al. (J. Biol. Chem. 266:2632 (1991)). In each case, the premix used was that of Lesley et al. (J. Biol. Chem. 266:2632 (1991)), and the incubations were 30 minutes in duration.

Figure 5:
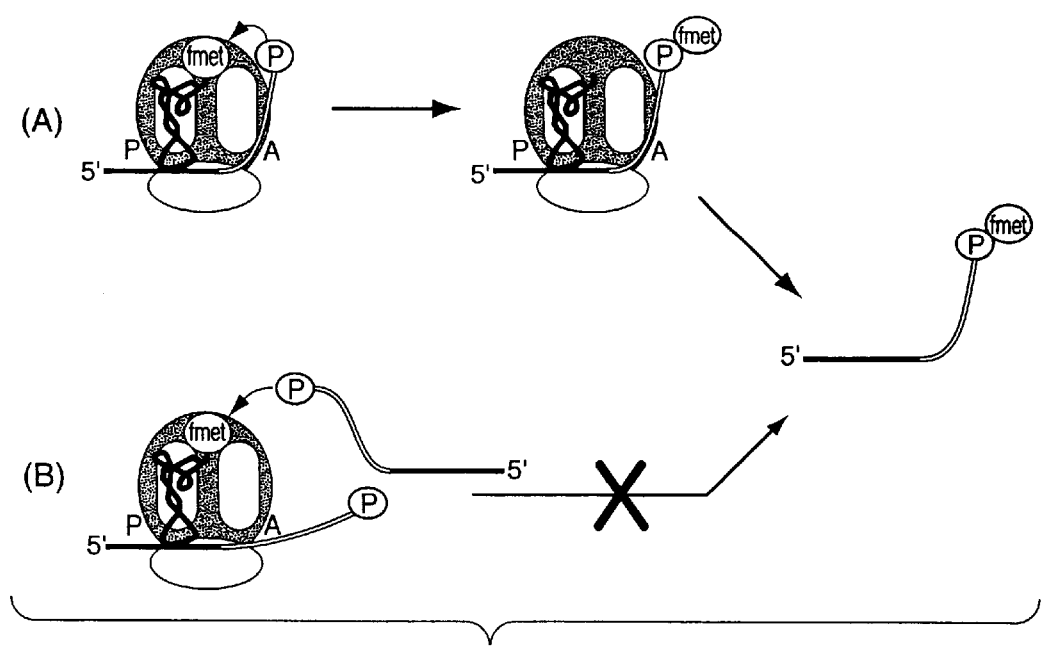
FIG. 5 is a schematic representation showing possible modes of methionine incorporation into a template of the invention. As shown in reaction (A), the template binds the ribosome, allowing formation of the 70S initiation complex. Fmet tRNA binds to the P site and is base paired to the template. The puromycin at the 3' end of the template enters the A site in an intramolecular fashion and forms an amide linkage to N-formyl methionine via the peptidyl transferase center, thereby deacylating the tRNA. Phenol/chloroform extraction of the reaction yields the template with methionine covalently attached. Shown in reaction (B) is an undesired intermolecular reaction of the template with puromycin containing oligonucleotides. As before, the minimal template stimulates formation of the 70S ribosome containing fmet tRNA bound to the P site. This is followed by entry of a second template in trans to give a covalently attached methionine.

Testing the Nature of the Fusion. The 43-P template was first tested using S30 translation extracts from *E. coli*. FIG. 5 (Reaction "A") demonstrates the desired intramolecular (cis) reaction wherein 43-P binds the ribosome and acts as a template for and an acceptor of fMet at the same time. The incorporation of $^{35}$S-methionine and its position in the template was first tested, and the results are shown in FIGS. 6A and 6B. After extraction of the in vitro translation reaction mixture with phenol/chloroform and analysis of the products by SDS-PAGE, an $^{35}$S labeled band appeared with the same mobility as the 43-P template. The amount of this material synthesized was dependent upon the $Mg^{2+}$ concentration (FIG. 6A). The optimum $Mg^{2+}$ concentration appeared to be between 9 and 18 mM, which was similar to the optimum for translation in this system (Zubay, Ann. Rev. Genet. 7:267 (1973); Collins, Gene 6:29 (1979); Chen and Zubay, Methods Enzymol, 101:44 (1983); Pratt, in Transcription and Translation: A Practical Approach, B. D. Hammes, S. J. Higgins, Eds. (IRL Press, Oxford, 1984) pp. 179–209; Elhman et al., Methods Enzymol. 202:301 (1991); Kudlicki et al., Anal. Chem. 206:389 (1992); and Lesley et al., J. Biol. Chem. 266:2632 (1991)). Furthermore, the incorporated label was stable to treatment with $NH_4OH$ (FIG. 6B), indicating that the label was located on the 3' half of the molecule (the base-stable DNA portion) and was attached by a base-stable linkage, as expected for an amide bond between puromycin and fMet.

Ribosome and Template Dependence. To demonstrate that the reaction observed above occurred on the ribosome, the effects of specific inhibitors of the peptidyl transferase function of the ribosome were tested (FIG. 6C), and the effect of changing the sequence coding for methionine was examined (FIG. 6D). FIG. 6C demonstrates clearly that the reaction was strongly inhibited by the peptidyl transferase inhibitors, virginiamycin, gougerotin, and chloramphenicol (Monro and Vazquez, J. Mol. Biol. 28:161–165 (1967); and Vazquez and Monro, Biochemica et Biophysical Acta 142:155–173 (1967)). FIG. 6D demonstrates that changing a single base in the template from A to C abolished incorporation of $^{35}$S methionine at 9 mM $Mg^{2+}$, and greatly decreased it at 18 mM (consistent with the fact that high levels of $Mg^{2+}$ allow misreading of the message). These experiments demonstrated that the reaction occurred on the ribosome in a template dependent fashion.

Figure 6E:
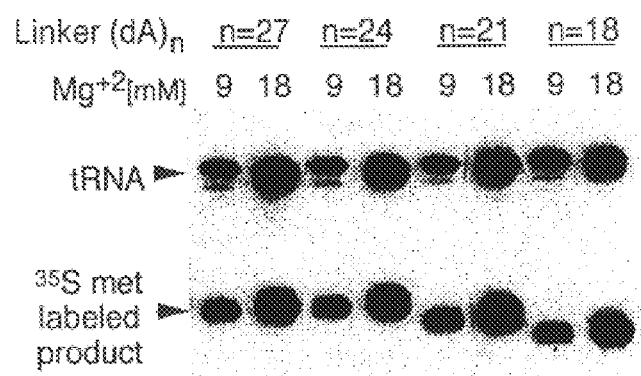

Linker Length. Also tested was the dependence of the reaction on the length of the linker (FIG. 6E). The original template was designed so that the linker spanned the distance from the decoding site (occupied by the AUG of the template) to the acceptor site (occupied by the puromycin moiety), a distance which was approximately the same length as the distance between the anticodon loop and the acceptor stem in a tRNA, or about 60–70 Å. The first linker tested was 30 nucleotides in length, based upon a minimum of 3.4 Å per base (>102 Å). In the range between 30 and 21 nucleotides (n 27–18; length >102–71 Å), little change was seen in the efficiency of the reaction. Accordingly, linker length may be varied. While a linker of between 21 and 30 nucleotides represents a preferred length, linkers shorter than 80 nucleotides and, preferably, shorter than 45 nucleotides may also be utilized in the invention.

Figures 6F, 6G, 6H:
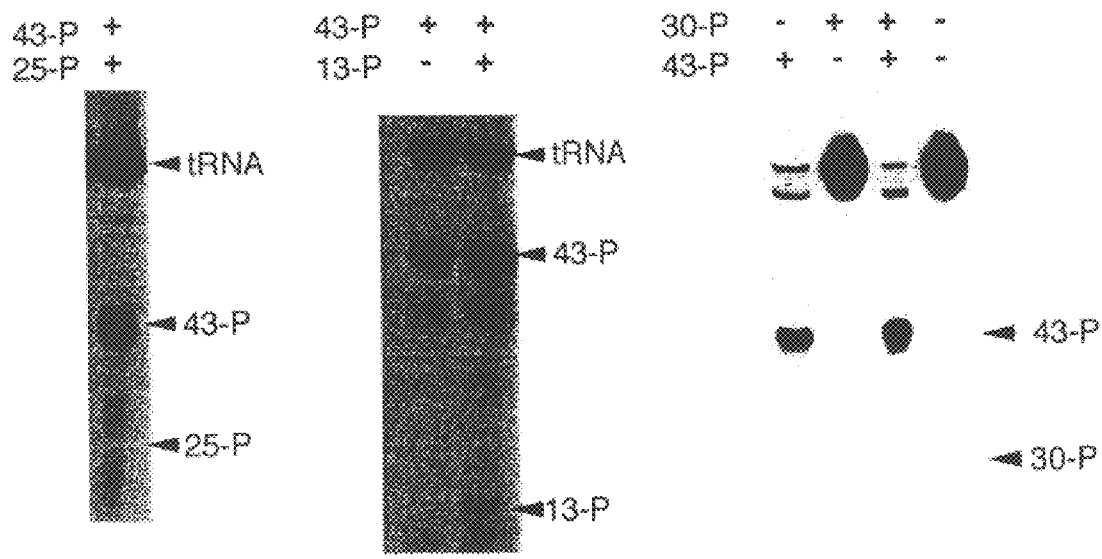

Intramolecular vs. Intermolecular Reactions. Finally, we tested whether the reaction occurred in an intramolecular fashion (FIG. 5, Reaction "A") as desired or intermolecularly (FIG. 5, Reaction "B"). This was tested by adding oligonucleotides with 3' puromycin but no ribosome binding sequence (i.e., templates 25-P, 13-P, and 30-P) to the translation reactions containing the 43-P template (FIGS. 6F, 6G, and 6H). If the reaction occurred by an intermolecular mechanism, the shorter oligos would also be labeled. As demonstrated in FIGS. 6F–H, there was little incorporation of $^{35}$S methionine in the three shorter oligos, indicating that the reaction occurred primarily in an intramolecular fashion. The sequences of 25-P (SEQ ID NO:10), 13-P (SEQ ID NO:9), and 30-P (SEQ ID NO:8) are shown below.

Reticulocyte Lysate. FIG. 6H demonstrates that $^{35}$S-methionine may be incorporated in the 43-P template using a rabbit reticulocyte lysate (see below) for in vitro translation, in addition to the *E. coli* lysates used above. This reaction occurred primarily in an intramolecular mechanism, as desired.

SYNTHESIS AND TESTING OF FUSIONS CONTAINING A C-MYC EPITOPE TAG

Exemplary fusions were also generated which contained, within the protein portion, the epitope tag for the c-myc monoclonal antibody 9E10 (Evan et al., Mol. Cell Biol. 5:3610 (1985)).

Figure 7A:
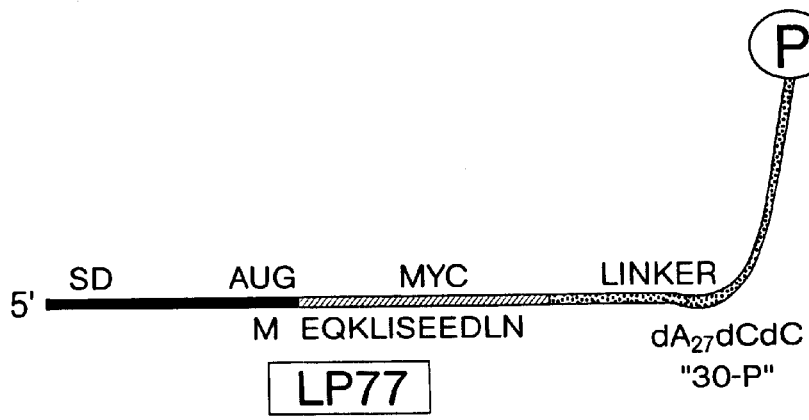
FIGS. 7A–7C are schematic illustrations of constructs for testing peptide fusion formation and selection.
Figure 7B:
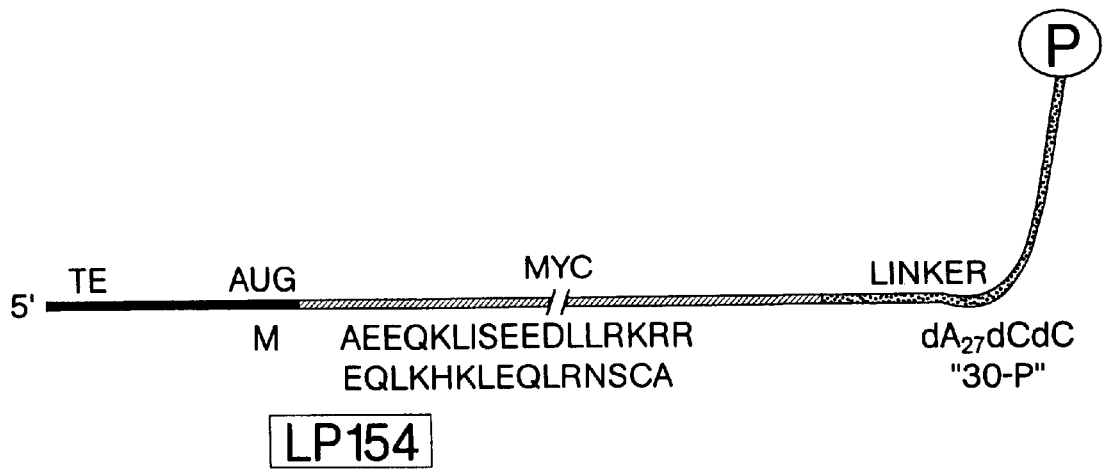
Figure 7C:
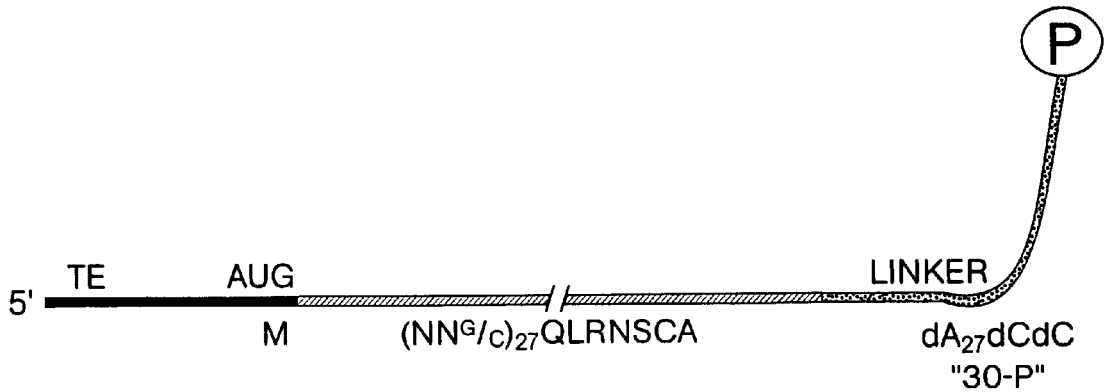

Design of Templates. Three initial epitope tag templates (i.e., LP77, LP154, and Pool #1) were designed and are shown in FIGS. 7A-C. The first two templates contained the c-myc epitope tag sequence EQKLISEEDL (SEQ ID NO:2), and the third template was the design used in the synthesis of a random selection pool. LP77 encoded a 12 amino acid sequence, with the codons optimized for bacterial translation. LP154 and its derivatives contained a 33 amino acid mRNA sequence in which the codons were optimized for eukaryotic translation. The encoded amino acid sequence of MAEEQKLISEEDLLRKRREQKLKHKLEQLRNSCA (SEQ ID NO:7) corresponded to the original peptide used to isolate the 9E10 antibody. Pool#1 contained 27 codons of NNG/C (to generate random peptides) followed by a sequence corresponding to the last seven amino acids of the myc peptide (which were not part of the myc epitope sequence). These sequences are shown below.

Figure 8:
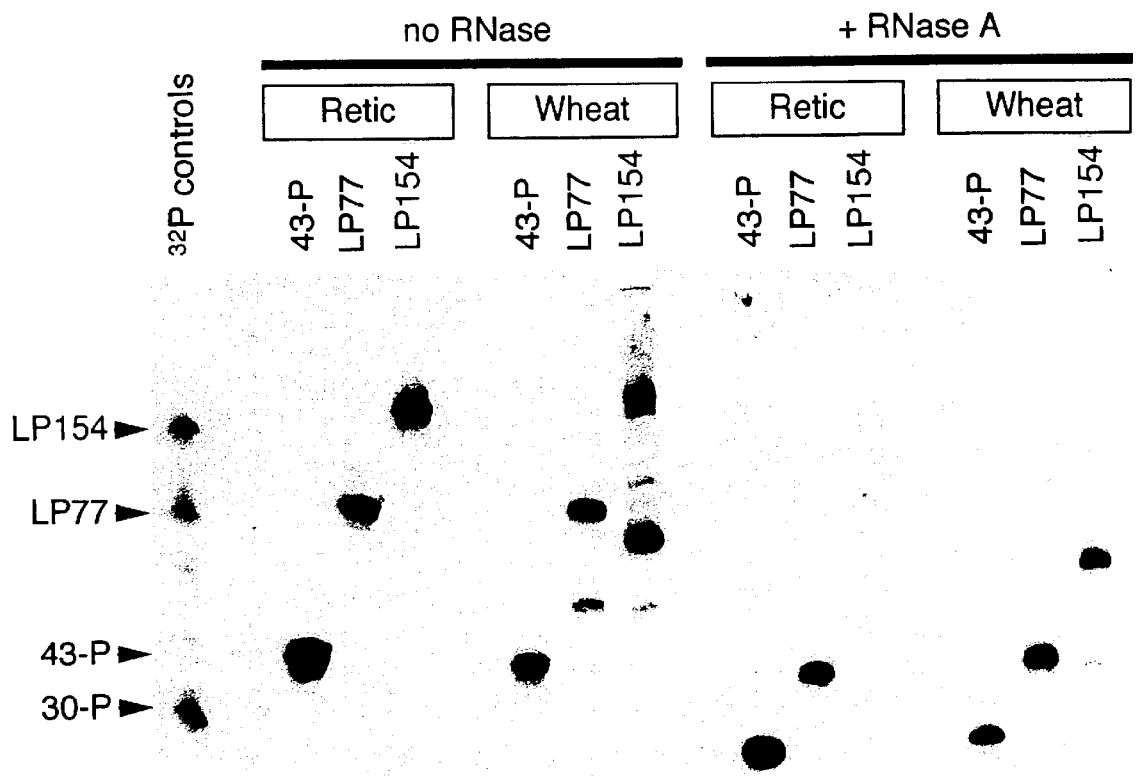
FIG. 8 is a photograph demonstrating the synthesis of RNA-protein fusions using templates 43-P, LP77, and LP154, and reticulocyte ("Retic") and wheat germ ("Wheat") translation systems. The left half of the figure illustrates $^{35}$S methionine incorporation in each of the three templates. The right half of the figure illustrates the resulting products after RNase A treatment of each of the three templates to remove the RNA coding region; shown are 35S methionine-labeled DNA-protein fusions. The DNA portion of each was identical to the oligo 30-P. Thus, differences in mobility were proportional to the length of the coding regions, consistent with the existence of proteins of different length in each case.

Reticulocyte vs. Wheat Germ In Vitro Translation Systems. The 43-P, LP77, and LP 154 templates were tested in both rabbit reticulocyte and wheat germ extract (Promega, Boehringer Mannheim) translation systems (FIG. 8). Translations were performed at 30° C. for 60 minutes. Templates were isolated using $dT_{25}$ agarose at 4° C. Templates were eluted from the agarose using 15 mM NaOH, 1 mM EDTA, neutralized with NaOAc/HOAc buffer, immediately ethanol precipitated (2.5–3 vol), washed (with 100% ethanol), and dried on a speedvac concentrator. FIG. 8 shows that $^{35}$S methionine was incorporated into all three templates, in both the wheat germ and reticulocyte systems. Less degradation of the template was observed in the fusion reactions from the reticulocyte system and, accordingly, this system is preferred for the generation of RNA-protein fusions. In addition, in general, eukaryotic systems are preferred over bacterial systems. Because eukaryotic cells tend to contain lower levels of nucleases, mRNA lifetimes are generally 10–100 times longer in these cells than in bacterial cells. In experiments using one particular E. coli translation system, generation of fusions was not observed using a template encoding the c-myc epitope; labeling the template in various places demonstrated that this was likely due to degradation of both the RNA and DNA portions of the template.

Figure 9:
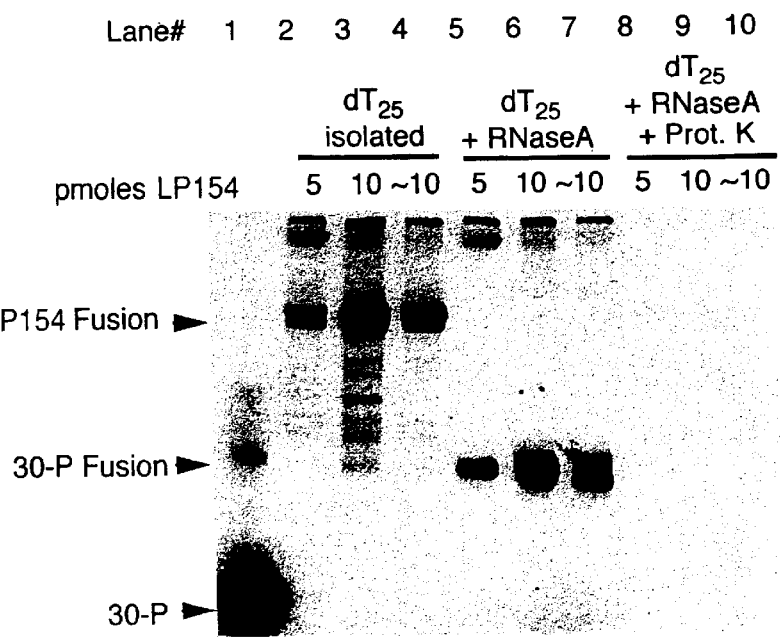
FIG. 9 is a photograph demonstrating protease sensitivity of an RNA-protein fusion synthesized from LP154 and analyzed by denaturing polyacrylamide gel electrophoresis. Lane 1 contains $^{32}$P labeled 30-P. Lanes 2–4, 5–7, and 8–10 contain the $^{35}$S labeled translation templates recovered from reticulocyte lysate reactions either without treatment, with RNase A treatment, or with RNase A and proteinase K treatment, respectively.

To examine the peptide portion of these fusions, samples were treated with RNase to remove the coding sequences. Following this treatment, the 43-P product ran with almost identical mobility to the $^{32}$P labeled 30-P oligo, consistent with a very small peptide (perhaps only methionine) added to 30-P. For LP77, removal of the coding sequence produced a product with lower mobility than the 30-P oligo, consistent with the notion that a 12 amino acid peptide was added to the puromycin. Finally, for LP154, removal of the coding sequence produced a product of yet lower mobility, consistent with a 33 amino acid sequence attached to the 30-P oligo. No oligo was seen in the RNase-treated LP154 reticulocyte lane due to a loading error. In FIG. 9, the mobility of this product was shown to be the same as the product generated in the wheat germ extract. In sum, these results indicated that RNase resistant products were added to the ends of the 30-P oligos, that the sizes of the products were proportional to the length of the coding sequences, and that the products were quite homogeneous in size. In addition, although both systems produced similar fusion products, the reticulocyte system appeared superior due to higher template stability.

Sensitivity to RNase A and Proteinase K. In FIG. 9, sensitivity to RNase A and proteinase K were tested using the LP154 fusion. As shown in lanes 2–4, incorporation of $^{35}$S methionine was demonstrated for the LP154 template. When this product was treated with RNase A, the mobility of the fusion decreased, but was still significantly higher than the $^{32}$P labeled 30-P oligonucleotide, consistent with the addition of a 33 amino acid peptide to the 3' end. When this material was also treated with proteinase K, the $^{35}$S signal completely disappeared, again consistent with the notion that the label was present in a peptide at the 3' end of the 30-P fragment. Similar results have been obtained in equivalent experiments using the 43-P and LP77 fusions.

To confirm that the template labeling by $^{35}$S Met was a consequence of translation, and more specifically resulted from the peptidyl transferase activity of the ribosome, the effect of various inhibitors on the labeling reaction was examined. The specific inhibitors of eukaryotic peptidyl transferase, anisomycin, gougerotin, and sparsomycin (Vazquez, *Inhibitors of Protein Biosynthesis* (Springer-Verlag, New York), pp. 312 (1979)), as well as the translocation inhibitors cycloheximide and emetine (Vazquez, *Inhibitors of Protein Biosynthesis* (Springer-Verlag, New York), pp. 312 (1979)) all decreased RNA-peptide fusion formation by ~95% using the long myc template and a reticulocyte lysate translation extract.

Figure 10:
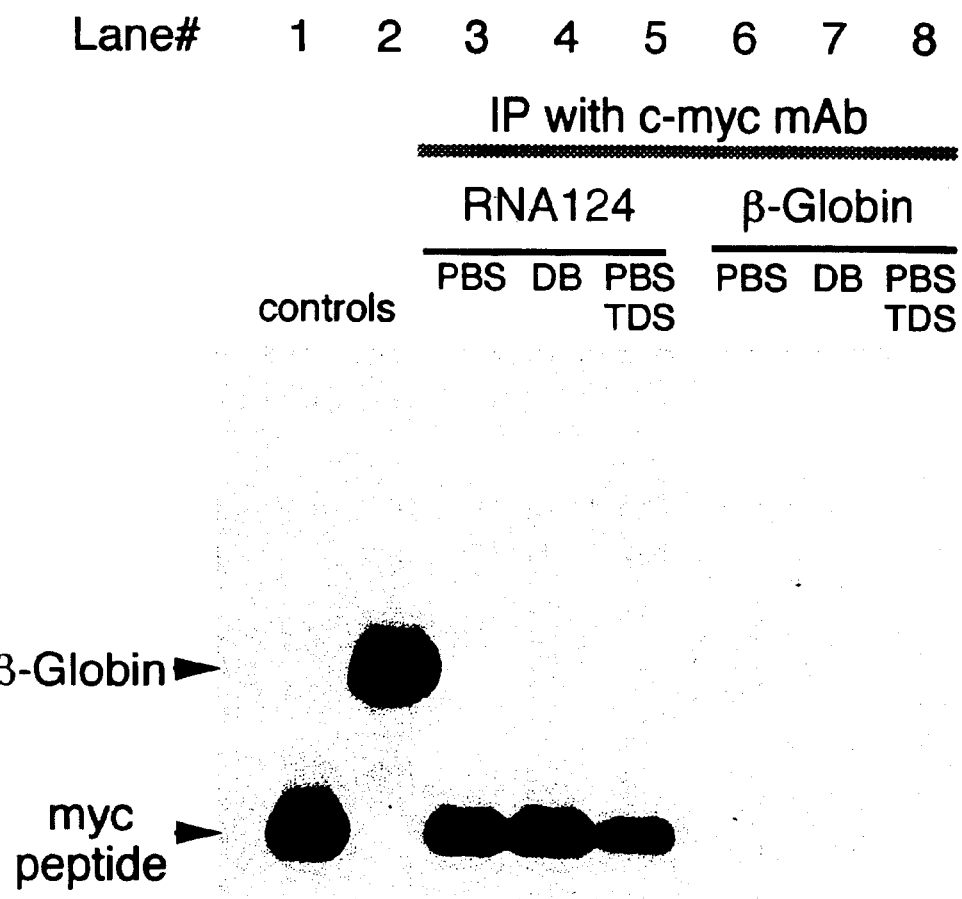
FIG. 10 is a photograph showing the results of immunoprecipitation reactions using in vitro translated 33 amino acid myc-epitope protein. Lanes 1 and 2 show the translation products of the myc epitope protein and β-globin templates, respectively. Lanes 3–5 show the results of immunoprecipitation of the myc-epitope peptide using a c-myc monoclonal antibody and PBS, DB, and PBSTDS wash buffers, respectively. Lanes 6–8 show the same immunoprecipitation reactions, but using the β-globin translation product.

Immunoprecipitation Experiments. In an experiment designed to illustrate the efficacy of immunoprecipitating an mRNA-peptide fusion, an attempt was made to immunoprecipitate a free c-myc peptide generated by in vitro translation. FIG. 10 shows the results of these experiments assayed on an SDS PAGE peptide gel. Lanes 1 and 2 show the labeled material from translation reactions containing either RNA124 (the RNA portion of LP154) or β-globin mRNA. Lanes 3–8 show the immunoprecipitation of these reaction samples using the c-myc monoclonal antibody 9E10, under several different buffer conditions (described below). Lanes 3–5 show that the peptide derived from RNA124 was effectively immunoprecipitated, with the best case being lane 4 where ~83% of the total TCA precipitable counts were isolated. Lanes 6–8 show little of the β-globin protein, indicating a purification of >100 fold. These results indicated that the peptide coded for by RNA124 (and by LP154) can be quantitatively isolated by this immunoprecipitation protocol.

Figure 11:
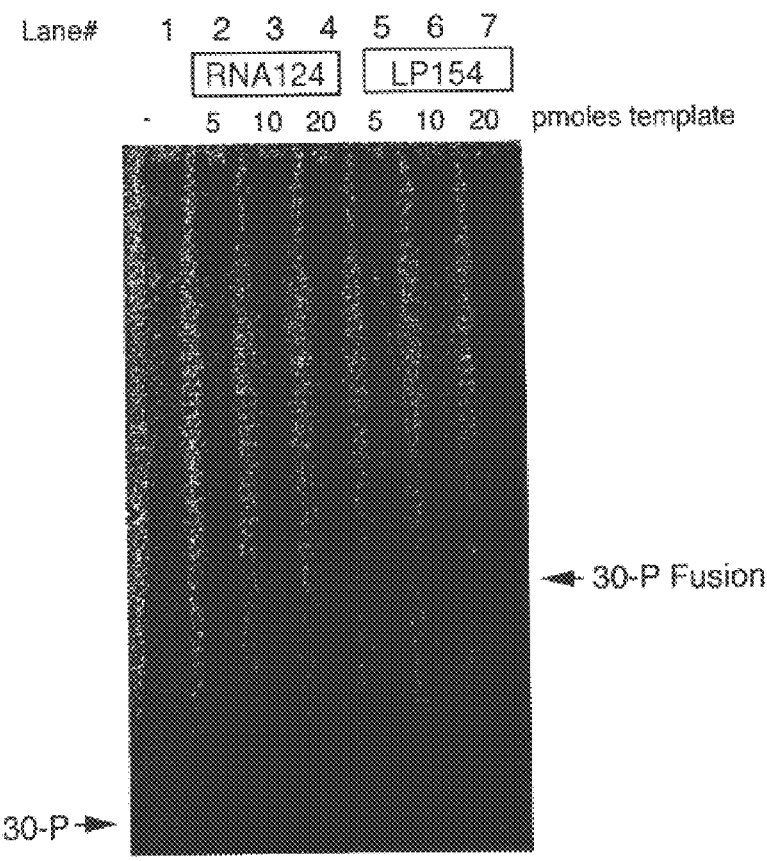
FIG. 11 is a photograph demonstrating immunoprecipitation of an RNA-protein fusion from an in vitro translation reaction. The picomoles of template used in the reaction are indicated. Lanes 1–4 show RNA124 (the RNA portion of fusion LP154), and lanes 5–7 show RNA-protein fusion LP154. After immunoprecipitation using a c-myc monoclonal antibody and protein G sepharose, the samples were treated with RNase A and T4 polynucleotide kinase, then loaded on a denaturing urea polyacrylamide gel to visualize the fusion. In lanes 1–4, with samples containing either no template or only the RNA portion of the long myc template (RNA124), no fusion was seen. In lanes 5–7, bands corresponding to the fusion were clearly visualized. The position of $^{32}$P labeled 30-P is indicated, and the amount of input template is indicated at the top of the figure.
Figure 12:
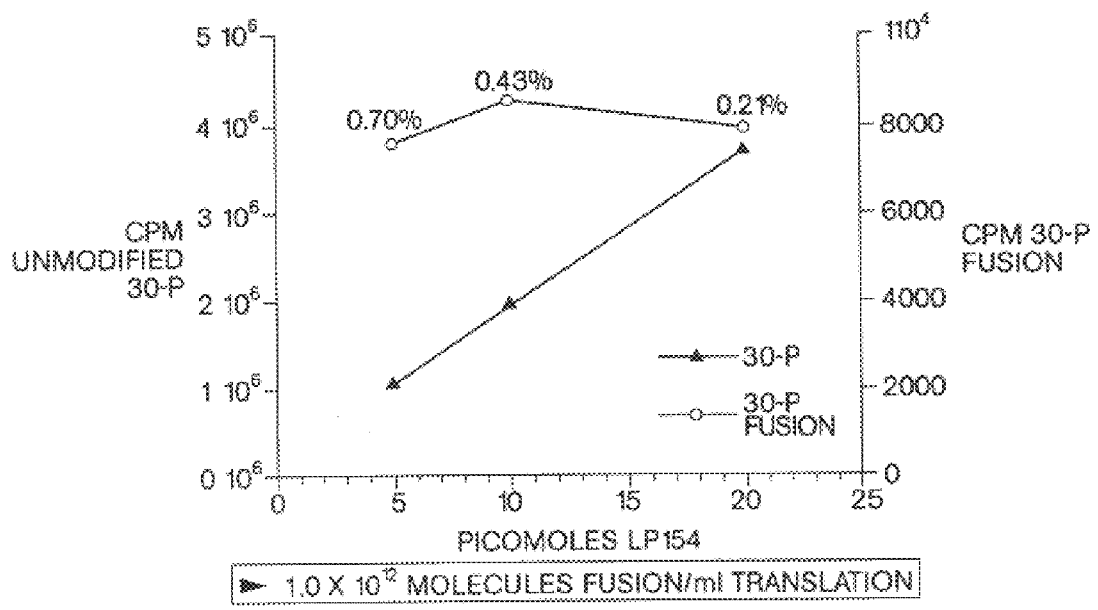
FIG. 12 is a graph showing a quantitation of fusion material obtained from an in vitro translation reaction. The intensity of the fusion bands shown in lanes 5–7 of FIG. 11 and the 30-P band (isolated in a parallel fashion on dT$_{25}$, not shown) were quantitated on phosphorimager plates and plotted as a function of input LP154 concentration. Recovered modified 30-P (left y axis) was linearly proportional to input template (x axis), whereas linker-peptide fusion (right y axis) was constant. From this analysis, it was calculated that ~$10^{12}$ fusions were formed per ml of translation reaction sample.

Immunoprecipitation of the Fusion. We next tested the ability to immunoprecipitate a chimeric RNA-peptide product, using an LP 154 translation reaction and the c-myc monoclonal antibody 9E10 (FIG. 11). The translation products from a reticulocyte reaction were isolated by immunoprecipitation (as described herein) and treated with 1 μg of RNase A at room temperature for 30 minutes to remove the coding sequence. This generated a 5'OH, which was $^{32}$P labeled with T4 polynucleotide kinase and assayed by denaturing PAGE. FIG. 11 demonstrates that a product with a mobility similar to that seen for the fusion of the c-myc epitope with 30-P generated by RNase treatment of the LP154 fusion (see above) was isolated, but no corresponding product was made when only the RNA portion of the template (RNA124) was translated. In FIG. 12, the quantity of fusion protein isolated was determined and was plotted against the amount of unmodified 30-P (not shown in this figure). Quantitation of the ratio of unmodified linker to linker-myc peptide fusion shows that 0.2–0.7% of the input message was converted to fusion product. A higher fraction of the input RNA was converted to fusion product in the presence of a higher ribosome/template ratio; over the range of input mRNA concentrations that were tested, approximately $0.8–1.0\times10^{12}$ fusion molecules were made per ml of translation extract.

In addition, our results indicated that the peptides attached to the RNA species were encoded by that mRNA, i.e. the nascent peptide was not transferred to the puromycin of some other mRNA. No indication of cross-transfer was seen when a linker (30-P) was coincubated with the long myc template in translation extracts in ratios as high as 20:1, nor did the presence of free linker significantly decrease the amount of long myc fusion produced. Similarly, co-translation of the short and long templates, 43-P and LP154, produced only the fusion products seen when the templates were translated alone, and no products of intermediate mobility were observed, as would be expected for fusion of the short template with the long myc peptide. Both of these results suggested that fusion formation occurred primarily between a nascent peptide and mRNA bound to the same ribosome.

Figure 13:
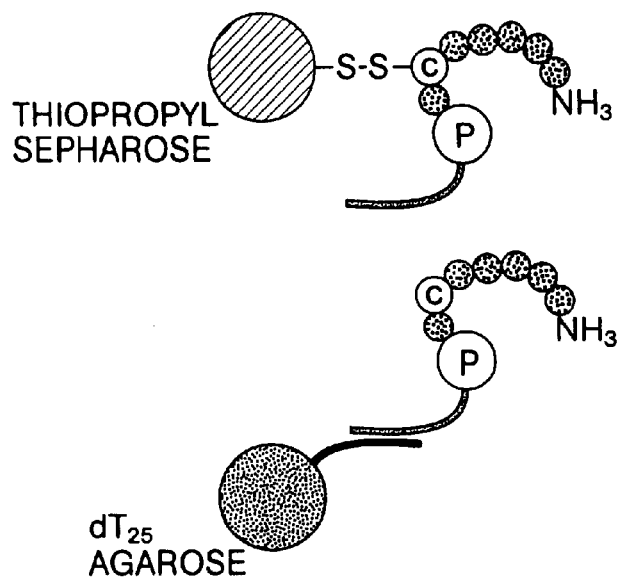
FIG. 13 is a schematic representation of thiopropyl sepharose and dT$_{25}$ agarose, and the ability of these substrates to interact with the RNA-protein fusions of the invention.
Figure 14:
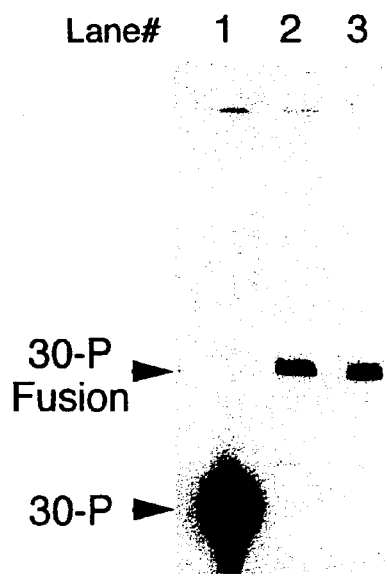
FIG. 14 is a photograph showing the results of sequential isolation of fusions of the invention. Lane 1 contains $^{32}$P labeled 30-P. Lanes 2 and 3 show LP154 isolated from translation reactions and treated with RNase A. In lane 2, LP154 was isolated sequentially, using thiopropyl sepharose followed by dT$_{25}$ agarose. Lane 3 shows isolation using only dT$_{25}$ agarose. The results indicated that the product contained a free thiol, likely the penultimate cysteine in the myc epitope coding sequence.

Sequential Isolation. As a further confirmation of the nature of the in vitro translated LP154 template product, we examined the behavior of this product on two different types of chromatography media. Thiopropyl (TP) sepharose allows the isolation of a product containing a free cysteine (for example, the LP154 product which has a cysteine residue adjacent to the C terminus) (FIG. 13). Similarly, $dT_{25}$ agarose allows the isolation of templates containing a poly dA sequence (for example, 30-P) (FIG. 13). FIG. 14 demonstrates that sequential isolation on TP sepharose followed by $dT_{25}$ agarose produced the same product as isolation on $dT_{25}$ agarose alone. The fact that the in vitro translation product contained both a poly-A tract and a free thiol strongly indicated that the translation product was the desired RNA-peptide fusion.

The above results are consistent with the ability to synthesize mRNA-peptide fusions and to recover them intact from in vitro translation extracts. The peptide portions of fusions so synthesized appeared to have the intended sequences as demonstrated by immunoprecipitation and isolation using appropriate chromatographic techniques. According to the results presented above, the reactions are intramolecular and occur in a template dependent fashion. Finally, even with a template modification of less than 1%, the present system facilitates selections based on candidate complexities of about $10^{13}$ molecules.

C-Myc Epitope Recovery Selection. To select additional c-myc epitopes, a large library of translation templates (for example, $10^{15}$ members) is generated containing a randomized region (see FIG. 7C and below). This library is used to generate $\sim 10^{12} - 10^{13}$ fusions (as described herein) which are treated with the anti-c-myc antibody (for example, by immunoprecipitation or using an antibody immobilized on a column or other solid support) to enrich for c-myc-encoding templates in repeated rounds of in vitro selection.

Models for Fusion Formation. Without being bound to a particular theory, we propose a model for the mechanism of fusion formation in which translation initiates normally and elongation proceeds to the end of the open reading frame. When the ribosome reaches the DNA portion of the template, translation stalls. At this point, the complex can partition between two fates: dissociation of the nascent peptide, or transfer of the nascent peptide to the puromycin at the 3'-end of the template. The efficiency of the transfer reaction is likely to be controlled by a number of factors that influence the stability of the stalled translation complex and the entry of the 3'-puromycin residue into the A site of the peptidyl transferase center. After the transfer reaction, the mRNA-peptide fusion likely remains complexed with the ribosome since the known release factors cannot hydrolyze the stable amide linkage between the RNA and peptide domains.

Both the classical model for elongation (Watson, Bull. Soc. Chim. Biol. 46:1399 (1964)) and the intermediate states model (Moazed and Noller, Nature 342:142 (1989)) require that the A site be empty for puromycin entry into the peptidyl transferase center. For the puromycin to enter the empty A site, the linker must either loop around the outside of the ribosome or pass directly from the decoding site through the A site to the peptidyl transferase center. The data described herein do not clearly distinguish between these alternatives because the shortest linker tested (21 nts) is still long enough to pass around the outside of the ribosome. In some models of ribosome structure (Frank et al., Nature 376:441 (1995)), the mRNA is threaded through a channel that extends on either side of the decoding site, in which case unthreading of the linker from the channel would be required to allow the puromycin to reach the peptidyl transferase center through the A site.

Transfer of the nascent peptide to the puromycin appeared to be slow relative to the elongation process as demonstrated by the homogeneity and length of the peptide attached to the linker. If the puromycin competed effectively with aminoacyl tRNAs during elongation, the linker-peptide fusions present in the fusion products would be expected to be heterogeneous in size. Furthermore, the ribosome did not appear to read into the linker region as indicated by the similarity in gel mobilities between the Met-template fusion and the unmodified linker. $dA_{3n}$ should code for (lysine), which would certainly decrease the mobility of the linker. The slow rate of unthreading of the mRNA may explain the slow rate of fusion formation relative to the rate of translocation. Preliminary results suggest that the amount of fusion product formed increases markedly following extended post-translation incubation at low temperature, perhaps because of the increased time available for transfer of the nascent peptide to the puromycin.

DETAILED MATERIALS AND METHODS

Described below are detailed materials and methods relating to the in vitro translation and testing of RNA-protein fusions, including fusions having a myc epitope tag.

Sequences. A number of oligonucleotides were used above for the generation of RNA-protein fusions. These oligonucleotides have the following sequences.

| NAME | SEQUENCE |
|------|----------|
| 30-P | 5'AAA AAA AAA AAA AAA AAA AAA AAA AAA CCP (SEQ ID NO:8) |
| 13-P | 5'AAA AAA AAA ACC P (SEQ ID NO:9) |
| 25-P | 5'CGC GGT TTT TAT TTT TTT TTT TCC P (SEQ ID NO:10) |

-continued

| NAME | SEQUENCE |
|---|---|
| 43-P | 5'rGrGrA rGrGrA rCrGrA rArArU rGAA AAA AAA AAA AAA AAA AAA AAA AAA ACC P (SEQ ID NO:11) |
| 43-P[CUG] | 5'rGrGrA rGrGrA rCrGrA rArCrU rGAA AAA AAA AAA AAA AAA AAA AAA AAA ACC P (SEQ ID NO:12) |
| 40-P | 5'rGrGrA rGrGrA rCrGrA rArCrU rGAA AAA AAA AAA AAA AAA AAA ACC P(SEQ ID NO:13) |
| 37-P | 5'rGrGrA rGrGrA rCrGrA rArCrU rGAA AAA AAA AAA AAA AAA ACC P (SEQ ID NO:14) |
| 34-P | 5'rGrGrA rGrGrA rCrGrA rArCrU rGAA AAA AAA AAA AAA AAA ACC P (SEQ ID NO:15) |
| 31-P | 5'rGrGrA rGrGrA rCrGrA rArCrU rGAA AAA AAA AAA AAA ACC P (SEQ ID NO:16) |
| LP77 | 5'rGrGrG rArGrG rArCrG rArArA rUrGrG rArArC rArGrA rArArC rUrGrA rUrCrU rCrUrG rArArG rArArG rArCrC rUrGrA rArC AAA AAA AAA AAA AAA AAA AAA AAA AAA CCP (SEQ ID NO:1) |
| LP154 | 5'rCrGrG rArCrA rArUrU rArCrU rArUrU rUrArC rArArU rUrArC rA rArUrG rGrCrU rGrArA rGrArA rCrArG rArArA rCrUrG rArUrC rUrCrU rGrArA rCrArA rGrArC rCrUrG rCrUrG rCrGrU rArArA rCrGrU rCrGrU rCrArA rCrArG rCrUrG rArArA rCrArC rArArA rCrUrG rGrArA rCrArG rCrUrG rCrGrU rArArC rUrCrU rUrGrC rGrCrU AAA AAA AAA AAA AAA AAA AAA AAA AAA CCP (SEQ ID NO:3) |
| LP160 | 5'5'rGrGrG rArCrA rArUrU rArCrU rArUrU rUrArC rArArU rUrArC rA rArUrG rNrNrS rNrNrS rNrNrS rNrNrS rNrNrS rNrNrS rNrNrS rNrNrS rNrNrS rNrNrS rNrNrS rNrNrS rNrNrS rNrNrS rNrNrS rNrNrS rNrNrS rNrNrS rNrNrS rNrNrS rNrNrS rCrArG rCrUrG rCrGrU rArArC rUrCrU rUrGrC rGrCrU AAA AAA AAA AAA AAA AAA AAA AAA AAA CCP (SEQ ID |

All oligonucleotides are listed in the 5' to 3' direction. Ribonucleotide bases are indicated by lower case "r" prior to the nucleotide designation; P is puromycin; rN indicates equal amounts of rA, rG, rC, and rU; rS indicates equal amounts of rG and rC; and all other base designations indicate DNA oligonucleotides.

Chemicals. Puromycin HCl, long chain alkylamine controlled pore glass, gougerotin, chloramphenicol, virginiamycin, DMAP, dimethyltrityl chloride, and acetic anhydride were obtained from Sigma Chemical (St. Louis, Mo.). Pyridine, dimethylformamide, toluene, succinic anhydride, and para-nitrophenol were obtained from Fluka Chemical (Ronkonkoma, N.Y.). Beta-globin mRNA was obtained from Novagen (Madison, Wis.). TMV RNA was obtained from Boehringer Mannheim (Indianapolis, Ind.).

Enzymes. Proteinase K was obtained from Promega (Madison, Wis.). DNase-free RNAase was either produced by the protocol of Sambrook et al. (supra) or purchased from Boehringer Mannheim. T7 polymerase was made by the published protocol of Grodberg and Dunn (J. Bacteriol. 170:1245 (1988)) with the modifications of Zawadzki and Gross (Nucl. Acids Res. 19:1948 (1991)). T4 DNA ligase was obtained from New England Biolabs (Beverly, Mass.).

Quantitation of Radiolabel Incorporation. For radioactive gels bands, the amount of radiolabel ($^{35}$S or $^{32}$P) present in each band was determined by quantitation either on a Betagen 603 blot analyzer (Betagen, Waltham, Mass.) or using phosphorimager plates (Molecular Dynamics, Sunnyvale, Calif.). For liquid and solid samples, the amount of radiolabel ($^{35}$S or $^{32}$p) present was determined by scintillation counting (Beckman, Columbia, Md.).

Gel Images. Images of gels were obtained by autoradiography (using Kodak XAR film) or using phosphorimager plates (Molecular Dynamics).

Synthesis of CPG Puromycin. Detailed protocols for synthesis of CPG-puromycin are outlined above.

Enzymatic Reactions. In general, the preparation of nucleic acids for kinase, transcription, PCR, and translation reactions using *E. coli* extracts was the same. Each preparative protocol began with extraction using an equal volume of 1:1 phenol/chloroform, followed by centrifugation and isolation of the aqueous phase. Sodium acetate (pH 5.2) and spermidine were added to a final concentration of 300 mM and 1 mM respectively, and the sample was precipitated by addition of 3 volumes of 100% ethanol and incubation at −70° C. for 20 minutes. Samples were centrifuged at >12, 000 g, the supernatant was removed, and the pellets were washed with an excess of 95% ethanol, at 0° C. The resulting pellets were then dried under vacuum and resuspended.

Oligonucleotides. All synthetic DNA and RNA was synthesized on a Millipore Expedite synthesizer using standard chemistry for each as supplied from the manufacturer (Milligen, Bedford, Mass.). Oligonucleotides containing 3' puromycin were synthesized using CPG puromycin columns packed with 30–50 mg of solid support (~20 μmole puromycin/gram). Oligonucleotides containing a 3' biotin were synthesized using 1 μmole bioteg CPG columns from Glen Research (Sterling, Va.). Oligonucleotides containing a 5' biotin were synthesized by addition of bioteg phosphoramidite (Glen Research) as the 5' base. Oligonucleotides to be ligated to the 3' ends of RNA molecules were either chemically phosphorylated at the 5' end (using chemical phosphorylation reagent from Glen Research) prior to deprotection or enzymatically phosphorylated using ATP and T4 polynucleotide kinase (New England Biolabs) after deprotection. Samples containing only DNA (and 3' puromycin or 3' biotin) were deprotected by addition of 25% NH$_4$OH followed by incubation for 12 hours at 55° C. Samples containing RNA monomers (e.g., 43-P) were deprotected by addition of ethanol (25% (v/v)) to the NH$_4$OH solution and incubation for 12 hours at 55° C. The 2'OH was deprotected using 1M TBAF in THF (Sigma) for 48 hours at room temperature. TBAF was removed using a NAP-25 Sephadex column (Pharmacia, Piscataway, N.J.).

Deprotected DNA and RNA samples were then purified using denaturing PAGE, followed by either soaking or electro-eluting from the gel using an Elutrap (Schleicher and Schuell, Keene, N.H.) and desalting using either a NAP-25 Sephadex column or ethanol precipitation as described above.

Myc DNA construction. Two DNA templates containing the c-myc epitope tag were constructed. The first template was made from a combination of the oligonucleotides 64.27 (5'-GTT CAG GTC TTC TTG AGA GAT CAG TTT CTG TTC CAT TTC GTC CTC CCT ATA GTG AGT CGT ATT A-3') (SEQ ID NO:18) and 18.109 (5'-TAA TAC GAC TCA CTA TAG-3') (SEQ ID NO:19). Transcription using this template produced RNA 47.1 which coded for the peptide MEQKLISEEDLN (SEQ ID NO:20). Ligation of RNA 47.1 to 30-P yielded LP77 shown in FIG. 7A.

The second template was made first as a single oligonucleotide 99 bases in length, having the designation RWR 99.6 and the sequence 5'AGC GCA AGA GTT ACG CAG CTG TTC CAG TTT GTG TTT CAG CTG TTC ACG ACG TTT ACG CAG CAG GTC TTC TTC AGA GAT CAG TTT CTG TTC TTC AGC CAT-3' (SEQ ID NO:21). Double stranded transcription templates containing this sequence were constructed by PCR with the oligos RWR 21.103 (5'-AGC GCA AGA GTT ACG CAG CTG-3') (SEQ ID NO:22) and RWR 63.26 (5'TAA TAC GAC TCA CTA TAG GGA CAA TTA CTA TTT ACA ATT ACA ATG GCT GAA GAA CAG AAA CTG-3') (SEQ ID NO:23) according to published protocols (Ausubel et al., supra, chapter 15). Transcription using this template produced an RNA referred to as RNA124 which coded for the peptide MAEEQKLI-SEEDLLRKRREQLKHKLEQLRNSCA (SEQ ID NO:24). This peptide contained the sequence used to raise monoclonal antibody 9E10 when conjugated to a carrier protein (Oncogene Science Technical Bulletin). RNA124 was 124 nucleotides in length, and ligation of RNA124 to 30-P produced LP154 shown in FIG. 7B. The sequence of RNA 124 is as follows (SEQ ID NO:32): 5'-rGrGrG rArCrA rArUrU rArCrU rArUrU rUrArC rArArU rUrArC rArArUrG rGrCrU rGrArA rGrArA rCrArG rArArA rCrUrG rArUrC rUrCrU rGrArA rGrArA rCrArC rCrUrG rCrGrU rArArA rCrGrU rCrGrU rGrArA rCrArG rCrUrG rArArA rCrArC rArArA rCrUrG rGrArA rCrArG rCrUrG rCrGrU rArArC rUrCrU rUrGrC rGrCrU-3'

Randomized Pool Construction. The randomized pool was constructed as a single oligonucleotide 130 bases in length denoted RWR130.1. Beginning at the 3' end, the sequence was 3' CCCTGTTAATGATAAATGTTAATGT-TAC (NNS)27 GTC GAC GCA TTG AGA TAC CGA-5' (SEQ ID NO:25). N denotes a random position, and this sequence was generated according to the standard synthesizer protocol. S denotes an equal mix of dG and dC bases. PCR was performed with the oligonucleotides 42.108 (5'-TAA TAC GAC TCA CTA TAG GGA CAA TTA CTA TTT ACA ATT ACA) (SEQ ID NO:26) and 21.103 (5'-AGC GCA AGA GTT ACG CAG CTG) (SEQ ID NO:27). Transcription off this template produced an RNA denoted pool 130.1. Ligation of pool 130.1 to 30-P yielded Pool #1 (also referred to as LP160) shown in FIG. 7C.

Seven cycles of PCR were performed according to published protocols (Ausubel et al., supra) with the following exceptions: (i) the starting concentration of RWR130.1 was 30 nanomolar, (ii) each primer was used at a concentration of 1.5 $\mu$M, (iii) the dNTP concentration was 400 $\mu$M for each base, and (iv) the Taq polymerase (Boehringer Mannheim) was used at 5 units per 100 $\mu$l. The double stranded product was purified on non-denaturing PAGE and isolated by electroelution. The amount of DNA was determined both by UV absorbance at 260 nm and ethidium bromide fluorescence comparison with known standards.

Enzymatic Synthesis of RNA. Transcription reactions from double stranded PCR DNA and synthetic oligonucleotides were performed as described previously (Milligan and Uhlenbeck, Meth. Enzymol. 180:51 (1989)). Full length RNA was purified by denaturing PAGE, electroeluted, and desalted as described above. The pool RNA concentration was estimated using an extinction coefficient of 1300 O.D./$\mu$mole; RNA124, 1250 O.D./$\mu$mole; RNA 47.1, 480 O.D./$\mu$mole. Transcription from the double stranded pool DNA produced ~90 nanomoles of pool RNA.

Enzymatic Synthesis of RNA-Puromycin Conjugates. Ligation of the myc and pool messenger RNA sequences to the puromycin containing oligonucleotide was performed using a DNA splint, termed 19.35 (5'-TTT TTT TTT TAG CGC AAG A) (SEQ ID NO:28) using a procedure analogous to that described by Moore and Sharp (Science 250:992 (1992)). The reaction consisted of mRNA, splint, and puromycin oligonucleotide (30-P, dA27dCdCP) in a mole ratio of 0.8: 0.9: 1.0 and 1–2.5 units of DNA ligase per picomole of pool mRNA. Reactions were conducted for one hour at room temperature. For the construction of the pool RNA fusions, the mRNA concentration was 6.6 $\mu$molar. Following ligation, the RNA-puromycin conjugate was prepared as described above for enzymatic reactions. The precipitate was resuspended, and full length fusions were purified on denaturing PAGE and isolated by electroelution as described above. The pool RNA concentration was estimated using an extinction coefficient of 1650 O.D./$\mu$mole and the myc template 1600 O.D./$\mu$mole. In this way, 2.5 nanomoles of conjugate were generated.

Preparation of dT$_{25}$ Steptavidin Agarose. dT$_{25}$ containing a 3' biotin (synthesized on bioteg phosphoramidite columns (Glen Research)) was incubated at 1–10 $\mu$M with a slurry of streptavidin agarose (50% agarose by volume, Pierce, Rockford, Ill.) for 1 hour at room temperature in TE (10 mM Tris Chloride pH 8.2, 1 mM EDTA) and washed. The binding capacity of the agarose was then estimated optically by the disappearance of biotin-dT$_{25}$ from solution and/or by titration of the resin with known amounts of complementary oligonucleotide.

Translation Reactions using E. coli Derived Extracts and Ribosomes. In general, translation reactions were performed with purchased kits (for example, E. coli S30 Extract for Linear Templates, Promega, Madison, Wis.). However, E. coli MRE600 (obtained from the ATCC, Rockville, Md.) was also used to generate S30 extracts prepared according to published protocols (for example, Ellman et al., Meth. Enzymol. 202:301(1991)), as well as a ribosomal fraction prepared as described by Kudlicki et al. (Anal. Biochem. 206:389 (1992)). The standard reaction was performed in a 50 $\mu$l volume with 20–40 $\mu$Ci of $^{35}$S methionine as a marker. The reaction mixture consisted of 30% extract v/v, 9–18 mM MgCl$_2$, 40% premix minus methionine (Promega) v/v, and 5 $\mu$M of template (e.g., 43-P). For coincubation experiments, the oligos 13-P and 25-P were added at a concentration of 5 $\mu$M. For experiments using ribosomes, 3 $\mu$l of ribosome solution was added per reaction in place of the lysate. All reactions were incubated at 37° C. for 30 minutes. Templates were purified as described above under enzymatic reactions.

Wheat Germ Translation Reactions. The translation reactions in FIG. 8 were performed using purchased kits lacking methionine (Promega), according to the manufacturer's recommendations. Template concentrations were 4 μM for 43-P and 0.8 μM for LP77 and LP154. Reactions were performed at 25° C. with 30 μCi $^{35}$S methionine in a total volume of 25 μl.

Reticulocyte Translation Reactions. Translation reactions were performed either with purchased kits (Novagen, Madison, Wis.) or using extract prepared according to published protocols (Jackson and Hunt, Meth. Enzymol. 96:50 (1983)). Reticulocyte-rich blood was obtained from Pel-Freez Biologicals (Rogers, Ark.). In both cases, the reaction conditions were those recommended for use with Red Nova Lysate (Novagen). Reactions consisted of 100 mM KCl, 0.5 mM MgOAc, 2 mM DTT, 20 mM HEPES pH 7.6, 8 mM creatine phosphate, 25 μM in each amino acid (with the exception of methionine if $^{35}$S Met was used), and 40% v/v of lysate. Incubation was at 30° C. for 1 hour. Template concentrations depended on the experiment but generally ranged from 50 nM to 1 μM with the exception of 43-P (FIG. 6H) which was 4 μM.

For generation of the randomized pool, 10 ml of translation reaction was performed at a template concentration of ~0.1 μM (1.25 nanomoles of template). In addition, $^{32}$P labeled template was included in the reaction to allow determination of the amount of material present at each step of the purification and selection procedure. After translation at 30° C. for one hour, the reaction was cooled on ice for 30–60 minutes.

Isolation of Fusion with dT$_{25}$ Streptavidin Agarose. After incubation, the translation reaction was diluted approximately 150 fold into isolation buffer (1.0 M NaCl, 0.1M Tris chloride pH 8.2, 10 mM EDTA, 1 mM DTT) containing greater than a 10X molar excess of dT$_{25}$-biotin-streptavidin agarose whose dT$_{25}$ concentration was ~10 μM (volume of slurry equal or greater than the volume of lysate) and incubated with agitation at 4° C. for one hour. The agarose was then removed from the mixture either by filtration (Millipore ultrafree MC filters) or centrifugation and washed with cold isolation buffer 2–4 times. The template was then liberated from the dT$_{25}$ streptavidin agarose by repeated washing with 50–100 μl aliquots of 15 mM NaOH, 1 mM EDTA. The eluent was immediately neutralized in 3M NaOAc pH 5.2, 10 mM spermidine, and was ethanol precipitated. For the pool reaction, the total radioactivity recovered indicated approximately 50–70% of the input template was recovered.

Isolation of Fusion with Thiopropyl Sepharose. Fusions containing cysteine can be purified using thiopropyl sepharose 6B as in FIG. 13 (Pharmacia). In the experiments described herein, isolation was either carried out directly from the translation reaction or following initial isolation of the fusion (e.g., with streptavidin agarose). For samples purified directly, a ratio of 1:10 (v/v) lysate to sepharose was used. For the pool, 0.5 ml of sepharose slurry was used to isolate all of the fusion material from 5 ml of reaction mixture. Samples were diluted into a 50:50 (v/v) slurry of thiopropyl sepharose in 1X TE 8.2 (10 mM Tris-Cl, 1 mM EDTA, pH 8.2) containing DNase free RNase (Boehringer Mannheim) and incubated with rotation for 1–2 hours at 4° C. to allow complete reaction. The excess liquid was removed, and the sepharose was washed repeatedly with isolation buffer containing 20 mM DTT and recovered by centrifugation or filtration. The fusions were eluted from the sepharose using a solution of 25-30 mM dithiothreitol (DTT) in 10 mM Tris chloride pH 8.2, 1 mM EDTA. The fusion was then concentrated by a combination of evaporation under high vacuum and ethanol precipitation as described above. For the pool reaction, the total radioactivity recovered indicated approximately 1% of the template was converted to fusion.

For certain applications, dT$_{25}$ was added to this eluate and rotated for 1 hour at 4° C. The agarose was rinsed three times with cold isolation buffer, isolated via filtration, and the bound material eluted as above. Carrier tRNA was added, and the fusion product was ethanol precipitated. The sample was resuspended in TE pH 8.2 containing DNase free RNase A to remove the RNA portion of the template.

Immunoprecipitation Reactions. Immunoprecipitations of peptides from translation reactions (FIG. 10) were performed by mixing 4 μl of reticulocyte translation reaction, 2 μl normal mouse sera, and 20 μl Protein G+A agarose (Calbiochem, La Jolla, Calif.) with 200 μl of either PBS (58 mM Na$_2$HPO$_4$, 17 mM NaH$_2$PO$_4$, 68 mM NaCl), dilution buffer (10 mM Tris chloride pH 8.2, 140 mM NaCl, 10 1% v/v Triton X-100), or PBSTDS (PBS+1% Triton X-100, 0.5% deoxycholate 0.1% SDS). Samples were then rotated for one hour at 4° C., followed by centrifugation at 2500 rpm for 15 minutes. The eluent was removed, and 10 μl of c-myc monoclonal antibody 9E10 (Calbiochem, La Jolla, Calif.) and 15 l of Protein G+A agarose was added and rotated for 2 hours at 4° C. Samples were then washed with two 1 ml volumes of either PBS, dilution buffer, or PBSTDS. 40 μl of gel loading buffer (Calbiochem Product Bulletin) was added to the mixture, and 20 μl was loaded on a denaturing PAGE as described by Schagger and von Jagow (Anal. Biochem. 166:368 (1987)).

Immunoprecipitations of fusions (as shown in FIG. 11) were performed by mixing 8 μl of reticulocyte translation reaction with 300 μl of dilution buffer (10 mM Tris chloride pH 8.2, 140 mM NaCl, 1% v/v Triton X-100), 15 μl protein G sepharose (Sigma), and 10 μl (1 μg) c-myc antibody 9E10 (Calbiochem), followed by rotation for several hours at 4° C. After isolation, samples were washed, treated with DNase free RNase A, labeled with polynucleotide kinase and 32p gamma ATP, and separated by denaturing urea PAGE (FIG. 11).

Reverse Transcription of Fusion Pool. Reverse transcription reactions were performed according to the manufacturers recommendation for Superscript II, except that the template, water, and primer were incubated at 70° C. for only two minutes (Gibco BRL, Grand Island, N.Y.). To monitor extension, 50 μCi alpha $^{32}$P dCTP was included in some reactions; in other reactions, reverse transcription was monitored using 5' $^{32}$P-labeled primers which were prepared using $^{32}$P αATP (New England Nuclear, Boston, Msss.) and T4 polynucleotide kinase (New England Biolabs, Beverly, Mass.).

Preparation of Protein G and Antibody Sepharose. Two aliquots of 50 μl Protein G sepharose slurry (50% solid by volume) (Sigma) were washed with dilution buffer (10 mM Tris chloride pH 8.2,140 mM NaCl, 0.025% NaN$_3$, 1% v/v Triton X-100) and isolated by centrifugation. The first aliquot was reserved for use as a precolumn prior to the selection matrix. After resuspension of the second aliquot in dilution buffer, 40 μg of c-myc AB-1 monoclonal antibody (Oncogene Science) was added, and the reaction incubated overnight at 4° C. with rotation. The antibody sepharose was then purified by centrifugation for 15 minutes at 1500–2500 rpm in a microcentrifuge and washed 1–2 times with dilution buffer.

Selection. After isolation of the fusion and complementary strand synthesis, the entire reverse transcriptase reaction was used directly in the selection process. Two protocols are outlined here. For round one, the reverse transcriptase reaction was added directly to the antibody sepharose prepared as described above and incubated 2 hours. For subsequent rounds, the reaction is incubated ~2 hours with washed protein G sepharose prior to the antibody column to decrease the number of binders that interact with protein G rather than the immobilized antibody.

To elute the pool from the matrix, several approaches may be taken. The first is washing the selection matrix with 4% acetic acid. This procedure liberates the peptide from the matrix. Alternatively, a more stringent washing (e.g., using urea or another denaturant) may be used instead or in addition to the acetic acid approach.

PCR of Selected Fusions. Selected molecules are amplified by PCR using standard protocols as described above for construction of the pool.

SYNTHESIS AND TESTING OF BETA-GLOBIN FUSIONS

To synthesize a β-globin fusion construct, β-globin cDNA was generated from 2.5 μg globin mRNA by reverse transcription with 200 pmoles of primer 18.155 (5' GTG GTA TTT GTG AGC CAG) (SEQ ID NO: 29) and Superscript reverse transcriptase (Gibco BRL) according to the manufacturer's protocol. The primer sequence was complementary to the 18 nucleotides of β-globin 5' of the stop codon. To add a T7 promoter, 20 μl of the reverse transcription reaction was removed and subjected to 6 cycles of PCR with primers 18.155 and 40.54 (5' TAA TAC GAC TCA CTA TAG GGA CAC TTG CTT TTG ACA CAA C) (SEQ ID NO:30). The resulting "syn-β-globin" mRNA was then generated by T7 runoff transcription according to Milligan and Uhlenbeck (Methods Enzymol. 180:51 (1989)), and the RNA gel purified, electroeluted, and desalted as described herein. "LP-β-globin" was then generated from the syn-β-globin construct by ligation of that construct to 30-P according to the method of Moore and Sharp (Science 256:992 (1992)) using primer 20.262 (5' TTT TTT TTT T GTG GTA TTT G) (SEQ ID NO:31) as the splint. The product of the ligation reaction was then gel purified, electroeluted, and desalted as above. The concentration of the final product was determined by absorbance at 260 nm.

These β-globin templates were then translated in vitro as described in Table 1 in a total volume of 25 μl each. $Mg^{2+}$ was added from a 25 mM stock solution. All reactions were incubated at 30° C. for one hour and placed at −20° C. overnight. $dT_{25}$ precipitable CPM's were then determined twice using 6 μl of lysate and averaged minus background.

TABLE 1

Translation Reactions with Beta-Globin Templates

| Reaction | Template | $Mg^{2+}$ (mM) | $^{35}$S Met (μl) | TCA CPM (2 μl) | $dT_{25}$ CPM (6 μl) |
|---|---|---|---|---|---|
| 1 | — | 1.0 | 2.0 (20 μCi) | 3312 | 0 |
| 2 | 2.5 μg syn-β-globin | 0.5 | 2.0 (20 μCi) | 33860 | 36 |
| 3 | 2.5 μg syn-β-globin | 1.0 | 2.0 (20 μCi) | 22470 | 82 |
| 4 | 2.5 μg syn-β-globin | 2.0 | 2.0 (20 μCi) | 15696 | 86 |
| 5 | 2.5 μg LP-β-globin | 0.5 | 2.0 (20 μCi) | 32712 | 218 |
| 6 | 2.5 μg LP-β-globin | 1.0 | 2.0 (20 μCi) | 24226 | 402 |

TABLE 1-continued

Translation Reactions with Beta-Globin Templates

| Reaction | Template | $Mg^{2+}$ (mM) | $^{35}$S Met (μl) | TCA CPM (2 μl) | $dT_{25}$ CPM (6 μl) |
|---|---|---|---|---|---|
| 7 | 2.5 μg LP-β-globin | 2.0 | 2.0 (20 μCi) | 15074 | 270 |

To prepare the samples for gel analysis, 6 μl of each translation reaction was mixed with 1000 μl of Isolation Buffer (1M NaCl, 100 mM Tris-Cl pH 8.2, 10 mM EDTA, 0.1 mM DTT), 1 μl RNase A (DNase Free, Boehringer Mannheim), and 20 μl of 20 μM $dT_{25}$ streptavidin agarose. Samples were incubated at 4° C. for one hour with rotation. Excess Isolation Buffer was removed, and the samples were added to a Millipore MC filter to remove any remaining Isolation Buffer. Samples were then washed four times with 50 μl of $H_2O$, and twice with 50 μl of 15 mM NaOH, 1 mM EDTA. The sample (300 μl) was neutralized with 100 μl TE pH 6.8 (10 mM Tris-Cl, 1 mM EDTA), 1 μl of 1 mg/ml RNase A (as above) was added, and the samples were incubated at 37° C. 10 μl of 2X SDS loading buffer (125 mM Tris-Cl pH 6.8, 2% SDS, 2% β-mercaptoethanol 20% glycerol, 0.001% bromphenol blue) was then added, and the sample was lyophilized to dryness and resuspended in 20 μl $H_2O$ and 1% β-mercaptoethanol. Samples were then loaded onto a peptide resolving gel as described by Schagger and von Jagow (Analytical Biochemistry 166:368 (1987)) and visualized by autoradiography.

Figure 15B:
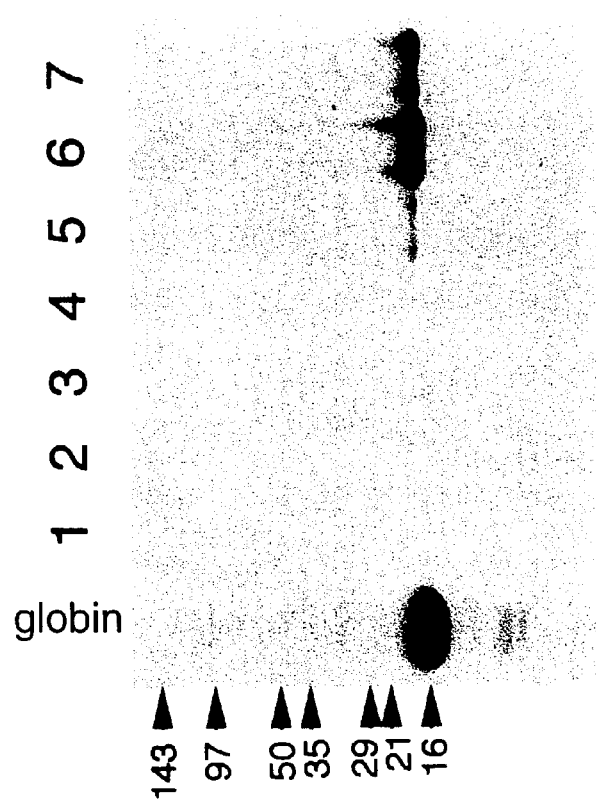
FIGS. 15A and 15B are photographs showing the formation of fusion products using β-globin templates as assayed by SDS-tricine-PAGE (polyacrylamide gel electrophoresis).
Figure 15A:
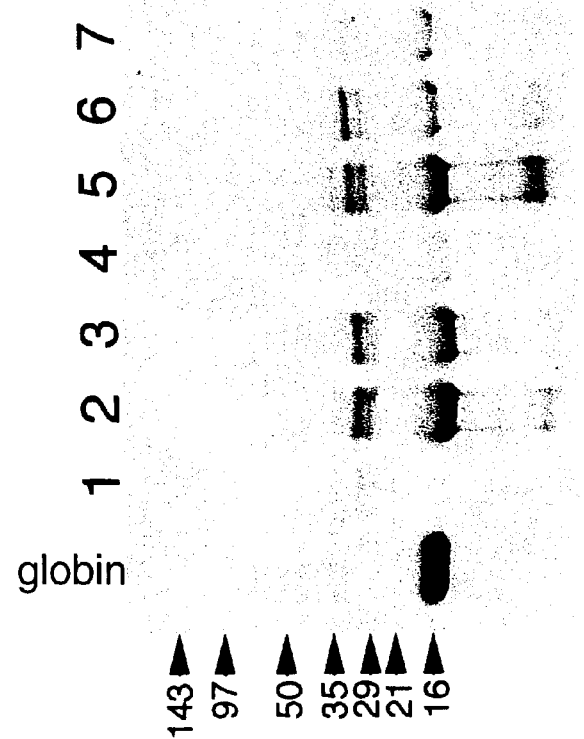

The results of these experiments are shown in FIGS. 15A and 15B. As indicated in FIG. 15A, $^{35}$S-methionine was incorporated into the protein portion of the syn-β-globin and LP-β-globin fusions. The protein was heterogeneous, but one strong band exhibited the mobility expected for β-globin mRNA. Also, as shown in FIG. 15B, after $dT_{25}$ isolation and RNase A digestion, no $^{35}$S-labeled material remained in the syn-p-globin lanes (FIG. 15B, lanes 2–4). In contrast, in the LP-β-globin lanes, a homogeneously sized $^{35}$S-labeled product was observed.

These results indicated that, as above, a fusion product was isolated by oligonucleotide affinity chromatography only when the template contained a 3' puromycin. This was confirmed by scintillation counting (see Table 1). The material obtained is expected to contain the 30-P linker fused to some portion of β-globin. The fusion product appeared quite homogeneous in size as judged by gel analysis. However, since the product exhibited a mobility very similar to natural β-globin (FIGS. 15A and 15B, control lanes), it was difficult to determine the precise length of the protein portion of the fusion product.

FURTHER OPTIMIZATION OF RNA-PROTEIN FUSION FORMATION

Certain factors have been found to further increase the efficiency of formation of RNA-peptide fusions. Fusion formation, i.e., the transfer of the nascent peptide chain from its tRNA to the puromycin moiety at the 3' end of the mRNA, is a slow reaction that follows the initial, relatively rapid translation of the open reading frame to generate the nascent peptide. The extent of fusion formation may be substantially enhanced by a post-translational incubation in elevated $Mg^{2+}$ conditions (preferably, in a range of 50–100 mM) and/or by the use of a more flexible linker between the mRNA and the puromycin moiety. In addition, long incubations (12–48 hours) at low temperatures (preferably, −20°

C.) also result in increased yields of fusions with less mRNA degradation than that which occurs during incubation at 30° C. By combining these factors, up to 40% of the input mRNA may be converted to mRNA-peptide fusion products, as shown below.

Synthesis of mRNA-Puromycin Conjugates. In these optimization experiments, puromycin-containing linker oligonucleotides were ligated to the 3' ends of mRNAs using bacteriophage T4 DNA ligase in the presence of complementary DNA splints, generally as described above. Since T4 DNA ligase prefers precise base-pairing near the ligation junction and run-off transcription products with T7, T3, or SP6 RNA polymerase are often heterogeneous at their 3' ends (Nucleic Acids Research 15:8783 (1987)), only those RNAs containing the correct 3'-terminal nucleotide were efficiently ligated. When a standard DNA splint was used, approximately 40% of runoff transcription products were ligated to the puromycin oligo. The amount of ligation product was increased by using excess RNA, but was not increased using excess puromycin oligonucleotide. Without being bound to a particular theory, it appeared that the limiting factor for ligation was the amount of RNA which was fully complementary to the corresponding region of the DNA splint.

To allow ligation of those transcripts ending with an extra non-templated nucleotide at the 3' terminus (termed "N+1 products"), a mixture of the standard DNA splint with a new DNA splint containing an additional random base at the ligation junction was used. The ligation efficiency increased to more than 70% for an exemplary myc RNA template (that is, RNA124) in the presence of such a mixed DNA splint.

In addition to this modified DNA splint approach, the efficiency of mRNA-puromycin conjugate formation was also further optimized by taking into account the following three factors. First, mRNAs were preferably designed or utilized which lacked 3'-termini having any significant, stable secondary structure that would interfere with annealing to a splint oligonucleotide. In addition, because a high concentration of salt sometimes caused failure of the ligation reaction, thorough desalting of the oligonucleotides using NAP-25 columns was preferably included as a step in the procedure. Finally, because the ligation reaction was relatively rapid and was generally complete within 40 minutes at room temperature, significantly longer incubation periods were not generally utilized and often resulted in unnecessary degradation of the RNA.

Using the above conditions, mRNA-puromycin conjugates were synthesized as follows. Ligation of the myc RNA sequence (RNA124) to the puromycin-containing oligonucleotide was performed using either a standard DNA splint (e.g., 5'-TTTTTTTTTTAGCGCAAGA) (SEQ ID NO:28) or a splint containing a random base (N) at the ligation junction (e.g., 5'-TTTTTTTTTTNAGCGCAAGA) (SEQ ID NO:33). The reactions consisted of mRNA, the DNA splint, and the puromycin oligonucleotide in a molar ratio of 1.0: 1.5–2.0: 1.0. A mixture of these components was first heated at 94° C. for 1 minute and then cooled on ice for 15 minutes. Ligation reactions were performed for one hour at room temperature in 50 mM Tris-HCl (pH 7.5), 10 MM $MgCl_2$, 10 mM DTT, 1 mM ATP, 25 μg/ml BSA, 15 μM puromycin oligo, 15 μM mRNA, 22.5–30 μM DNA splint, RNasin inhibitor (Promega) at 1 U/μl, and 1.6 units of T4 DNA ligase per picomole of puromycin oligo. Following incubation, EDTA was added to a final concentration of 30 mM, and the reaction mixtures were extracted with phenol/chloroform. Full length conjugates were purified by denaturing PAGE and isolated by electroelution.

General Reticulocyte Translation Conditions. In addition to improving the synthesis of the mRNA-puromycin conjugate, translation reactions were also further optimized as follows. Reactions were performed in rabbit reticulocyte lysates from different commercial sources (Novagen, Madison, Wis.; Amersham, Arlington Heights, Ill.; Boehringer Mannheim, Indianapolis, Ind.; Ambion, Austin, Tex.; and Promega, Madison, Wis.). A typical reaction mixture (25 μl final volume) consisted of 20 mM HEPES pH 7.6, 2 mM DTT, 8 mM creatine phosphate, 100 mM KCl, 0.75 mM Mg(OAc)$_2$, 1 mM ATP, 0.2 mM GTP, 25 μM of each amino acid (0.7 μM methionine if $^{35}$S-Met was used), RNasin at 1 U/μl, and 60% (v/v) lysate. The final concentration of template was in the range of 50 nM to 800 nM. For each incubation, all components except lysate were mixed carefully on ice, and the frozen lysate was thawed immediately before use. After addition of lysate, the reaction mixture was mixed thoroughly by gentle pipetting and incubated at 30° C. to start translation. The optimal concentrations of $Mg^{2+}$ and $K^+$ varied within the ranges of 0.25 mM–2 mM and 75 mM–200 mM, respectively, for different mRNAs and was preferably determined in preliminary experiments. Particularly for poorly translated mRNAs, the concentrations of hemin, creatine phosphate, tRNA, and amino acids were also sometimes optimized. Potassium chloride was generally preferred over potassium acetate for fusion reactions, but a mixture of KCl and KOAc sometimes produced better results.

After translation at 30° C. for 30 to 90 minutes, the reaction was cooled on ice for 40 minutes, and $Mg^{2+}$ was added. The final concentration of $Mg^{2+}$ added at this step was also optimized for different mRNA templates, but was generally in the range of 50 mM to 100 mM (with 50 mM being preferably used for pools of mixed templates). The resulting mixture was incubated at –20° C. for 16 to 48 hours. To visualize the labeled fusion products, 2 μl of the reaction mixture was mixed with 4 μl loading buffer, and the mixture was heated at 75° C. for 3 minutes. The resulting mixture was then loaded onto a 6% glycine SDS-polyacrylamide gel (for $^{32}$P-labeled templates) or an 8% tricine SDS-polyacrylamide gel (for $^{35}$S-Met-labeled templates). As an alternative to this approach, the fusion products may also be isolated using dT$_{25}$ streptavidin agarose or thiopropyl sepharose (or both), generally as described herein.

To remove the RNA portion of the RNA-linker-puromycin-peptide conjugate for subsequent analysis by SDS-PAGE, an appropriate amount of EDTA was added after post-translational incubation, and the reaction mixture was desalted using a microcon-10 (or microcon-30) column. 2 μl of the resulting mixture (approximately 25 μl total) was mixed with 18 μl of RNase H buffer (30 mM Tris-HCl, pH 7.8, 30 mM (NH$_4$)$_2$SO$_4$, 8 mM MgCl$_2$, 1.5 mM β-mercaptoethanol, and an appropriate amount of complementary DNA splint), and the mixture was incubated at 4° C. for 45 minutes. RNase H was then added, and digestion was performed at 37° C. for 20 minutes.

Quality of Puromycin Oligo. The quality of the puromycin oligonucleotide was also important for the efficient generation of fusion products. The coupling of 5'-DMT, 2'-succinyl, N-trifluoroacetyl puromycin with CPG was not as efficient as the coupling of the standard nucleotides. As such, the coupling reaction was carefully monitored to avoid the formation of CPG with too low a concentration of coupled puromycin, and unreacted amino groups on the CPG were fully quenched to avoid subsequent synthesis of oligonucleotides lacking a 3'-terminal puromycin. It was also important to avoid the use of CPG containing very fine mesh particles, as these were capable of causing problems with valve clogging during subsequent automated oligonucleotide synthesis steps.

In addition, the synthesized puromycin oligo was preferably tested before large scale use to ensure the presence of puromycin at the 3' end. In our experiments, no fusion was detected if puromycin was substituted with a deoxyadenosine containing a primary amino group at the 3' end. To test for the presence of 3' hydroxyl groups (i.e., the undesired synthesis of oligos lacking a 3'-terminal puromycin), the puromycin oligo may first be radiolabeled (e.g., by 5'-phosphorylation) and then used as a primer for extension with terminal deoxynucleotidyl transferase. In the presence of a 3'-terminal puromycin moiety, no extension product should be observed.

Time Course of Translation and Post-Translational Incubation. The translation reaction was relatively rapid and was generally completed within 25 minutes at 30° C. The fusion reaction, however, was slower. When a standard linker ($dA_{27}dCdCP$) was used at 30° C., fusion synthesis reached its maximum level in an additional 45 minutes. The post-translational incubation could be carried out at lower temperatures, for example, room temperature, 0° C., or –20° C. Less degradation of the mRNA template was observed at –20° C., and the best fusion results were obtained after incubation at –20° C. for 2 days.

Figure 17:
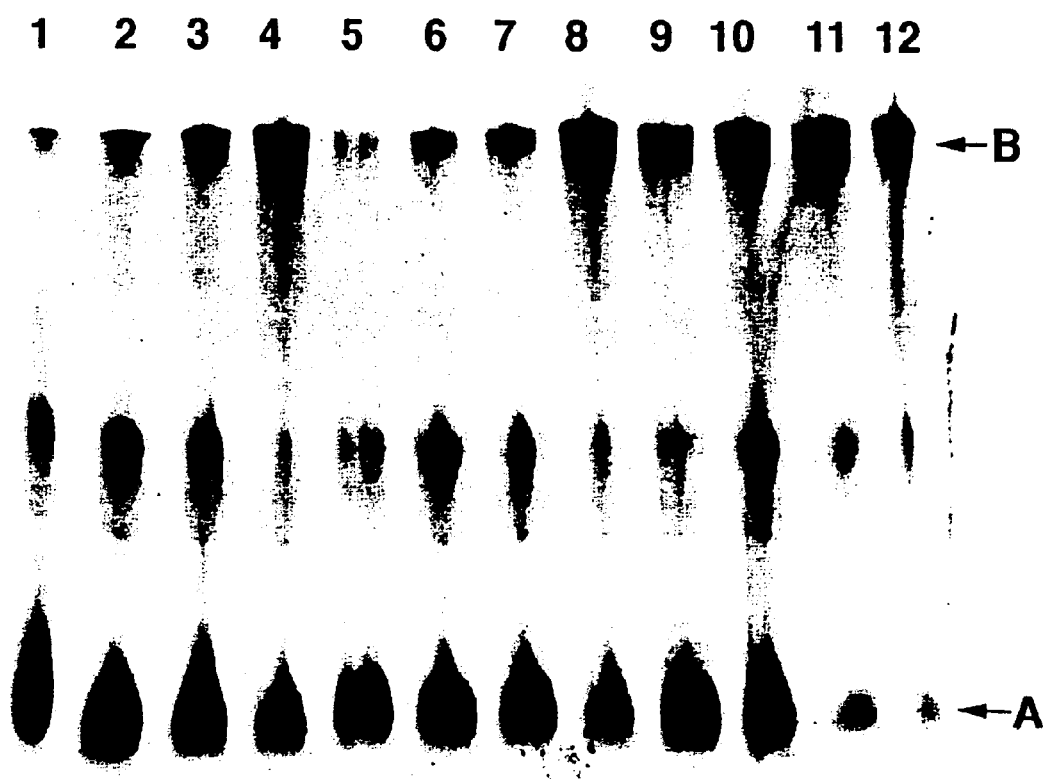
FIG. 17 is a photograph illustrating the translation of myc RNA templates. The following linkers were used: lanes 1–4, $dA_{27}dCdCP$; lanes 5–8, $dA_{27}rCrCP$; and lanes 9–12, $dA_{21}C_9C_9C_9dAdCdCP$. In each lane, the concentration of RNA template was 600 nM, and $^{35}$S-Met was used for labeling. Reaction conditions were as follows: lanes 1, 5, and 9, 30° C. for 1 hour; lanes 2, 6, and 10, 30° C. for 2 hours; lane 3, 7, and 11, 30° C. for 1 hour, −20° C. for 16 hours; and lanes 4, 8, and 12, 30° C. for 1 hour, −20° C. for 16 hours with 50 mM $Mg^{2+}$. In this Figure, "A" represents free peptide, and "B" represent mRNA-peptide fusion.

The Effect of $Mg^{2+}$ Concentration. A high concentration of $Mg^{2+}$ in the post-translational incubation greatly stimulated fusion formation. For example, for the myc RNA template described above, a 3–4 fold stimulation of fusion formation was observed using a standard linker ($dA_{27}dCdCP$) in the presence of 50 mM $Mg^{2+}$ during the 16 hour incubation at –20° C. (FIG. 17, compare lanes 3 and 4). Similarly, efficient fusion formation was also observed using a post-translational incubation in the presence of a 50–100 mM $Mg^{2+}$ concentration when the reactions were carried out at room temperature for 30–45 minutes.

Linker Length and Sequence. The dependence of the fusion reaction on the length of the linker was also examined. In the range between 21 and 30 nucleotides (n=18–27), little change was seen in the efficiency of the fusion reaction (as described above). Shorter linkers (e.g., 13 nucleotides in length) resulted in lower fusion. In addition, although particular linkers of greater length (that is, of 45 nucleotides and 54 nucleotides) also resulted in somewhat lower fusion efficiences, it remains likely that yet longer linkers may also be used to optimize the efficiency of the fusion reaction.

With respect to linker sequence, substitution of deoxyribonucleotide residues near the 3' end with ribonucleotide residues did not significantly change the fusion efficiency. The dCdCP (or rCrCP) sequence at the 3' end of the linker was, however, important to fusion formation. Substitution of dCdCP with dUdUP reduced the efficiency of fusion formation significantly.

Linker Flexibility. The dependence of the fusion reaction on the flexibility of the linker was also tested. In these experiments, it was determined that the fusion efficiency was low if the rigidity of the linker was increased by annealing with a complementary oligonucleotide near the 3' end. Similarly, when a more flexible linker (for example, $dA21C_9C_9C_9dAdCdCP$, where Cg represents $HO(CH_2CH_2O)_3PO_2$) was used, the fusion efficiency was significantly improved. Compared to the standard linker ($dA_{27}dCdCP$), use of the more flexible linker ($dA_{21}C_9C_9C_9dAdCdCP$) improved the fusion efficiency for RNA124 more than 4-fold (FIG. 17, compare lanes 1 and 9). In addition, in contrast to the template with the standard linker whose post-translation fusion proceeded poorly in the absence of a high concentration of $Mg^{2+}$ (FIG. 17, lane 3 and 4), the template with the flexible linker did not require elevated $Mg^{2+}$ to produce a good yield of fusion product in an extended post-translational incubation at –20° C. (FIG. 17, compare lanes 11 and 12). This linker, therefore, was very usefull if post-translational additions of high concentrations of $Mg^{2+}$ were not desired. In addition, the flexible linker also produced optimal fusion yields in the presence of elevated $Mg^{2+}$.

Quantitation of Fusion Efficiency. Fusion efficiency may be expressed as either the fraction of translated peptide converted to fusion product, or the fraction of input template converted to fusion product. To determine the fraction of translated peptide converted to fusion product, $^{35}$S-Met labeling of the translated peptide was utilized. In these experiments, when a $dA_{27}dCdCP$ or $dA_{27}rCrCP$ linker was used, about 3.5% of the translated peptide was fused to its mRNA after a 1 hour translation incubation at 30° C. This value increased to 12% after overnight incubation at –20° C. When the post-translational incubation was carried out in the presence of a high concentration of $Mg^{2+}$, more than 50% of the translated peptide was fused to the template.

For a template with a flexible linker, approximately 25% of the translated peptide was fused to the template after 1 hour of translation at 30° C. This value increased to over 50% after overnight incubation at –20° C. and to more than 75% if the post-translational incubation was performed in the presence of 50 mM $Mg^{2+}$.

Figure 18:
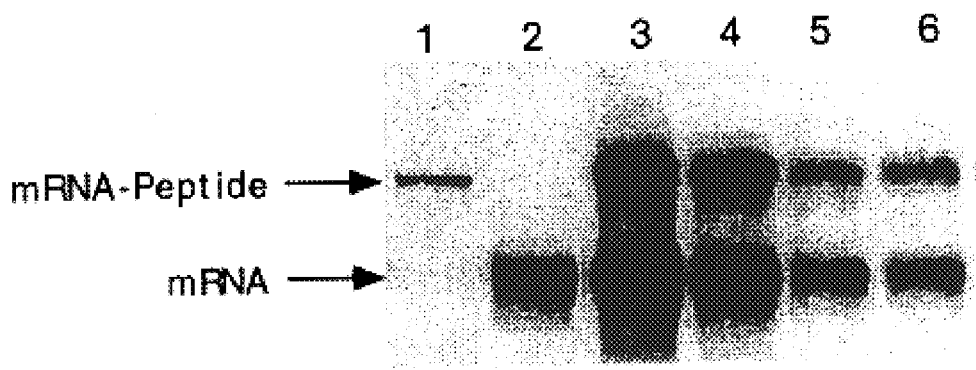
FIG. 18 is a photograph illustrating the translation of myc RNA templates labeled with $^{32}$P. The linker utilized was $dA_{21}C_9C_9C_9dAdCdCP$. Translation was performed at 30° C. for 90 minutes, and incubations were carried out at −20° C. for 2 days without additional $Mg^{2+}$. The concentrations of mRNA templates were 400 nM (lane 3), 200 nM (lane 4), 100 nM (lane 5), and 100 nM (lane 6). Lane 1 shows mRNA-peptide fusion labeled with $^{35}$S-Met. Lane 2 shows mRNA labeled with 32P. In lane 6, the reaction was carried out in the presence of 0.5 mM cap analog.
Figure 19:
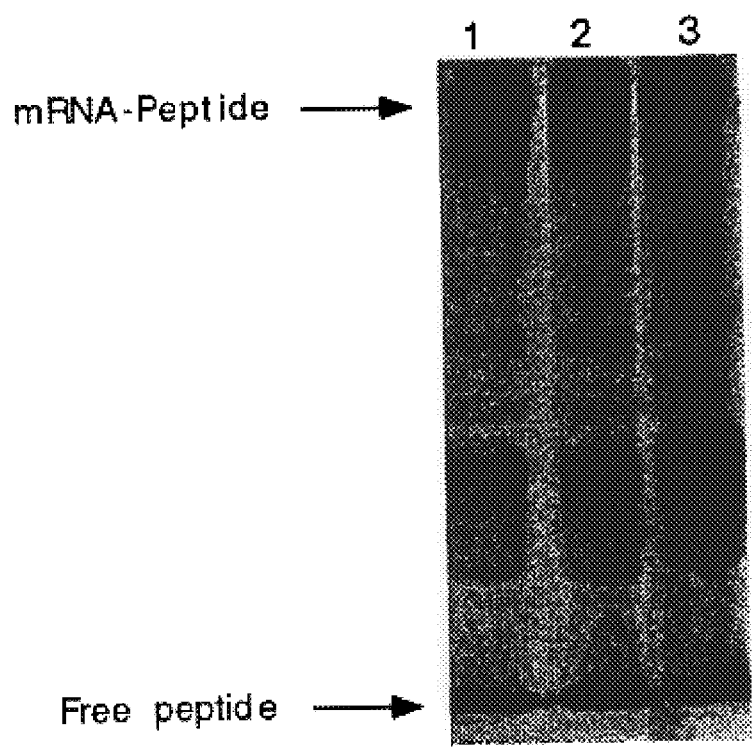
FIG. 19 is a photograph illustrating the translation of myc RNA template using lysate obtained from Ambion (lane 1), Novagen (lane 2), and Amersham (lane 3). The linker utilized was $dA_{27}dCdCP$. The concentration of the template was 600 nM, and $^{35}$S-Met was used for labeling. Translations were performed at 30° C. for 1 hour, and incubations were carried out at −20° C. overnight in the presence of 50 mM $Mg^{2+}$.

To determine the percentage of the input template converted to fusion product, the translations were performed using $^{32}$P-labeled mRNA-linker template. When the flexible linker was used and post-translational incubation was performed at –20° C. without addition of $Mg^{2+}$, about 20%, 40%, 40%, 35%, and 20% of the input template was converted to mRNA-peptide fusion when the concentration of the input RNA template was 800, 400, 200, 100, and 50 nM, respectively (FIG. 18). Similar results were obtained when the post-translational incubation was performed in the presence of 50 mM $Mg^{2+}$. The best results were achieved using lysates obtained from Novagen, Amersham, or Ambion (FIG. 19).

The mobility differences between mRNAs and mRNA-peptide fusions as measured by SDS-PAGE may be very small if the mRNA template is long. In such cases, the template may be labeled at the 5' end of the linker with $^{32}$P. The long RNA portion may then be digested with RNase H in the presence of a complementary DNA splint after translation/incubation, and the fusion efficiency determined by quantitation of the ratio of unmodified linker to linker-peptide fusion. Compared to RNase A digestion, which produces 3'-P and 5'-OH, this approach has the advantage that the $^{32}$P at the 5' end of the linker is not removed.

Intramolecular vs. Intermolecular Fusion During Post-Translational Incubation. In addition to the above experiments, we tested whether the fusion reaction that occurred at –20° C. in the presence of $Mg^{2+}$ was intra- or intermolecular in nature. Free linker ($dA_{27}dCdCP$ or $dA_{21}C_9C_9C_9dAdCdCP$, where $C_9$ is —$O(CH_2CH_2O)_3PO_2$—) was coincubated with a template containing a DNA linker, but without puromycin at the 3' end, under the translation and post-translational incubation conditions described above. In these experiments, no detectable amount (that is less than 2% of the normal level) of $^{35}$S-Met was incorporated into linker-peptide product, suggesting that post-translational fusion occurred primarily between the nascent peptide and the mRNA bound to the same ribosome.

Optimization Results. As illustrated above, by using the flexible linker and/or performing the post-translational incubation in the presence of a high concentration of $Mg^{2+}$, fusion efficiencies were increased to approximately 40% of input mRNA. These results indicated that as many as $10^{14}$ molecules of mRNA-peptide fusion could be generated per ml of in vitro translation reaction mix, producing pools of mRNA-peptide fusions of very high complexity for use in in vitro selection experiments.

SELECTIVE ENRICHMENT OF RNA-PROTEIN FUSIONS

Figure 16A:
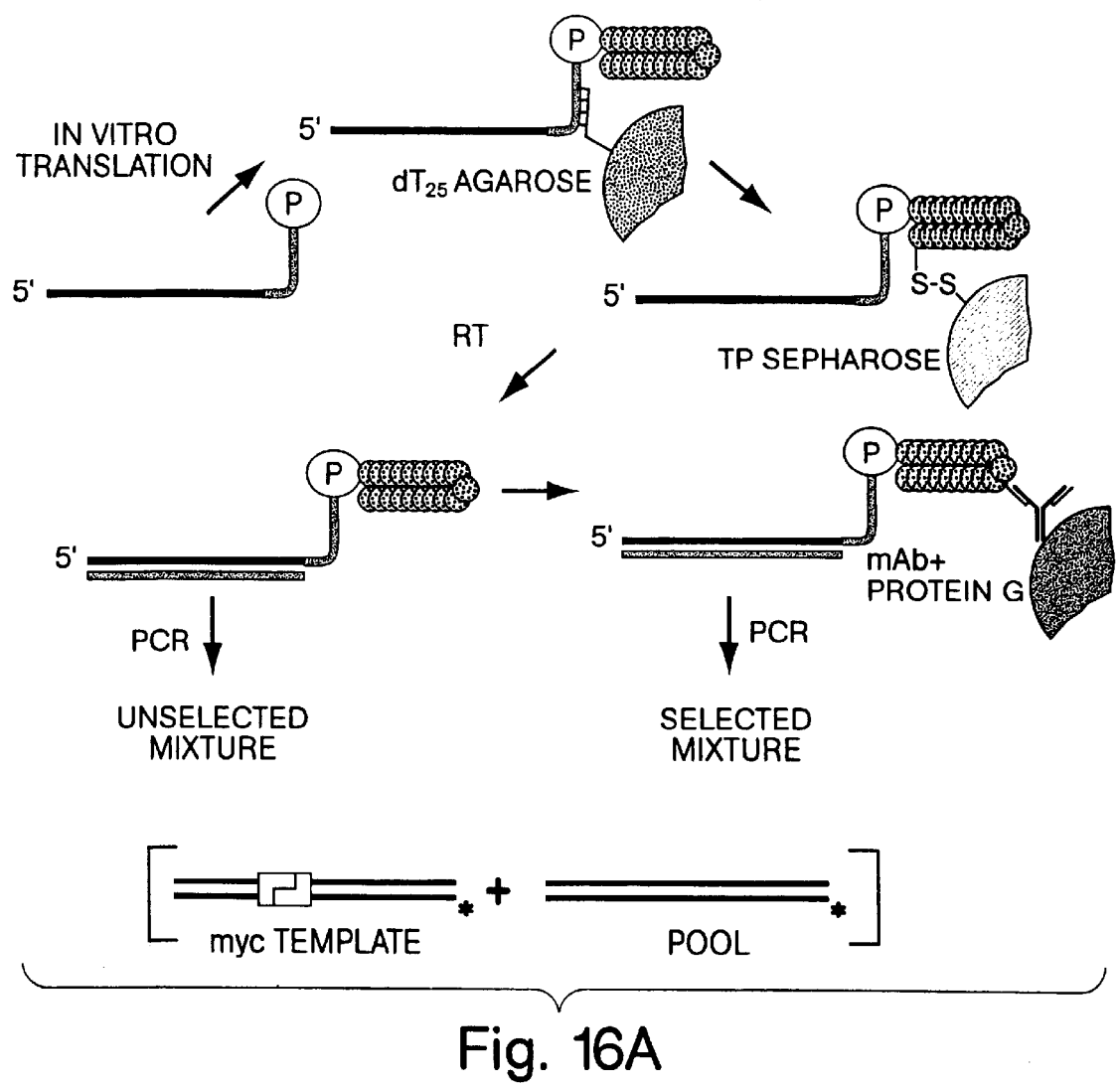
FIGS. 16A–16C are diagrams and photographs illustrating enrichment of myc dsDNA versus pool dsDNA by in vitro selection.
Figure 16B:
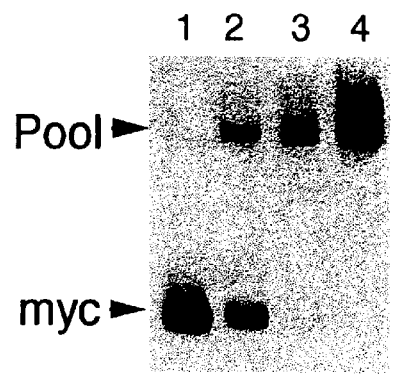
Figure 16C:
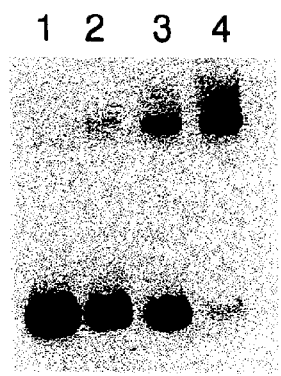

We have demonstrated the feasibility of using RNA-peptide fusions in selection and evolution experiments by enriching a particular RNA-peptide fusion from a complex pool of random sequence fusions on the basis of the encoded peptide. In particular, we prepared a series of mixtures in which a small quantity of known sequence (in this case, the long myc template, LP154) was combined with some amount of random sequence pool (that is, LP 160). These mixtures were translated, and the RNA-peptide fusion products selected by oligonucleotide and disulfide affinity chromatography as described herein. The myc-template fusions were selectively immunoprecipitated with anti-myc monoclonal antibody (FIG. 16A). To measure the enrichment obtained in this selective step, aliquots of the mixture of cDNA/mRNA-peptide fusions from before and after the immunoprecipitation were amplified by PCR in the presence of a radiolabeled primer. The amplified DNA was digested with a restriction endonuclease that cut the myc template sequence but not the pool (FIGS. 16B and 16C). Quantitation of the ratio of cut and uncut DNA indicated that the myc sequence was enriched by 20–40 fold relative to the random library by immunoprecipitation.

These experiments were carried out as follows.

Translation Reactions. Translation reactions were performed generally as described above. Specifically, reactions were performed at 30° C. for one hour according to the manufacturer's specifications (Novagen) and frozen overnight at −20° C. Two versions of six samples were made, one containing $^{35}S$ methionine and one containing cold methionine added to a final concentration of 52 μM. Reactions 1–6 contained the amounts of templates described in Table 2. All numbers in Table 2 represent picomoles of template per 25 μl reaction mixture.

TABLE 2

Template Ratios Used in Doped Selection

| Reaction | LP154 | LP160 |
|---|---|---|
| 1 | — | — |
| 2 | 5 | — |
| 3 | 1 | 20 |
| 4 | 0.1 | 20 |
| 5 | 0.01 | 20 |
| 6 | — | 20 |

Preparation of $dT_{25}$ Streptavidin Agarose. Streptavidin agarose (Pierce) was washed three times with TE 8.2 (10 mM Tris-Cl pH 8.2, 1 mM EDTA) and resuspended as a 1:1 (v/v) slurry in TE 8.2. 3' biotinyl $T_{25}$ synthesized using Bioteg CPG (Glen Research) was then added to the desired final concentration (generally 10 or 20 μM), and incubation was carried out with agitation for 1 hour. The $dT_{25}$ streptavidin agarose was then washed three times with TE 8.2 and stored at 4° C. until use.

Purification of Templates from Translation Reactions. To purify templates from translation reactions, 25 μl of each reaction was removed and added to 7.5 ml of Isolation Buffer (1M NaCl, 100 mM Tris-Cl pH 8.2, 10 mM EDTA, 0.1 mM DTT) and 125 μl of 20 μM $dT_{25}$ streptavidin agarose. This solution was incubated at 4° C. for one hour with rotation. The tubes were centrifuged and the eluent removed. One ml of Isolation Buffer was added, the slurry was resuspended, and the mixtures were transferred to 1.5 ml microcentrifuge tubes. The samples were then washed four times with 1 ml aliquots of ice cold Isolation Buffer. Hot and cold samples from identical reactions were then combined in a filter Millpore MC filter unit and were eluted from the $dT_{25}$ agarose by washing with 2 volumes of 100 μl $H_2O$, 0.1 mM DTT, and 2 volumes of 15 mM NaOH, 1 mM EDTA.

To this eluent was added 40 μl of a 50% slurry of washed thiopropyl sepharose (Pharmacia), and incubation was carried out at 4° C. with rotation for 1 hour. The samples were then washed with three 1 ml volumes of TE 8.2 and the eluent removed. One μl of 1M DTT was added to the solid (total volume approximately 20–30 μl), and the sample was incubated for several hours, removed, and washed four times with 20 μl $H_2O$ (total volume 90 μl). The eluent contained 2.5 mM thiopyridone as judged by UV absorbance. 50 μl of this sample was ethanol precipitated by adding 6 μl 3M NaOAc pH 5.2, 10 mM spermine, 1 μl glycogen (10 mg/ml, Boehringer Mannheim), and 170 μl 100% EtOH, incubating for 30 minutes at −70° C., and centrifuging for 30 minutes at 13,000 rpm in a microcentrifuge.

Reverse Transcriptase Reactions. Reverse transcription reactions were performed on both the ethanol precipitated and the thiopyridone eluent samples as follows. For the ethanol precipitated samples, 30 μl of resuspended template, $H_2O$ to 48 μl, and 200 picomoles of primer 21.103 (SEQ ID NO:22) were annealed at 70° C. for 5 minutes and cooled on ice. To this sample, 16 μl of first strand buffer (250 mM Tris-Cl pH 8.3, 375 mM KCl, and 15 mM $MgCl_2$; available from Gibco BRL, Grand Island, N.Y.), 8 μl 100 mM DTT, and 4 μl 10 mM NTP were added and equilibrated at 42° C., and 4 μl Superscript II reverse transcriptase (Gibco BRL, Grand Island, N.Y.) was added. $H_2O$ (13 μl) was added to the TP sepharose eluent (35 μl), and reactions were performed as above. After incubation for one hour, like numbered samples were combined (total volume 160 μl). 10 μl of sample was reserved for the PCR of each unselected sample, and 150 μl of sample was reserved for immunoprecipitation.

Immunoprecipitation. To carry out immunoprecipitations, 170 μl of reverse transcription reaction was added to 1 ml of Dilution Buffer (10 mM Tris-Cl, pH 8.2, 140 mM NaCl, 1% v/v Triton X-100) and 20 μl of Protein G/A conjugate (Calbiochem, La Jolla, Calif.), and precleared by incubation at 4° C. with rotation for 1 hour. The eluent was removed, and 20 μl G/A conjugate and 20 μl of monoclonal antibody (2 μg, 12 picomoles) were added, and the sample incubated with rotation for two hours at 4° C. The conjugate was precipitated by microcentrifugation at 2500 rpm for 5 minutes, the eluent removed, and the conjugate washed three times with 1 ml aliquots of ice cold Dilution Buffer. The sample was then washed with 1 ml ice cold 10 mM Tris-Cl, pH 8.2, 100 mM NaCl. The bound fragments were removed using 3 volumes of frozen 4% HOAc, and the samples were lyophilized to dryness.

PCR of Selected and Unselected Samples. PCR reactions were carried out by adding 20 μl of concentrated $NH_4OH$ to 10 µl of the unselected material and the entirety of the selected material and incubating for 5 minutes each at 55° C., 70° C., and 90° C. to destroy any RNA present in the sample. The samples were then evaporated to dryness using a speedvac. 200 µl of PCR mixture (1 µM primers 21.103 and 42.108, 200 µM dNTP in PCR buffer plus $Mg^{2+}$ (Boehringer Mannheim), and 2 µl of Taq polymerase (Boehringer Mannheim)) were added to each sample. 16 cycles of PCR were performed on unselected sample number 2, and 19 cycles were performed on all other samples.

Samples were then amplified in the presence of 5 $^{32}$P-labeled primer 21.103 according to Table 3, and purified twice individually using Wizard direct PCR purification kite (Promega) to remove all primer and shorter fragments.

TABLE 3

Amplification of Selected and Unselected PCR Samples

| Sample | Type | Volume | Cycles |
|---|---|---|---|
| 1 | unselected | 20 µl | 5 |
| 2 | unselected | 5 µl | 4 |
| 3 | unselected | 20 µl | 5 |
| 4 | unselected | 20 µl | 5 |
| 5 | unselected | 20 µl | 5 |
| 6 | unselected | 20 µl | 5 |
| 1 | selected | 20 µl | 5 |
| 2 | selected | 5 µl | 4 |
| 3 | selected | 20 µl | 5 |
| 4 | selected | 20 µl | 7 |
| 5 | selected | 20 µl | 7 |
| 6 | selected | 20 µl | 7 |

Restriction Digests. $^{32}$P labeled DNA prepared from each of the above PCR reactions was added in equal amounts (by cpm of sample) to restriction digest reactions according to Table 4. The total volume of each reaction was 25 µl. 0.5 µl of AlwnI (5 units, New England Biolabs) was added to each reaction. Samples were incubated at 37° C. for 1 hour, and the enzyme was heat inactivated by a 20 minute incubation at 65° C. The samples were then mixed with 10 µl denaturing loading buffer (1 ml ultrapure formamide (USB), 20 µl 0.5M EDTA, and 20 µl 1M NaOH), heated to 90° C. for 1 minute, cooled, and loaded onto a 12% denaturing polyacrylamide gel containing 8M urea. Following electrophoresis, the gel was fixed with 10% (v/v) HOAc, 10% (v/v)

TABLE 4

Restriction Digest Conditions w/AlwnI

| Sample | Type | Volume DNA added to reaction | Total volume |
|---|---|---|---|
| 1 | unselected | 20 µl | 25 µl |
| 2 | unselected | 4 µl | 25 µl |
| 3 | unselected | 20 µl | 25 µl |
| 4 | unselected | 20 µl | 25 µl |
| 5 | unselected | 4 µl | 25 µl |
| 6 | unselected | 20 µl | 25 µl |
| 1 | selected | 20 µl | 25 µl |
| 2 | selected | 8 µl | 25 µl |
| 3 | selected | 12 µl | 25 µl |
| 4 | selected | 12 µl | 25 µl |
| 5 | selected | 20 µl | 25 µl |
| 6 | selected | 20 µl | 25 µl |

Quantitation of Digest. The amount of myc versus pool DNA present in a sample was quantitated using a phosphorimager (Molecular Dynamics). The amount of material present in each band was determined as the integrated volume of identical reactangles drawn around the gel bands. The total cpm present in each band was calculated as the volume minus the background. Three values of background were used: (1) an average of identical squares outside the area where counts occurred on the gel; (2) the cpm present in the unselected pool lane where the myc band should appear (no band appears at this position on the gel); and (3) a normalized value that reproduced the closest value to the 10-fold template increments between unselected lanes. Lanes 2, 3, and 4 of FIGS. 16B and 16C demonstrate enrichment of the target versus the pool sequence. The demonstrable enrichment in lane 3 (unselected/selected) yielded the largest values (17, 43, and 27 fold using methods 1–3, respectively) due to the optimization of the signal to noise ratio for this sample. These results are summarized in Table 5.

TABLE 5

Enrichment of Myc Template vs. Pool

| Method | Lane 2 (20) | Lane 3 (200) | Lane 4 (2000) |
|---|---|---|---|
| 1 | 7.0 | 16.6 | 5.7 |
| 2 | 10.4 | 43 | 39 |
| 3 | 8.7 | 27 | 10.2 |

In a second set of experiments, these same PCR products were purified once using Wizard direct PCR purification kits, and digests were quantitated by method (2) above. In these experiments, similar results were obtained; enrichments of 10.7, 38, and 12 fold, respectively, were measured for samples equivalent to those in lanes 2, 3, and 4 above.

USE OF PROTEIN SELECTION SYSTEMS

The selection systems of the present invention have commercial applications in any area where protein technology is used to solve therapeutic, diagnostic, or industrial problems. This selection technology is useful for improving or altering existing proteins as well as for isolating new proteins with desired functions. These proteins may be naturally-occurring sequences, may be altered forms of naturally-occurring sequences, or may be partly or filly synthetic sequences.

Isolation of Novel Binding Reagents. In one particular application, the RNA-protein fusion technology described herein is useful for the isolation of proteins with specific binding (for example, ligand binding) properties. Proteins exhibiting highly specific binding interactions may be used as non-antibody recognition reagents, allowing RNA-protein fusion technology to circumvent traditional monoclonal antibody technology. Antibody-type reagents isolated by this method may be used in any area where traditional antibodies are utilized, including diagnostic and therapeutic applications.

Improvement of Human Antibodies. The present invention may also be used to improve human or humanized antibodies for the treatment of any of a number of diseases. In this application, antibody libraries are developed and are screened in vitro, eliminating the need for techniques such as cell-fusion or phage display. In one important application, the invention is usefull for improving single chain antibody libraries (Ward et al., Nature 341:544 (1989); and Goulot et al., J. Mol. Biol. 213:617 (1990)). For this application, the variable region may be constructed either from a human source (to minimize possible adverse immune reactions of the recipient) or may contain a totally randomized cassette (to maximize the complexity of the library). To screen for improved antibody molecules, a pool of candidate molecules are tested for binding to a target molecule (for example, an antigen immobilized as shown in FIG. 2). Higher levels of stringency are then applied to the binding step as the selection progresses from one round to the next. To increase stringency, conditions such as number of wash steps, concentration of excess competitor, buffer conditions, length of binding reaction time, and choice of immobilization matrix are altered.

Single chain antibodies may be used either directly for therapy or indirectly for the design of standard antibodies. Such antibodies have a number of potential applications, including the isolation of anti-autoimmune antibodies, immune suppression, and in the development of vaccines for viral diseases such as AIDS.

Isolation of New Catalysts. The present invention may also be used to select new catalytic proteins. In vitro selection and evolution has been used previously for the isolation of novel catalytic RNAs and DNAs, and, in the present invention, is used for the isolation of novel protein enzymes. In one particular example of this approach, a catalyst may be isolated indirectly by selecting for binding to a chemical analog of the catalyst's transition state. In another particular example, direct isolation may be carried out by selecting for covalent bond formation with a substrate (for example, using a substrate linked to an affinity tag) or by cleavage (for example, by selecting for the ability to break a specific bond and thereby liberate catalytic members of a library from a solid support).

This approach to the isolation of new catalysts has at least two important advantages over catalytic antibody technology (reviewed in Schultz et al., J. Chem. Engng. News 68:26 (1990)). First, in catalytic antibody technology, the initial pool is generally limited to the immunoglobulin fold; in contrast, the starting library of RNA-protein fusions may be either completely random or may consist, without limitation, of variants of known enzymatic structures or protein scaffolds. In addition, the isolation of catalytic antibodies generally relies on an initial selection for binding to transition state reaction analogs followed by laborious screening for active antibodies; again, in contrast, direct selection for catalysis is possible using an RNA-protein fusion library approach, as previously demonstrated using RNA libraries. In an alternative approach to isolating protein enzymes, the transition-state-analog and direct selection approaches may be combined.

Enzymes obtained by this method are highly valuable. For example, there currently exists a pressing need for novel and effective industrial catalysts that allow improved chemical processes to be developed. A major advantage of the invention is that selections may be carried out in arbitrary conditions and are not limited, for example, to in vivo conditions. The invention therefore facilitates the isolation of novel enzymes or improved variants of existing enzymes that can carry out highly specific transformations (and thereby minimize the formation of undesired byproducts) while functioning in predetermined environments, for example, environments of elevated temperature, pressure, or solvent concentration.

An In Vitro Interaction Trap. The RNA-protein fusion technology is also useful for screening cDNA libraries and cloning new genes on the basis of protein-protein interactions. By this method, a cDNA library is generated from a desired source (for example, by the method of Ausubel et al., supra, chapter 5). To each of the candidate cDNAs, a peptide acceptor (for example, as a puromycin tail) is ligated (for example, using the techniques described above for the generation of LP77, LP154, and LP160). RNA-protein fusions are then generated as described herein, and the ability of these fusions (or improved versions of the fusions) to interact with particular molecules is then tested as described above. If desired, stop codons and 3' UTR regions may be avoided in this process by either (i) adding suppressor tRNA to allow readthrough of the stop regions, (ii) removing the release factor from the translation reaction by immunoprecipitation, (iii) a combination of (i) and (ii), or (iv) removal of the stop codons and 3' UTR from the DNA sequences.

The fact that the interaction step takes place in vitro allows careful control of the reaction stringency, using nonspecific competitor, temperature, and ionic conditions. Alteration of normal small molecules with non-hydrolyzable analogs (e.g., ATP vs. ATPgS) provides for selections that discriminate between different conformers of the same molecule. This approach is useful for both the cloning and functional identification of many proteins since the RNA sequence of the selected binding partner is covalently attached and may therefore be readily isolated. In addition, the technique is useful for identifying functions and interactions of the ~50–100,000 human genes, whose sequences are currently being determined by the Human Genome project.

USE OF RNA-PROTEIN FUSIONS IN A MICROCHIP FORMAT

"DNA chips" consist of spatially defined arrays of immobilized oligonucleotides or cloned fragments of cDNA or genomic DNA, and have applications such as rapid sequencing and transcript profiling. By annealing a mixture of RNA-protein fusions (for example, generated from a cellular DNA or RNA pool), to such a DNA chip, it is possible to generate a "protein display chip," in which each spot corresponding to one immobilized sequence is capable of annealing to its corresponding RNA sequence in the pool of RNA-protein fusions. By this approach, the corresponding protein is immobilized in a spatially defined manner because of its linkage to its own mRNA, and chips containing sets of DNA sequences display the corresponding set of proteins. Alternatively, peptide fragments of these proteins may be displayed if the fusion library is generated from smaller fragments of cDNAs or genomic DNAs.

Such ordered displays of proteins and peptides have many uses. For example, they represent powerful tools for the identification of previously unknown protein-protein interactions. In one specific format, a probe protein is detectably labeled (for example, with a fluorescent dye), and the labeled protein is incubated with a protein display chip. By this approach, the identity of proteins that are able to bind the probe protein are determined from the location of the spots on the chip that become labeled due to binding of the probe. Another application is the rapid determination of proteins that are chemically modified through the action of modifying enzymes (for example, protein kinases, acyl transferases, and methyl transferases). By incubating the protein display chip with the enzyme of interest and a radioactively labeled substrate, followed by washing and autoradiography, the location and hence the identity of those proteins that are substrates for the modifying enzyme may be readily determined. In addition, the use of this approach with ordered displays of small peptides allows the further localization of such modification sites.

Protein display technology may be carried out using arrays of nucleic acids (including RNA, but preferably DNA) immobilized on any appropriate solid support. Exemplary solid supports may be made of materials such as glass (e.g., glass plates), silicon or silicon-glass (e.g., microchips), or gold (e.g., gold plates). Methods for attaching nucleic acids to precise regions on such solid surfaces, e.g., photolithographic methods, are well known in the art, and may be used to generate solid supports (such as DNA chips) for use in the invention. Exemplary methods for this purpose include, without limitation, Schena et al., Science 270:467–470 (1995); Kozal et al., Nature Medicine 2:753–759 (1996); Cheng et al., Nucleic Acids Research 24:380–385 (1996); Lipshutz et al., BioTechniques 19:442–447 (1995); Pease et al., Proc. Natl. Acad. Sci. USA 91:5022–5026 (1994); Fodor et al., Nature 364:555–556 (1993); Pirrung et al., U.S. Pat. No. 5,143,854; and Fodor et al., WO 92/10092.

What is claimed is:

1. A molecule comprising a ribonucleic acid covalently bonded through an amide bond to an antibody, wherein said antibody is encoded by said ribonucleic acid.

2. A molecule comprising a ribonucleic acid covalently bonded to an antibody, said antibody being entirely encoded by said ribonucleic acid.

3. The molecule of claim 1, wherein said amide bond is resistant to cleavage by a ribosome.

4. The molecule of any of claims 1, 2, or 3, wherein said antibody is a single chain antibody.

5. The molecule of any of claims 1, 2, or 3, wherein said antibody is a human antibody.

6. The molecule of any of claims 1, 2, or 3, wherein the variable region of said antibody is derived from a human antibody.

7. The molecule of any of claims 1, 2, or 3, wherein the variable region of said antibody comprises a randomized region.

8. The molecule of claim 1 or 2, wherein said molecule further comprises a peptide acceptor positioned between said ribonucleic acid and said antibody.

9. An RNA-antibody fusion selected by the method comprising the steps of:
   a) providing a population of candidate RNA molecules, each of which comprises a translation initiation sequence and a start codon operably linked to a candidate antibody coding sequence and each of which is operably linked to a peptide acceptor at the 3' end of said candidate antibody coding sequence;
   b) in vitro or in situ translating said candidate antibody coding sequences to produce a population of candidate RNA-antibody fusions;
   c) contacting said population of candidate RNA-antibody fusions with a target antigen; and
   d) selecting an RNA-antibody fusion that binds to said target antigen.

10. An RNA-antibody fusion selected by the method comprising the steps of:
    a) providing a population of candidate RNA molecules, each of which comprises a translation initiation sequence and a start codon operably linked to a candidate antibody coding sequence and each of which is operably linked to a peptide acceptor at the 3' end of said candidate antibody coding sequence;
    b) in vitro translating said candidate antibody coding sequences to produce a population of candidate RNA-antibody fusions;
    c) contacting said population of candidate RNA-antibody fusions with a target antigen; and
    d) selecting an RNA-antibody fusion that binds to said target antigen.

11. An RNA-antibody fusion comprising an antibody portion having an altered binding affinity or specificity for a target antigen relative to the binding affinity or specificity of a reference antibody, said RNA-antibody fusion selected by the method comprising the steps of:
    a) producing a population of candidate RNA molecules, each having a candidate antibody coding sequence which differs from said reference antibody coding sequence, said RNA molecules each comprising a translation initiation sequence and a start codon operably linked to said candidate antibody coding sequence and each being operably linked to a peptide acceptor at the 3' end;
    b) in vitro or in situ translating said candidate antibody coding sequences to produce a population of candidate RNA-antibody fusions;

c) contacting said population of candidate RNA-antibody fusions with said target antigen; and d) selecting an RNA-antibody fusion, the antibody portion of which has a binding affinity or specificity for said target antigen that is altered relative to the binding affinity or specificity of said reference antibody for said target antigen.

12. An RNA-antibody fusion comprising an antibody portion having an altered binding affinity or specificity for a target antigen relative to the binding affinity or specificity of a reference antibody, said RNA-antibody fusion selected by the method comprising the steps of:

a) producing a population of candidate RNA molecules, each having a candidate antibody coding sequence which differs from said reference antibody coding sequence, said RNA molecules each comprising a translation initiation sequence and a start codon operably linked to said candidate antibody coding sequence and each being operably linked to a peptide acceptor at the 3' end;

b) in vitro translating said candidate antibody coding sequences to produce a population of candidate RNA-antibody fusions;

c) contacting said population of candidate RNA-antibody fusions with said target antigen; and d) selecting an RNA-antibody fusion, the antibody portion of which has a binding affinity or specificity for said target antigen that is altered relative to the binding affinity or specificity of said reference antibody for said target antigen.

* * * * *

```
                          SEQUENCE LISTING

<160> NUMBER OF SEQ ID NOS: 33

<210> SEQ ID NO 1
<211> LENGTH: 76
<212> TYPE: RNA
<213> ORGANISM: Artificial Sequence
<220> FEATURE:
<223> OTHER INFORMATION: Translation template

<400> SEQUENCE: 1
gggaggacga aauggaacag aaacugaucu cugaagaaga ccugaacaaa aaaaaaaaaa        60
aaaaaaaaaa aaaacc                                                       76

<210> SEQ ID NO 2
<211> LENGTH: 10
<212> TYPE: PRT
<213> ORGANISM: Homo sapiens

<400> SEQUENCE: 2

Glu Gln Lys Leu Ile Ser Glu Glu Asp Leu
 1               5                  10

<210> SEQ ID NO 3
<211> LENGTH: 153
<212> TYPE: RNA
<213> ORGANISM: Artificial Sequence
<220> FEATURE:
<223> OTHER INFORMATION: Translation template

<400> SEQUENCE: 3
gggacaauua cuauuuacaa uuacaauggc ugaagaacag aaacugaucu cugaagaaga        60
ccugcugcgu aaacgucgug aacagcugaa acacaaacug gaacagcugc guaacucuug       120
cgcuaaaaaa aaaaaaaaaa aaaaaaaaaa acc                                   153

<210> SEQ ID NO 4
<211> LENGTH: 34
<212> TYPE: PRT
<213> ORGANISM: Artificial Sequence
<220> FEATURE:
<223> OTHER INFORMATION: Random peptide
<220> FEATURE:
<221> NAME/KEY: VARIANT
<222> LOCATION: (1)...(34)
<223> OTHER INFORMATION: Xaa is any amino acid.

<400> SEQUENCE: 4

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Gln Leu Arg Asn Ser
            20                  25                  30

Cys Ala
```

```
<210> SEQ ID NO 5
<211> LENGTH: 25
<212> TYPE: RNA
<213> ORGANISM: Tobacco Mosaic Virus

<400> SEQUENCE: 5
gggacaauua cuauuuacaa uuaca                                              25

<210> SEQ ID NO 6
<211> LENGTH: 10
<212> TYPE: RNA
<213> ORGANISM: Escherichia coli

<400> SEQUENCE: 6
ggaggacgaa                                                               10

<210> SEQ ID NO 7
<211> LENGTH: 34
<212> TYPE: PRT
<213> ORGANISM: Homo sapiens

<400> SEQUENCE: 7

Met Ala Glu Glu Gln Lys Leu Ile Ser Glu Glu Asp Leu Leu Arg Lys
 1               5                  10                  15

Arg Arg Glu Gln Lys Leu Lys His Lys Leu Glu Gln Leu Arg Asn Ser
            20                  25                  30

Cys Ala

<210> SEQ ID NO 8
<211> LENGTH: 29
<212> TYPE: DNA
<213> ORGANISM: Artificial Sequence
<220> FEATURE:
<223> OTHER INFORMATION: Translation template

<400> SEQUENCE: 8
aaaaaaaaaa aaaaaaaaaa aaaaaaacc                                          29

<210> SEQ ID NO 9
<211> LENGTH: 12
<212> TYPE: DNA
<213> ORGANISM: Artificial Sequence
<220> FEATURE:
<223> OTHER INFORMATION: Translation template

<400> SEQUENCE: 9
aaaaaaaaaa cc                                                            12

<210> SEQ ID NO 10
<211> LENGTH: 24
<212> TYPE: DNA
<213> ORGANISM: Artificial Sequence
<220> FEATURE:
<223> OTHER INFORMATION: Translation template

<400> SEQUENCE: 10
cgcggttttt attttttttt ttcc                                               24

<210> SEQ ID NO 11
<211> LENGTH: 42
<212> TYPE: RNA
<213> ORGANISM: Artificial Sequence
<220> FEATURE:
<223> OTHER INFORMATION: Translation template
```

```
<400> SEQUENCE: 11
ggaggacgaa augaaaaaaa aaaaaaaaaa aaaaaaaaaa cc                42

<210> SEQ ID NO 12
<211> LENGTH: 42
<212> TYPE: RNA
<213> ORGANISM: Artificial Sequence
<220> FEATURE:
<223> OTHER INFORMATION: Translation template

<400> SEQUENCE: 12
ggaggacgaa cugaaaaaaa aaaaaaaaaa aaaaaaaaaa cc                42

<210> SEQ ID NO 13
<211> LENGTH: 42
<212> TYPE: RNA
<213> ORGANISM: Artificial Sequence
<220> FEATURE:
<223> OTHER INFORMATION: Translation template

<400> SEQUENCE: 13
ggaggacgaa augaaaaaaa aaaaaaaaaa aaaaaaaaaa cc                42

<210> SEQ ID NO 14
<211> LENGTH: 36
<212> TYPE: RNA
<213> ORGANISM: Artificial Sequence
<220> FEATURE:
<223> OTHER INFORMATION: Translation template

<400> SEQUENCE: 14
ggaggacgaa cugaaaaaaa aaaaaaaaaa aaaacc                       36

<210> SEQ ID NO 15
<211> LENGTH: 33
<212> TYPE: RNA
<213> ORGANISM: Artificial Sequence
<220> FEATURE:
<223> OTHER INFORMATION: Translation template

<400> SEQUENCE: 15
ggaggacgaa cugaaaaaaa aaaaaaaaaa acc                          33

<210> SEQ ID NO 16
<211> LENGTH: 30
<212> TYPE: RNA
<213> ORGANISM: Artificial Sequence
<220> FEATURE:
<223> OTHER INFORMATION: Translation template

<400> SEQUENCE: 16
ggaggacgaa cugaaaaaaa aaaaaaaacc                              30

<210> SEQ ID NO 17
<211> LENGTH: 159
<212> TYPE: RNA
<213> ORGANISM: Artificial Sequence
<220> FEATURE:
<223> OTHER INFORMATION: Translation template
<220> FEATURE:
<221> NAME/KEY: misc_feature
<222> LOCATION: (1)...(159)
<223> OTHER INFORMATION: n = A,U,C or G

<400> SEQUENCE: 17
gggacaauua cuauuuacaa uuacaaugnn snnsnnsnns nnsnnsnnsn nsnnsnnsnn    60
```

```
snnsnnsnns nnsnnsnnsn nsnnsnnsnn snnsnnsnns nnsnnsnnsc agcugcguaa    120
cucuugcgcu aaaaaaaaaa aaaaaaaaaa aaaaaaacc                           159
```

<210> SEQ ID NO 18
<211> LENGTH: 64
<212> TYPE: DNA
<213> ORGANISM: Homo sapiens

<400> SEQUENCE: 18

```
gttcaggtct tcttgagaga tcagtttctg ttccatttcg tcctccctat agtgagtcgt    60
atta                                                                 64
```

<210> SEQ ID NO 19
<211> LENGTH: 18
<212> TYPE: DNA
<213> ORGANISM: Homo sapiens

<400> SEQUENCE: 19

```
taatacgact cactatag                                                  18
```

<210> SEQ ID NO 20
<211> LENGTH: 12
<212> TYPE: PRT
<213> ORGANISM: Homo sapiens

<400> SEQUENCE: 20

```
Met Glu Gln Lys Leu Ile Ser Glu Glu Asp Leu Asn
 1               5                  10
```

<210> SEQ ID NO 21
<211> LENGTH: 99
<212> TYPE: DNA
<213> ORGANISM: Homo sapiens

<400> SEQUENCE: 21

```
agcgcaagag ttacgcagct gttccagttt gtgtttcagc tgttcacgac gtttacgcag    60
caggtcttct tcagagatca gtttctgttc ttcagccat                           99
```

<210> SEQ ID NO 22
<211> LENGTH: 21
<212> TYPE: DNA
<213> ORGANISM: Homo sapiens

<400> SEQUENCE: 22

```
agcgcaagag ttacgcagct g                                              21
```

<210> SEQ ID NO 23
<211> LENGTH: 63
<212> TYPE: DNA
<213> ORGANISM: Homo sapiens

<400> SEQUENCE: 23

```
taatacgact cactataggg acaattacta tttacaatta caatggctga agaacagaaa    60
ctg                                                                  63
```

<210> SEQ ID NO 24
<211> LENGTH: 33
<212> TYPE: PRT
<213> ORGANISM: Homo sapiens

<400> SEQUENCE: 24

```
Met Ala Glu Glu Gln Lys Leu Ile Ser Glu Glu Asp Leu Leu Arg Lys
 1               5                  10                  15

Arg Arg Glu Gln Leu Lys His Lys Leu Glu Gln Leu Arg Asn Ser Cys
            20                  25                  30

Ala

<210> SEQ ID NO 25
<211> LENGTH: 49
<212> TYPE: DNA
<213> ORGANISM: Artificial Sequence
<220> FEATURE:
<223> OTHER INFORMATION: Primers for RNA pool

<400> SEQUENCE: 25
ccctgttaat gataaatgtt aatgttacgt cgacgcattg agataccga          49

<210> SEQ ID NO 26
<211> LENGTH: 42
<212> TYPE: DNA
<213> ORGANISM: Artificial Sequence
<220> FEATURE:
<223> OTHER INFORMATION: Primers for RNA pool

<400> SEQUENCE: 26
taatacgact cactataggg acaattacta tttacaatta ca                 42

<210> SEQ ID NO 27
<211> LENGTH: 21
<212> TYPE: DNA
<213> ORGANISM: Artificial Sequence
<220> FEATURE:
<223> OTHER INFORMATION: Primers for RNA pool

<400> SEQUENCE: 27
agcgcaagag ttacgcagct g                                        21

<210> SEQ ID NO 28
<211> LENGTH: 19
<212> TYPE: DNA
<213> ORGANISM: Artificial Sequence
<220> FEATURE:
<223> OTHER INFORMATION: DNA splint

<400> SEQUENCE: 28 ttttttttt agcgcaaga                                            19

<210> SEQ ID NO 29
<211> LENGTH: 18
<212> TYPE: DNA
<213> ORGANISM: Homo sapiens

<400> SEQUENCE: 29
gtggtatttg tgagccag                                            18

<210> SEQ ID NO 30
<211> LENGTH: 40
<212> TYPE: DNA
<213> ORGANISM: Phage T7

<400> SEQUENCE: 30
taatacgact cactataggg acacttgctt ttgacacaac                    40

<210> SEQ ID NO 31
```

```
<211> LENGTH: 20
<212> TYPE: DNA
<213> ORGANISM: Artificial Sequence
<220> FEATURE:
<223> OTHER INFORMATION: DNA splint

<400> SEQUENCE: 31
tttttttttt gtggtatttg                                        20

<210> SEQ ID NO 32
<211> LENGTH: 124
<212> TYPE: RNA
<213> ORGANISM: Homo sapiens

<400> SEQUENCE: 32
gggacaauua cuauuuacaa uuacaauggc ugaagaacag aaacugaucu cugaagaaga    60
ccugcugcgu aaacgucgug aacagcugaa acacaaacug gaacagcugc guaacucuug   120
cgcu                                                               124

<210> SEQ ID NO 33
<211> LENGTH: 19
<212> TYPE: DNA
<213> ORGANISM: Artificial Sequence
<220> FEATURE:
<223> OTHER INFORMATION: DNA splint

<400> SEQUENCE: 33
tttttttttt agcgcaaga                                         19
```